(12) United States Patent
English

(10) Patent No.: US 12,296,108 B2
(45) Date of Patent: May 13, 2025

(54) DEVICE FOR PROVIDING MULTIPLE TYPES OF THERAPY TO A USER

(71) Applicant: Therabody, Inc., Los Angeles, CA (US)

(72) Inventor: Trent K. English, Williamston, MI (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/384,015

(22) Filed: Oct. 26, 2023

(65) Prior Publication Data

US 2024/0050689 A1 Feb. 15, 2024

Related U.S. Application Data

(63) Continuation-in-part of application No. PCT/US2023/014896, filed on Mar. 9, 2023.

(60) Provisional application No. 63/433,094, filed on Dec. 16, 2022, provisional application No. 63/421,602, filed on Nov. 2, 2022, provisional application No. 63/415,007, filed on Oct. 11, 2022, provisional (Continued)

(51) Int. Cl.
*A61M 21/02* (2006.01)
*A61H 23/02* (2006.01)
*A61M 21/00* (2006.01)

(52) U.S. Cl.
CPC ............. *A61M 21/02* (2013.01); *A61H 23/02* (2013.01); *A61M 2021/0022* (2013.01); *A61M 2021/0066* (2013.01); *A61M 2021/0088* (2013.01); *A61M 2205/052* (2013.01); *A61M 2205/3306* (2013.01); *A61M 2205/3606* (2013.01); *A61M 2205/3673* (2013.01); *A61M 2205/502* (2013.01); *A61M 2209/088* (2013.01); *A61M 2230/06* (2013.01)

(58) Field of Classification Search
CPC .... A61H 2201/0153; A61H 2201/1635; A61H 2201/165; A61H 2201/501; A61H 2201/5043; A61H 2201/5046; A61H 2230/065; A61H 23/0254; A61H 23/0245; A61H 39/04; A61H 23/02; A61H 19/00; A61H 19/30; A61M 2021/0022; A61M 2021/0088; A61M 21/00; A61M 21/02; A61M 2205/505

See application file for complete search history.

(56) References Cited

U.S. PATENT DOCUMENTS 4,728,934 A 3/1988 Pfander et al.
5,097,828 A 3/1992 Deutsch
(Continued)

FOREIGN PATENT DOCUMENTS

CN 200970326 Y 11/2007
CN 103284874 A 9/2013
(Continued)

OTHER PUBLICATIONS

U.S. Appl. No. 17/941,056, filed Sep. 9, 2022, 858 pages.
(Continued)

*Primary Examiner* — Christine H Matthews
(74) *Attorney, Agent, or Firm* — Sterne, Kessler, Goldstein & Fox P.L.L.C.

(57) ABSTRACT

Devices, systems, and methods can be used to provide therapy to users and/or to monitor various physiological parameters of the user.

22 Claims, 22 Drawing Sheets

Related U.S. Application Data application No. 63/408,564, filed on Sep. 21, 2022, provisional application No. 63/333,595, filed on Apr. 22, 2022, provisional application No. 63/318,591, filed on Mar. 10, 2022.

(56) References Cited

U.S. PATENT DOCUMENTS

| | | |
|---|---|---|
| 5,575,761 A | 11/1996 | Hajianpour |
| 5,611,771 A | 3/1997 | Taylor |
| 6,076,018 A | 6/2000 | Sturman et al. |
| 6,155,995 A | 12/2000 | Lin |
| 6,228,103 B1 | 5/2001 | Grey et al. |
| 6,567,695 B1 | 5/2003 | Gruzdowich et al. |
| 6,918,879 B2 | 7/2005 | Ting et al. |
| 7,127,288 B2 | 10/2006 | Sturman et al. |
| 7,241,303 B2 | 7/2007 | Reiss et al. |
| 7,293,383 B2 | 11/2007 | Fishman et al. |
| 7,544,168 B2 | 6/2009 | Nitzan |
| 7,637,878 B2 | 12/2009 | Lin |
| 7,755,602 B2 | 7/2010 | Tremblay et al. |
| 7,763,046 B2 | 7/2010 | Schouten et al. |
| 8,086,301 B2 | 12/2011 | Cho et al. |
| 8,142,373 B1 | 3/2012 | Riles |
| 8,206,327 B2 | 6/2012 | Wu |
| 8,585,605 B2 | 11/2013 | Sola I Caros et al. |
| 8,668,045 B2 | 3/2014 | Cohen |
| 8,717,152 B2 | 5/2014 | Bhatia et al. |
| 8,787,006 B2 | 7/2014 | Golko et al. |
| 8,944,958 B1 | 2/2015 | Brumback et al. |
| 9,042,971 B2 | 5/2015 | Brumback et al. |
| 9,049,998 B2 | 6/2015 | Brumback et al. |
| 9,307,906 B2 | 4/2016 | Harte et al. |
| 9,320,676 B2 | 4/2016 | Chou |
| 9,600,994 B2 | 3/2017 | Park et al. |
| 9,655,548 B2 | 5/2017 | Hong et al. |
| 9,675,782 B2 | 6/2017 | Connolly |
| 9,730,591 B2 | 8/2017 | Ahmed et al. |
| 9,884,164 B2 | 2/2018 | Tass |
| 9,886,093 B2 | 2/2018 | Moussette et al. |
| 9,936,908 B1 | 4/2018 | Acosta et al. |
| 10,058,148 B1 | 8/2018 | Wittenberg et al. |
| 10,076,662 B2 | 9/2018 | Tuan |
| 10,092,224 B2 | 10/2018 | Chowdhury |
| 10,191,550 B1 | 1/2019 | Nussbaum et al. |
| 10,216,894 B2 | 2/2019 | Hong et al. |
| 10,238,575 B2 | 3/2019 | Darna |
| 10,258,117 B2 | 4/2019 | Graber et al. |
| 10,448,711 B2 | 10/2019 | Kallman et al. |
| 10,470,922 B1 | 11/2019 | Venturi |
| 10,487,127 B2 | 11/2019 | Stimson |
| 10,497,246 B2 | 12/2019 | Arnold et al. |
| 10,512,407 B2 | 12/2019 | Richards et al. |
| 10,532,181 B2 | 1/2020 | Hooper et al. |
| 10,627,861 B2 | 4/2020 | Connor |
| 10,702,171 B2 | 7/2020 | Narasimhan et al. |
| 10,735,831 B2 | 8/2020 | Dixit |
| 10,758,451 B1 | 9/2020 | McDevitt et al. |
| 10,772,394 B1 | 9/2020 | Michalske |
| 10,786,666 B2 | 9/2020 | Chu et al. |
| 10,849,822 B2 | 12/2020 | Zhang et al. |
| 10,854,103 B2 | 12/2020 | O'Dowd et al. |
| 10,881,307 B1 | 1/2021 | Sullivan et al. |
| 10,925,541 B2 | 2/2021 | Tokko et al. |
| 10,974,019 B2 | 4/2021 | Sunnen et al. |
| 10,993,872 B2 | 5/2021 | Novich et al. |
| 10,993,874 B1 | 5/2021 | Marton et al. |
| 11,000,437 B2 | 5/2021 | Mayo et al. |
| 11,031,117 B2 | 6/2021 | Mayo et al. |
| 11,033,708 B2 | 6/2021 | Blahnik et al. |
| 11,033,709 B2 | 6/2021 | Mayo et al. |
| 11,079,851 B2 | 8/2021 | Eagleman et al. |
| 11,079,854 B2 | 8/2021 | Eagleman et al. |
| 11,092,999 B2 | 8/2021 | Fu et al. |
| 11,185,237 B2 | 11/2021 | Peters et al. |
| 11,260,198 B2 | 3/2022 | Rabin et al. |
| D963,189 S | 9/2022 | Qiao |
| 11,478,606 B1 | 10/2022 | English et al. |
| 11,602,454 B1 | 3/2023 | Aguiar et al. |
| 11,730,916 B1 | 8/2023 | Hill |
| 11,944,757 B2 | 4/2024 | English et al. |
| 11,969,557 B1 | 4/2024 | English |
| 2002/0156502 A1 | 10/2002 | Tuan |
| 2003/0130690 A1 | 7/2003 | Porrata et al. |
| 2004/0044384 A1 | 3/2004 | Leber et al. |
| 2004/0098037 A1 | 5/2004 | Grey et al. |
| 2005/0209504 A1 | 9/2005 | Elliott |
| 2007/0088234 A1 | 4/2007 | Tseng |
| 2007/0088385 A1 | 4/2007 | Perry |
| 2007/0100262 A1 | 5/2007 | Simos et al. |
| 2008/0027363 A1 | 1/2008 | Brueckmann et al. |
| 2008/0195006 A1 | 8/2008 | Stark et al. |
| 2009/0177129 A1 | 7/2009 | Chan et al. |
| 2009/0254014 A1 | 10/2009 | Son |
| 2010/0010357 A1 | 1/2010 | Ostrowiecki |
| 2011/0178360 A1 | 7/2011 | Gavish et al. |
| 2011/0251532 A1 | 10/2011 | Yang |
| 2011/0313239 A1 | 12/2011 | Ahne |
| 2012/0316480 A1 | 12/2012 | Nolan et al. |
| 2012/0323149 A1 | 12/2012 | Chou |
| 2013/0123570 A1 | 5/2013 | Ly et al. |
| 2013/0184623 A1 | 7/2013 | Fraser |
| 2013/0218197 A1 | 8/2013 | Tarumi |
| 2013/0331914 A1 | 12/2013 | Lee et al. |
| 2015/0049591 A1 | 2/2015 | Adams et al. |
| 2015/0049951 A1 | 2/2015 | Chaturvedi et al. |
| 2015/0182375 A1 | 7/2015 | Binversie et al. |
| 2015/0190607 A1 | 7/2015 | Sugio et al. |
| 2015/0224025 A1 | 8/2015 | Darna |
| 2015/0351999 A1 | 12/2015 | Brouse |
| 2015/0379880 A1 | 12/2015 | Sethi |
| 2016/0000640 A1 | 1/2016 | Lai et al. |
| 2016/0008206 A1 | 1/2016 | Devanaboyina |
| 2016/0058375 A1 | 3/2016 | Rothkopf |
| 2016/0155362 A1 | 6/2016 | Joshi et al. |
| 2016/0166463 A1 | 6/2016 | Douglas et al. |
| 2016/0213558 A1 | 7/2016 | Stanbridge |
| 2016/0255944 A1 | 9/2016 | Baranski et al. |
| 2016/0346501 A1 | 12/2016 | Hooper et al. |
| 2016/0374886 A1 | 12/2016 | Wyatt et al. |
| 2017/0027459 A1 | 2/2017 | Shimuta |
| 2017/0036009 A1 | 2/2017 | Hughes et al. |
| 2017/0049611 A1 | 2/2017 | Rosh Vora et al. |
| 2017/0113039 A1 | 4/2017 | Tuan |
| 2017/0209333 A1 | 7/2017 | Shoup et al. |
| 2017/0216546 A1 | 8/2017 | Henry et al. |
| 2017/0246076 A1 | 8/2017 | Miller et al. |
| 2017/0265563 A1 | 9/2017 | Ma et al. |
| 2017/0291007 A1 | 10/2017 | Dubey et al. |
| 2017/0296429 A1 | 10/2017 | Mayo et al. |
| 2017/0340209 A1 | 11/2017 | Klaassen et al. |
| 2017/0354795 A1 | 12/2017 | Blahnik et al. |
| 2017/0372565 A1 | 12/2017 | Do et al. |
| 2018/0028396 A1 | 2/2018 | Brodsky |
| 2018/0033263 A1 | 2/2018 | Novich et al. |
| 2018/0036534 A1 | 2/2018 | Shin |
| 2018/0056029 A1 | 3/2018 | Akimoto et al. |
| 2018/0078206 A1 | 3/2018 | Aimone et al. |
| 2018/0085283 A1 | 3/2018 | Rahman |
| 2018/0099143 A1 | 4/2018 | Kim et al. |
| 2018/0110960 A1 | 4/2018 | Youngblood et al. |
| 2018/0147086 A1 | 5/2018 | Evans et al. |
| 2018/0192947 A1 | 7/2018 | Tokko et al. |
| 2018/0228689 A1 | 8/2018 | Lach et al. |
| 2018/0231939 A1 | 8/2018 | Kim |
| 2018/0256432 A1 | 9/2018 | Mayo et al. |
| 2018/0318545 A1 | 11/2018 | Jones et al. |
| 2018/0333558 A1 | 11/2018 | Levendowski et al. |
| 2019/0001131 A1 | 1/2019 | Ziv |
| 2019/0029878 A1 | 1/2019 | Linder et al. |
| 2019/0070057 A1 | 3/2019 | Conner et al. |
| 2019/0108852 A1 | 4/2019 | Eagleman et al. |
| 2019/0110950 A1 | 4/2019 | Smith et al. |
| 2019/0125619 A1 | 5/2019 | Zeutzius et al. |

(56) References Cited

U.S. PATENT DOCUMENTS

| | | | |
|---|---|---|---|
| 2019/0163270 A1 | 5/2019 | Da Silva et al. | |
| 2019/0223781 A1 | 7/2019 | Arrington et al. | |
| 2019/0261313 A1* | 8/2019 | Borras | H04M 1/72412 |
| 2019/0262223 A1 | 8/2019 | Mitchell, Jr. | |
| 2019/0269914 A1 | 9/2019 | Moaddeb et al. | |
| 2019/0290143 A1 | 9/2019 | Iwata et al. | |
| 2019/0298181 A1 | 10/2019 | Iwata et al. | |
| 2019/0298265 A1 | 10/2019 | Keating et al. | |
| 2020/0061377 A1 | 2/2020 | Siegle et al. | |
| 2020/0085380 A1 | 3/2020 | Sampson | |
| 2020/0178887 A1 | 6/2020 | Ramirez et al. | |
| 2020/0202120 A1 | 6/2020 | Shelly et al. | |
| 2020/0215296 A1 | 7/2020 | Rabin et al. | |
| 2020/0215298 A1 | 7/2020 | Rabin et al. | |
| 2020/0219615 A1 | 7/2020 | Rabin et al. | |
| 2020/0222279 A1 | 7/2020 | Spring et al. | |
| 2020/0261303 A1 | 8/2020 | Bennett | |
| 2020/0268602 A1 | 8/2020 | Akaikine et al. | |
| 2020/0289001 A1 | 9/2020 | Mantrawadi et al. | |
| 2020/0297574 A1 | 9/2020 | Poon | |
| 2020/0306493 A1 | 10/2020 | Lee | |
| 2020/0324104 A1 | 10/2020 | Labuschagne et al. | |
| 2020/0356172 A1 | 11/2020 | Fainstain | |
| 2020/0389711 A1 | 12/2020 | Dixit | |
| 2021/0085559 A1 | 3/2021 | Smith et al. | |
| 2021/0089130 A1 | 3/2021 | Novich et al. | |
| 2021/0117002 A1 | 4/2021 | Eagleman et al. | |
| 2021/0205169 A1 | 7/2021 | Schnieder et al. | |
| 2021/0208684 A1 | 7/2021 | Eagleman et al. | |
| 2021/0236370 A1 | 8/2021 | Mayo et al. | |
| 2021/0275386 A1 | 9/2021 | Ravikumar et al. | |
| 2021/0307630 A1 | 10/2021 | Sano et al. | |
| 2021/0338971 A1 | 11/2021 | Blahnik et al. | |
| 2021/0386594 A1 | 12/2021 | Ramanan et al. | |
| 2021/0393152 A1 | 12/2021 | Young et al. | |
| 2022/0105359 A1 | 4/2022 | Rappaport | |
| 2022/0241137 A1 | 8/2022 | Solana et al. | |
| 2022/0287909 A1 | 9/2022 | Sanchez Solana et al. | |
| 2023/0001191 A1 | 1/2023 | Schwarz et al. | |
| 2023/0062185 A1 | 3/2023 | Nazarian et al. | |
| 2023/0096515 A1 | 3/2023 | McDevitt et al. | |
| 2023/0165746 A1 | 6/2023 | Wersland et al. | |
| 2023/0277410 A1 | 9/2023 | Cisneros et al. | |
| 2023/0329902 A1 | 10/2023 | Aguiar et al. | |
| 2023/0347102 A1 | 11/2023 | Nazarian et al. | |
| 2023/0398324 A1 | 12/2023 | McVey et al. | |
| 2024/0023820 A1 | 1/2024 | English | |
| 2024/0225463 A1 | 7/2024 | English | |
| 2024/0261534 A1 | 8/2024 | English | |

FOREIGN PATENT DOCUMENTS

| | | |
|---|---|---|
| CN | 106333667 A | 1/2017 |
| CN | 107349092 A | 11/2017 |
| CN | 107349093 A | 11/2017 |
| CN | 108514470 A | 9/2018 |
| CN | 210019307 U | 2/2020 |
| CN | 210228475 U | 4/2020 |
| CN | 210673734 U | 6/2020 |
| CN | 210932663 U | 7/2020 |
| CN | 210933465 U | 7/2020 |
| CN | 211934039 U | 11/2020 |
| CN | 107129690 B | 1/2021 |
| CN | 212489876 U | 2/2021 |
| CN | 212574862 U | 2/2021 |
| CN | 213215683 U | 5/2021 |
| CN | 112971751 A | 6/2021 |
| CN | 113080904 A | 7/2021 |
| CN | 113142758 A | 7/2021 |
| CN | 113143234 A | 7/2021 |
| CN | 113273984 A | 8/2021 |
| CN | 113349747 A | 9/2021 |
| CN | 113520357 A | 10/2021 |
| CN | 113520358 A | 10/2021 |
| CN | 214317214 U | 10/2021 |
| CN | 113739986 A | 12/2021 |
| JP | 2000244991 A | 9/2000 |
| JP | 2002035066 A | 2/2002 |
| JP | 2008086529 A | 4/2008 |
| KR | 100235532 B1 | 12/1999 |
| KR | 101951917 B1 | 4/2019 |
| KR | 102311560 B1 | 10/2021 |
| TW | M543073 U | 6/2017 |
| WO | 9930612 A1 | 6/1999 |
| WO | 0039765 A1 | 7/2000 |
| WO | 2008124978 A1 | 10/2008 |
| WO | 2011127918 A1 | 10/2011 |
| WO | 2011145364 A1 | 11/2011 |
| WO | 2014001789 A1 | 1/2014 |
| WO | 2016097821 A1 | 6/2016 |
| WO | 2016198904 A1 | 12/2016 |
| WO | 2017173436 A1 | 10/2017 |
| WO | 2018139150 A1 | 8/2018 |
| WO | 2019128768 A1 | 7/2019 |
| WO | 2021112922 A1 | 6/2021 |
| WO | 2021147664 A1 | 7/2021 |
| WO | 2021190377 A1 | 9/2021 |
| WO | 2021190599 A1 | 9/2021 |
| WO | 2021203921 A1 | 10/2021 |
| WO | 2021208679 A1 | 10/2021 |
| WO | 2021213071 A1 | 10/2021 |
| WO | 2021213170 A1 | 10/2021 |
| WO | 2021229276 A1 | 11/2021 |
| WO | 2022133222 A1 | 6/2022 |
| WO | 2023004186 A1 | 1/2023 |
| WO | 2023200987 A1 | 10/2023 |
| WO | 2023230589 A1 | 11/2023 |
| WO | 2024050266 A1 | 3/2024 |

OTHER PUBLICATIONS

Youtube, "Getting Energized with Acupressure & Diet—Dr. Suzanna M. Zick at National Cancer Survivors Day Video", https://www.youtube.com/watch?v=sArsCf4Pkk4, 2017, 2 pages.

Youtube, "Headaches . . . ? Eye Massager Entered the Chat! Renpho Eye Massager Review Video", Jul. 7, 2022, 2 pages.

Youtube, "Renpho Shiatsu Eye Massager with Heat Air Compression and Bluetooth Music Video", 2020, 3 pages.

ZD Net, "Microsoft Patent Shows Wearable Band with Haptic Feedback", https://www.zdnet.com/article/microsoft-filed-a-patent-for-a-haptic-wearable-muscle-stimulator/; pages of website downloaded on Oct. 19, 2020; 8 pages <https://vault.netvoyage.com/neWeb2/goid.aspx?id=4819-9273-4927>.

Zhao, Jiangqi et al. "A Fully Integrated and Self-Powered Smartwatch for Continuous Sweat Glucose Monitoring", ACS Sens., vol. 4, 2019, pp. 1925-1933.

Zick, ND, MPH, Suzanna Maria et al., "Acupressure for Cancer-Fatigue in Ovarian Cancer Survivor (The AcuOca Study): A Community-Based Clinical Trial Study Protocol Examining the Impact of Self-Acupressure on Persistant Cancer Related Fatigue in Ovarian Cancer Survivors", University of Michigan, Elsevier, 2021, 37 pages.

Liu, Zeng-Ding et al., "Cuffless Blood Pressure Estimation Using Pressure Pulse Wave Signals", Sensors, vol. 18, 2018, 15 pages.

Ludeberg, T. et al., "Pain Alleviation by Vibratory Stimulation", Pain, vol. 20, 1984, pp. 25-44.

Machine-assisted English language abstract and machine-assisted English translation for CN 113349747 A extracted from espacenet.com database on Jan. 18, 2022, 31 pages.

Machine-assisted English language abstract and machine-assisted English translation for CN 113739986 A extracted from espacenet.com database on Jan. 18, 2022, 26 pages.

Machine-assisted English language abstract and machine-assisted English translation for CN 214317214 U extracted from espacenet.com database on Jan. 18, 2022, 22 pages.

Machine-assisted English translation for TWM 543073 U extracted from espacenet.com database on Apr. 20, 2022, 6 pages.

Mattsson, Adam et al., "Vibraaesthetics of Music—The Design of Beathoven: a Haptic Device of Enjoying Music Through Vibrotactile

(56) References Cited

OTHER PUBLICATIONS

Sensations", Lulea University of Technology, Industrial Design Engineering, Master's Level, 2021, 106 pages.

Men's Health, "Meet the Vibrating Wristband That Claims to Reduce Stress in Seconds", https://www.menshealth.com/health/a19530192/this-wristband-reduces-stress/#:~:text=But%20a%20brand%20called%20TouchPoints,the%20brain's%20response%20to%20stress <https://www.menshealth.com/health/a19530192/this-wristband-reduces-stress/>; pages of website downloaded on May 11, 2021; 5 pages.

NCBI, "Local Application of Vibratin in Motor Rehabilitation—Scientific and Practical Considerations", https://www.ncbi.nlm.nih.gov/pmc/articles/PMC5486165/; pages of website downloaded on Oct. 16, 2020; 7 pages <https://vault.netvoyage.com/neWeb2/goid.aspx?id=4831-0617-2879>.

Nexquest, "Nexquest Website", https://nexquest.com/; pages of website downloaded on Oct. 16, 2020; 5 pages <https://vault.netvoyage.com/neWeb2/goid.aspx?id=4828-1951-9439>.

Nomisk, "Maia Massager Webpage", https://nomisk.com/products/maia?tw_source=google&tw_adid=552654779945&tw_campaign=14934575409&gclid=Cj0KCQjwtsCgBhDEARIsAE7RYh0Wvv77DO9_7poiBR0ZGITz_1G8CQFIOHgVn1rNwTNej-_Xy--eLAlaAiv6EALw_wcB, 2023, 11 pages.

Novasentis: Haptic Wristbands for Smartwatches, Glassninja, published at least before Jan. 8, 202.

OCAD, "Body-Centric Technologies; Category 5: Workshop Notes 5—Expressive Haptic Throw Blanket" http://blog.ocad.ca/wordpress/digf6044-fw201803-01/category/workshop-notes-5/; pages of website downloaded on Oct. 16, 2020; 101 pages <https://vault.netvoyage.com/neWeb2/goid.aspx?id=4843-9933-0255>.

Omron Healthcare, Inc., "HeartGuide Wrist Blood Pressure Monitor Model BP8000-M Instruction Manual", 2019, 72 pages.

Pain Care Labs, "VibraCool Webpage", https://paincarelabs.com/pages/vibracool 2021, 13 pages.

Paredes, Pablo Enrique et al., CalmMeNow: Exploratory Research and Design of Stress Mitigating Mobile Interventions, Proceedings of the International Conference on Human Factors in Computing Systems, CHI 2011 Work-in-Progress, Extended Abstracts Volume, pp. 1699-1704, Vancouver, BC, Canada, <https://vault.netvoyage.om/neWeb2/goid.aspx?id=4825-8367-6101>.May 7-12, 2011; 6 pages.

Percardium 6 Image; published at least before Jan. 8, 2020, 1 page <https://vault.netvoyage.com/neWeb2/goid.aspx?id=4849-8281-7989>.

Philip Stein, "Natural Frequency Watches & Natural Frequency Bracelets", https://philipstein.com/; pages of website downloaded on Oct. 16, 2020; 12 pages <https://vault.netvoyage.com/neWeb2/goid.aspx?id=4845-0641-5055>.

Pournot, Herve et al., "The Acute Effect of Local Vibration as a Recovery Modality from Exercise_Induced Increased Muscle Stiffness", J Sports Sci Med, vol. 15, No. 1, Feb. 23, 2016, pp. 142-147; https://www.ncbi.nlm.nih.gov/pmc/articles/PMC4763833/; pages of website downloaded on Oct. 19, 2020; 12 pages <https://vault.netvoyage.com/neWeb2/goid.aspx?id=4831-1431-7263>.

PR Web, "New Reliefband Wearable Devices Unveiled at CES 2020 Expand Innovative Lineup of Nausea Prevention Products", 2020, 4 pages.

Practical Pain Management (PPM), "Vibration for Chronic Pain", https://www.practicalpainmanagement.com/treatments/rehabilitation/vibration-chronic-pain; pages of website downloaded on Oct. 16, 2020; 13 pages <https://vault.netvoyage.com/neWeb2/goid.aspx?id=4816-8364-8463>.

Precision Microdrives, "How to Drive a Vibration Motor With Arduino and Genuino", https://www.precisionmicrodrives.com/content/how-to-drive-a-vibration-motor-with-arduino-and-genuino/; pages of website downloaded on Oct. 19, 2020; 7 pages <https://vault.netvoyage.com/neWeb2/goid.aspx?id=4836-4850-1711>.

Pulse Band Clip published at least before Jan. 8, 2020; 1 page <https://vault.netvoyage.com/neWeb2/goid.aspx?id=4812-2478-7141>.

Relief Band Technologies LLC, "Relief Band 2.0", published at least before Jan. 8, 2020; 1 page <https://vault.netvoyage.com/neWeb2/goid.aspx?id=4822-4819-7317>.

Renpho, "Renpho Shiatsu Eye Massager with Heat, Air Compression, and Bluetooth Music", https://renpho.com/products/renpho-shiatsu-eye-massager, 2020, 9 pages.

Rosello, Oscar, "HeartBit: Mindful Control of Heart Rate Using Haptic Biofeedback", Massachusetts Institute of Technology, Feb. 2020, 69 pages.

Schreurs, B.G. et al., "Classical Conditioning of the Rabbit's Nictating Membrane Response to a Piezoceramic Vibrotactile CS", Behavior Research Methods, Intruments, & Computers, vol. 18, No. 4, 1986, pp. 359-362.

Sea Band, "Sea Band Product Webpage", https://www.sea-band.com/; pages of website downloaded on Oct. 19, 2020; 8 pages <https://vault.netvoyage.com/neWeb2/goid.aspx?id=4833-4821-5759>.

Sea Products, "SEA Bands: SEA Bands Relieve Motion Sickness by Applying Pressue on the P6 Acupressure Point on the Under Side of Your Wrist", https://www.seaproductsonline.com/SEA-Bands-SEA-Bands-relieve-motion-sickness-by-applying-pressure-on-the-P6-acupressure-point-on-the-under-side-of-your-wrist-_p_183.html; pages of website downloaded on Oct. 19, 2020; 2 pages <https://vault.netvoyage.com/neWeb2/goid.aspx?id=4837-6908-7951>.

Segman, Yosef (Joseph), "New Method for Computing Optical Hemodynamic Blood Pressure", J. Clin. Exp. Cardiolog., vol. 7, No. 12, 2016, 7 pages.

Sense Relief, "Sense Relief Application Webpage", https://sensereliefapp.com/, 2022, 4 pages.

Solà, Josep; Proena, Martin; Braun, Fabian; Pierrel, Nicolas; Degiorgis, Yan; Verjus, Christophe; Lemay, Mathieu; Bertschi, Mattia; and Schoettker, Patrick, Continuous non-invasive monitoring of blood pressure in the operating room: A cuffless optical technology at the fingertip, Current Directions in Biomedical Engineering, BMT2016—"Dreiländertagung" Swiss, Austrian and German Societies of Biomedical Engineering, vol. 2, Issue 1, Oct. 2016, pp. 267-271, De Gruyter, Switzerland.

Therabody, Inc., "Theragun Pro Plus Webpage", https://www.therabody.com/US/en-US/theragun-proplus.html, 2023, 9 pages.

Touchpoint, "Wear Calm website", https://thetouchpointsolution.com/; pages of website downloaded on May 11, 2021, 7 pages.

TWM image published at least before Jan. 8, 2020; 1 page <https://vault.netvoyage.com/neWeb2/goid.aspx?id=4840-9369-1077>.

U.S. National Library of Medicine, "Wearable Emotion Prosthetics for Post Traumatic Stress Disorder (EP-PTSD)", https://clinicaltrials.gov/ct2/show/NCT03529981, Jan. 13, 2021, 11 pages.

Umair, Muhammad et al., "Exploring Personalized Vibrotactile and Thermal Patterns for Affect Regulation", Virtual Event, USA, DIS, 2021, 24 pages.

U.S. Appl. No. 16/984,222, filed Aug. 4, 2020.

U.S. Appl. No. 17/577,890, filed Jan. 18, 2022.

Wang, Michael T.M. et al., "Abstract of Randomised Trial of the Clinical Utility of an Eyelid Massage Device for the Management of Meibomian Gland Dysfunction", Cont Lens Anterior Eye, vol. 42, No. 6, 2019, pp. 620-624.

WAT Medical Enterprise Ltd., EmeTerm Sea Sickness bands clip published at least before Jan. 8, 2020.

Waveform Gernerators, "555 Timer Tutorials", https://www.electronics-tutorials.ws/waveforms/555_timer.html; pages of website downloaded on Oct. 19, 2020; 19 pages <https://vault.netvoyage.com/neWeb2/goid.aspx?id=4842-4946-6063>.

Waveforms published at least before Jan. 8, 2020; 1 page <https://vault.netvoyage.com/neWeb2/goid.aspx?id=4839-7611-9493>.

Wigram, Anthony Lewis, "The Effects of Vibroacoustic Therapy on Clinical and Non-Clinical Populations", Thesis Submitted for the Degree of Doctor of Philosophy, St. Georges Hospital Medical School, London University, 1996, 290 pages.

(56) References Cited

OTHER PUBLICATIONS

Wikipedia, "Silicone Rubber Keypad", https://en.wikipedia.org/wiki/Silicone_rubber_keypad; pages of website downloaded on Oct. 19, 2020; 3 pages <https://vault.netvoyage.com/neWeb2/goid.aspx?id=4850-9014-5487>.
Wiorek, Alexander et al., "Epidermal Patch with Glucose Biosensor: pH and Temperature Correction Toward More Accurate Sweat Analysis During Sport Practice", Analytial Chemistry, vol. 92, 2020, 9 pages.
Yamane, Takahiro et al., "Simple Wearable Device to Reduce Stress When Delivering a Speech Without Pre-Training", The Korean Society of Medical Informatics, 2021, 10 pages.
Youtub, "Renpho Eye Massager Reviews", https://www.youtube.com/results?search_query=renpho+eye+massager+reviews, 2020, 7 pages.
Youtube, "Breo iSee4 vs. Renpho Eye Massager Video", https://www.youtube.com/watch?v=kgWLp-Mrxrw, 2021, 2 pages.
Youtube, "Does This Thing Work? Renpho Eye Massager Review Video", https://www.youtube.com/watch?v=kDivgRIStaQ, 2021, 2 pages.
International Search Report for Application No. PCT/US2023/014896 dated Nov. 6, 2023, 1 page.
Acu First Clip Image, published at least before Jan. 8, 2020; 1 page <https://vault.netvoyage.com/neWeb2/goid.aspx?id=4813-7571-6549>.
Amazon, "Acuressure SCAT Motion-Aid Wrist Straps w/Magnets from AME", https://www.amazon.com/exec/obidos/ASIN/B000K5ONQ2/26090703msg-20/; pages of website downloaded on Oct. 19, 2020; 7 pages <https://vault. netvoyage.com/neWeb2/goid. aspx?id=4821-6895-9695>.
Amazon, Band for Motion Sickness (i-Trans Wristband DM-800 Hivox), https://www.amazon.com/Motion-Sickness-i-Trans-Wristband-DM-800/dp/B002ECWTKQ; pages of website downloaded on Oct. 16, 2020; 7 pages <https://vault.netvoyage.com/neWeb2/goid.aspx?id=4840-4202-6703>.
Amazon, "Bioband Motion Sickness Band Black", https://www.amazon.com/exec/obidos/ASIN/B001KN5790/26090703msg-20/; pages of website downloaded on Oct. 19, 2020; 8 pages <https://vault.netvoyage.com/neWeb2/goid.aspx?id=4833-1059-6815>.
Amazon, "EmeTerm Relieve Nausea Electrode Stimulator", https://www.amazon.com/dp/B07LFXLV5J/ref=vp_d_pb_TIER2_trans_Ip_B07B84TZ6Z_pd?_encoding=UTF8&pd_rd_i=B07LFXLV5J&pd_rd_w=pAJIQ&pf_rd_p=e97d49af- c67a-4ec8-8fd9-01 d649d9c891&pf_rd_r=4c2b3f49-a49b-49e1 -96fa-0ca7234f0356&pd_rd_r=4c2b3f49- a49b-49e1-96fa-0ca7234f0356&pd_rd_wg=hV1 bq; pages of website downloaded on Oct. 19, 2020; 11 pages <https://vault.
Amazon, "Motion Cure Wristband", https://www.amazon.com/exec/obidos/ASIN/B018P6YX8U/26090703msg-20/; pages of website downloaded on Oct. 19, 2020; 9 pages <https://vault.netvoyage.com/neWeb2/goid.aspx?id=4830-5992-1615>.
Amazon, "NoMo Nausea Instant Relief Aromatherapy Anti-Nausea Bands with Acupressure", https://www.amazon.com/s?k=nomo+nausea+band&i=hpc&rh=n %3A3760901&linkCode=ll2&linkId=784bf82778438a3f266816a1ba30b4ef&tag=26090703msg-20&ref=as_li_ss_tl; pages of website downloaded on Oct. 19, 2020; 10 pages <https://vault.netvoyage.com/neWeb2/goid.aspx?id=4848-0639-0479>.
Amazon, "PSI Bands", https://www.amazon.com/stores/node/3039422011?_encoding=UTF8&field-lbr_brands_browse-bin=Psi%20Bands&linkCode=ll2&linkId=820afd077657430640cb993654a862d6&ref_=as_li_ss_tl&tag=26090703msg-20; pages of website downloaded on Oct. 19, 2020; 4 pages <https://vault.netvoyage.com/neWeb2/goid.aspx?id=4812-7301-7807>.
Amazon, "Reliefband Classic Anti-Nausea Writstband", https://www.amazon.com/dp/B07HCPYNXQ/ref=dp_cerb_3; pages of website downloaded on Oct. 16, 2020; 10 pages <https://vault.netvoyage.com/neWeb2/goid.aspx?id=4828-5459-7327>.
Amazon, "Reliefband Premier Motion Sickness Wristband", https://www.amazon.com/exec/obidos/ASIN/B07B84TZ6Z/26090703msg-20/; pages of website downloaded on Oct. 19, 2020; 8 pages <https://vault.netvoyage.com/neWeb2/goid.aspx?id=4848-0560-4047>.
Amazon, "Renpho Eye Massager with Heat, Bluetooth Music Heated Eyeris 1 Massager for Migraines, Relax and Reduce Eye Strain Dark Circles Eye Bags Dry Eye Improve Sleep, Ideal Gift", https://www.amazon.com/RENPHO-Massager-Compression-Bluetooth-Rechargeable/dp/B07SM61FCT/ref=sr_1_4?crid=Q6B7L0D439Y0&keywords=eye%2Bmassager&qid=1677542344&s=hpc&sprefix=eye%2Bmassager%2Chpc%2C107&sr=1-4&ufe=app_do%3Aamzn1.fos.08f69ac3-fd3d-4b88-bca2-8997e41410bb&th=1, 1996-2023, 15 pages.
Amazon, "Wonder Healing Motion Sickness Nausea Relief Wristbands", https://www.amazon.sg/Wristbands-Acupressure-Anti-Nausea-Pregnancy-healing/dp/B07XJ7FV7D; pages of website downloaded on Oct. 19, 2020; 4 pages <https://vault.netvoyage.com/neWeb2/goid.aspx?id=4812-1298-7599>.
Apex Moon, "Wearable.com Website", <https://www.wearable.com/health-and-wellbeing/living-with-doppel-wearable-change-mood-7270>; pages of website downloaded on May 11, 2021; 3 pages.
Apollo, "90% of Children Experienced an Over 50% Reduction in Stress Scores, as Well as Improvements in Mood and Attention Control", https://apolloneuro.com/blogs/news/100-of-children-with-adhd-and-anxiety-experience-symptom-improvement-with-apollo-in-pilot-study, Apr. 17, 2020, 5 pages.
Apollo, "Apollo Improves Recovery and Performance in Elite Athletes", https://apolloneuro.com/blogs/news/apollo-improves-recovery-and-performance-in-athletes, Aug. 20, 2021, 4 pages.
Apollo, "Apollo Reduces Stress in Nursing Staff by 40% in Two Weeks", https://apolloneuro.com/blogs/news/apollo-reduces-stress-in-nursing-staff-by-40-in-two-weeks, Oct. 13, 2019, 3 pages.
Apollo, "Apollo Studies for PTSD Are Underway", https://apolloneuro.com/blogs/news/apollo-studies-for-ptsd-are-underway, Oct. 13, 2019, 3 pages.
Apollo, "Clinical Study Validates that Apollo Improves Cognitive Performance and Heart Rate Variability (HRV)", https://apolloneuro.com/blogs/news/clinical-study-validates-that-apollo-improves-cognitive-performance-and-heart-rate-variability-hrv, Jan. 20, 2020, 5 pages.
Apollo, "Life Can Be Chaotic. Apollo is Here to Help", https://web.archive.org/web/20191216155436/https://shop.apolloneuro.com/, 2019, 10 pages.
Apollo, "Preliminary Apollo Sleep Study Results Are In", https://apolloneuro.com/blogs/news/apollo-neuro-sleep-study-is-underway, Sep. 29, 2021, 6 pages.
Apollo, "Research Study Shows EEG Similarity Between Apollo Neuro Users and Experienced Meditators", https://apolloneuro.com/blogs/news/can-apollo-neuro-make-meditation-easier, May 27, 2021, 4 pages.
Apple, "Sense Relief App", https://apps.apple.com/US/app/sense-relief/id1457764420; pages of website downloaded on Oct. 16, 2020; 3 pages <https://vault.netvoyage.com/neWeb2/goid.aspx?id=4846-0780-0271>.
Applie, "Apple Watch Series 5 Smartwatch clip", published at least before Jan. 8, 2020; 1 page <https://vault.netvoyage.com/neWeb2/goid.aspx?id=4817-2154-6959>.
Arduino, "Arduino Program—VibrationMotor PWM", published at least before Jan. 8, 2020; 1 page <https://vault.netvoyage.com/neWeb2/goid.aspx?id=4820-6358-2405>.
Ars Technica, "Hear the Pulse: Heart Rate Monitoring Fitness Earbuds Tested", https://arstechnica.com/ gadgets/2016/12/hear-the-pulse-heart-rate-monitoring-fitness-earbuds-tested/; pages of website downloaded on Oct. 16, 2020; 6 pages <https://vault.netvoyage.com/neWeb2/goid.aspx?id=4828-8184-4431>.
Auto Desk; indestructibles.com, "Haptic Interface Arduino Prototype", https://www.instructables.com/id/Haptic-Interface-Arduino-Prototype/; pages of website downloaded on Oct. 19, 2020; 7 pages <https://vault.netvoyage.com/neWeb2/goid.aspx?id=4814-4944-0719>.
Autodesk; indestructibles.com, "Pulse Sensor Wearable", https://www.instructables.com/id/Pulse-Sensor-Wearable/; pages of website downloaded on Oct. 19, 2020; 15 pages <https://vault.netvoyage.com/neWeb2/goid.aspx?id=4811-3257-4159>.

(56) References Cited

OTHER PUBLICATIONS

Azevedo, Ruben T. et al., "The Calming Effect of a New Wearable Device During the Anticipation of Public Speech", May 23, 2017, 7 pages.
Best Massage Chair Guide, "Vibration Massage: Its Positive Effects on Mind, Body, and Well-Being", https://bestmassagechairguide.com/vibrational-massage-and-its-positive-effects-on-your-body/; pages of website downloaded on Oct. 16, 2020; 8 pages <https://vault.netvoyage.com/neWeb2/goid.aspx?id=4818-3647-7903>.
Bioniva Wellness International, "Bionica Painless Wearable Well-Being Pendant Webpage", https://www.bioniva.com/therapeutic-devices/, 2018, 10 pages.
Blisslets, "Blisslets Product Webpage", https://myblisslets.com/; pages of website downloaded on Oct. 19, 2020; 15 pages <https://vault.netvoyage.com/neWeb2/goid.aspx?id=4828-1501-3583>.
Born to Invent, "The 555 Timer", https://www.bournetoinvent.com/projects/gcse_theory/4.html; pages of website downloaded on Oct. 19, 2020; 5 pages <https://vault.netvoyage.com/neWeb2/goid.aspx?id=4818-5609-0831>.
Breo, "Breo iSee4 Eye Massager Webpage", https://us.breo.com/products/breo-isee4-eye-massager, 2023, 7 pages.
CarpalRx, "CarpalRx Webpage", https://www.carpalrx.com/myofascial-release-massage-carpal-tunnel, 2022, 6 pages.
Castaneda, Denisse et al., "A Review on Wearable Photoplethysmography Sensors and Their Potential Futrue Applicatons ion Health Care", Int J. Bioelectron., vol. 4, No. 4, 2018, pp. 195-202, https://www.ncbi.nlm.nih.gov/pmc/articles/PMC6426305/; pages of website downloaded on Oct. 19, 2020; 19 pages <https://vault.netvoyage.com/neWeb2/goid.aspx?id=4821-5401-8767>.
Chinavasion, "P6 Smart Bracelet Heart Rate Blood Pressure Waterproof Smart Watch Webpage", http://chinavasion.com/china/wholesale/electronics/smart-watch/android-watch/p6-smart-bracelet-heart-rate-blood-pres-pel-0dcdeyg5; pages of website downloaded on Oct. 16, 2020; 6 pages <https://vault.netvoyage.com/neWeb2/goid.aspx?id=4825-7434-9263>.
Choi, Kyung Yun et al., "aSpire: Clippable, Mobile Pneumatic-Haptic Device for Breathing Rate Regulation via Personalizable Tactle Feedback", 2021, 8 pages.
Colloca, L. et al., "The Role of Learning in Nocebo and Placebo Effects", Pain, vol. 136, 2008, pp. 211-218.
Cool Wearables, "NovaSentis: Haptic Wristbands for Smartwatches", https://www.coolwearable.com/novasentis-haptic-wristbands-for-smartwatches/; pages of website downloaded on Oct. 16, 2020; 5 pages <https://vault.netvoyage.com/neWeb2/goid.aspx?id=4844-9979-5407>.
Costa, Jean et al., "BoostMeUp: Improving Cognitive Performance in the Moment by Unobtrusively Regulating Emotions with a SmartWatch", Association for Computing Machinery, 2018, 23 pages.
Costa, Jean et al., "EmotionCheck: Leveraging Bodilty Signals and False Feedback to Regulate Our Emotions", 2016, 12 pages.
Creganna Tactx Medical, "Deflectable & Steerable Catheter Handbook-Terminology Guide & Design Options", 2022, 7 pages.
Doppel, "Product Guide", 2018, 45 pages.
Dougherty, Donald M., "Generalization of a Tactile Stimulus in Horses", Journal of the Experimental Analysis of Behavior, vol. 59, 1993, pp. 521-528.
Dual Vibration Motors, published at least before Jan. 8, 2020; 1 page <https://vault.netvoyage.com/neWeb2/goid.aspx?id=4835-3479-7007>.
Durand, E. et al., "Plasticity in Respiratory Motor Control Selected Contriubtion: Classical Conditioning of Breathing Pattern After Two Acquisistion Trials in 2-day-old Mice", J. Apl Physiol, vol. 94, 2003, pp. 812-818.
Engadget, "Website", <https://www.engadget.com/apollo-neuro-stress-relief-wearable-155545997.html>; pages of website downloaded on May 11, 2021, 8 pages.
English language abstract and machine-assisted English language translation of Chinese Patent No. CN 106333667 A extracted from www.espacenet.com database on Dec. 29, 2020, 99 pages.
English language abstract and machine-assisted English translation for CN 107129690 B extracted from espacenet.com database on Mar. 14, 2023, 21 pages.
English language abstract and machine-assisted English translation for CN 107349092 A extracted from espacenet.com database on Apr. 20, 2022, 8 pages.
English language abstract and machine-assisted English translation for CN 107349093 A extracted from espacenet.com database on Apr. 20, 2022, 9 pages.
English language abstract and machine-assisted English translation for CN 11271751 A extracted from espacenet.com database on Jan. 18, 2022, 25 pages.
English language abstract and machine-assisted English translation for CN 113080904 A extracted from espacenet.com database on Jan. 18, 2022, 18 pages.
English language abstract and machine-assisted English translation for CN 113142758 A extracted from espacenet.com database on Jan. 18, 2022, 38 pages.
English language abstract and machine-assisted English translation for CN 113143234 A extracted from espacenet.com database on Jan. 18, 2022, 16 pages.
English language abstract and machine-assisted English translation for CN 113273984 A extracted from espacenet.com database on Jan. 18, 2022, 28 pages.
English language abstract and machine-assisted English translation for CN 113520357 A extracted from espacenet.com database on Jan. 18, 2022, 30 pages.
English language abstract and machine-assisted English translation for CN 113520358 A extracted from espacenet.com database on Jan. 18, 2022, 31 pages.
English language abstract and machine-assisted English translation for CN 210019307 U extracted from espacenet.com database on Jan. 18, 2022, 9 pages.
English language abstract and machine-assisted English translation for CN 210673734 U extracted from espacenet.com database on Mar. 14, 2023, 15 pages.
English language abstract and machine-assisted English translation for CN 210932663 U extracted from espacenet.com database on Mar. 14, 2023, 8 pages.
English language abstract and machine-assisted English translation for CN 211934039 U extracted from espacenet.com database on Jan. 18, 2022, 32 pages.
English language abstract and machine-assisted English translation for CN 212489876 U extracted from espacenet.com database on Jan. 18, 2022, 18 pages.
English language abstract and machine-assisted English translation for CN 212574862 U extracted from espacenet.com database on Jan. 18, 2022, 32 pages.
English language abstract and machine-assisted English translation for CN 213215683 U extracted from espacenet.com database on Jan. 18, 2022, 38 pages.
English language abstract and machine-assisted English translation for JP 2002-035066 A extracted from espacenet.com database on Mar. 14, 2023, 8 pages.
English language abstract and machine-assisted English translation for KR 101951917 B1 extracted from espacenet.com database on Mar. 14, 2023, 10 pages.
English language abstract and machine-assisted English translation for KR 102311560 B1 extracted from espacenet.com database on Mar. 14, 2023, 14 pages.
English language abstract and machine-assisted English translation for WO 2018/139150 A1 extracted from espacenet.com database on Mar. 14, 2023, 31 pages.
English language abstract and machine-assisted English translation for WO 2019/128768 A1 extracted from espacenet.com database on Jan. 18, 2022, 16 pages.
English language abstract and machine-assisted English translation for WO 2021/147664 A1 extracted from espacenet.com database on Jan. 18, 2022, 39 pages.
English language abstract and machine-assisted English translation for WO 2021/190377 A1 extracted from espacenet.com database on Jan. 18, 2022, 30 pages.

(56) References Cited

OTHER PUBLICATIONS

English language abstract and machine-assisted English translation for WO 2021/190599 A1 extracted from espacenet.com database on Jan. 18, 2022, 59 pages.
English language abstract and machine-assisted English translation for WO 2021/203921 A1 extracted from espacenet.com database on Jan. 18, 2022, 31 pages.
English language abstract and machine-assisted English translation for WO 2021/208679 A1 extracted from espacenet.com database on Jan. 18, 2022, 32 pages.
English language abstract and machine-assisted English translation for WO 2021/213071 A1 extracted from espacenet.com database on Jan. 18, 2022, 30 pages.
English language abstract and machine-assisted English translation for WO 2021/213170 A1 extracted from espacenet.com database on Jan. 18, 2022, 25 pages.
English language abstract for International Patent Publication No. WO 99/30612 and machine-assisted English translation of equivalent Russian Federation Patent No. RU 2141250 extracted from www.espacenet.com database on Nov. 2, 2020; 6 pages.
English language abstract for WO 2011/127918 A1 extracted from espacenet.com database on Mar. 14, 2023, 2 pages.
Flanigan, Tara, "These Vibrating Wristbands Claim to Melt Stress Way in Just 30 Seconds", <https://mashable.com/2017/08/14/vibrating-stress-wearable-relieve/>; Aug. 14, 2017, 7 pages.
Frey, Jeremy et al., "Breeze: Sharing Biofeedback Through Wearable Technologies", Ubiquitous Computing Lab, Interdisciplinary Center, Israell, France, 2018, 12 pages.
Google Play, "MeTime Acupressure Application Information", https://play.google.com/store/apps/details?id=edu.umich.metime&hl=en, 2023, 3 pages.
Google, "Flat Capacitors", https://www.google.com/search?q=flat+capacitors&rlz=1 C1 CHBF_enUS874US874&oq=flat +capacitors&aqs=chrome..69i57jOI5.3473jOj8&sourceid=chrome&ie=UTF-8; pages of website downloaded on Oct. 19, 2020; 3 pages <https://vault.netvoyage.com/neWeb2/goid.aspx?id=4840-6648-9551>.
Google, "Seaband With Haptics", https://www.google.com/search?q=sea+band+with+haptics&tbm=isch&ved=2ahUKEwjbocjT-8DsAhXMAN8KHe5eDtEQ2-cCegQIABAA&oq=sea+band+with+haptics&gs_Icp=CgNpbWcQAzIECCMQJ1DFPVjFPWCLSGgAcAB4AIABSIgBSJIBATGYAQCgAQGqAQtnd3Mtd2I6LWItZ8ABAQ&sclient=img&ei=-q-NX9u8BsyB_AbuvbmIDQ&bih=96+9&biw=1920&rlz=1+C1+CHBF+enUS874US874; pages of website downloaded on Oct. 19, 2020; 2 pages <https://vault.netvoyage.com/neWeb2/goid.aspx?
Haddad, Serj et al., "Continuous PPG-Based Blood Pressure Monitoring Using Multi-Linear Regression", 2020, 9 pages.
Haining Beyond Seals Co., Ltd, "DN 10 mm Black Color Silicone Push Button Cover for Power Key Switch" http://www.molded-rubberseals.com/sale-11816310-dn-10-mm-black-color-silicone-push-button-cover-for-power-key-switch.html; pages of website downloaded on Oct. 16, 2020; 4 pages <https://vault.netvoyage.com/neWeb2/goid.aspx?id=4813-5138-1967>.
Hosanee, Manish et al., "Cuffless Single-Site Photoplethysmography for Blood Pressure Monitoring", Journal of Clinical Medicine, 2020, 14 pages.
Indiegogo, "WrisLax-Wearable Wrist Massager & Sleeping Help Webpage", https://www.indiegogo.com/projects/wrislax-wearable-wrist-massager-sleeping-help#/, 2023, 5 pages.
Inner Solutions, "Creating Quality Vibroacoustic Sound Tables for Over 20 Years", https://innersoulutions.com/faqs/; pages of website downloaded on Oct. 16, 2020; 8 pages <https://vault.netvoyage.com/neWeb2/goid.aspx?id=4830-4830-4079>.
Instagram, "Neosensory", Dec. 6, 2019, 1 page.
Interaxan, "Muse Devices Webpage", https://choosemuse.com/?utm source=google&utm medium=cpc&utmcampaign=BoF USA Search Brand&utm term=muse--e&utm_content=Brand_Name443962996222&gclid=Cj0KCQjw6uT4BRD5ARIsADwJQ1884JE4EjSS1aMYPhaiHDu-iaqOtX74WpyTtZtcUIg9D4gsYqLTbosaAk4REALw_wcB; pages of website downloaded on Oct. 16, 2020; 9 pages <https://vault.netvoyage.com/neWeb2/goid.aspx?id=4825-1831-6239>.
Interaxan, "Muse Guided Meditation Bundle Webpage", https://choosemuse.com/muse-s-guided-bundle/?gclid=CJ0KCQjwuJz3BRDTARIsAMg-HxVO_OCiMfrIDLDL8eTIssNH6VhV-ICVhKr4YdRrRfwAMaeej91Mwt4aAwaEALw_wcB; pages of website downloaded on Oct. 16, 2020; 7 pages <https://vault.netvoyage.com/neWeb2/goid.aspx? id=4825-1831-6239>.
Joicom Corporation, "Renpho Model: SD-002 Electric Eye Massager User Manual", 2019, 16 pages.
Kelling, Chelsea et al., "Good Vibes: The Impact of Haptic Patterns on Stress Levels", Conference Paper, Academic Mindtrek, 2016, 8 pages.
Kirmayer, MD, Laurence J., "Unpacking the Placebo Response: Insights from Ethnographic Studies of Healing", The Journal of Mind_Body Regulation, vol. 1, No. 3, 2011, 13 pages.
Koheel, "Koheel Wearable Device for Headache, Migraine, Tenision Relief—Support Acupressure Relaxation, Stress Alleviation, Soothing Muscle Pain Webpage", https://www.koheel.com/products/wearable-device-for-headache-migraine-tension-relief, 2023, 4 pages.
Kozin, Gene, Livongo—How Do Blood Pressure Monitors Work?: , https://techblog.livongo.com/how-do-blood-pressure-monitors-work/; pages of website downloaded on Oct. 19, 2020; 6 pages <https://vault.netvoyage.com/neWeb2/goid.aspx?id=4847-4544-1999>.
Kozyackin, "Professor Kozyavkin Method_Vibratin Therapy Webpage", https://kozyavkin.com/en/treatment/rehab-components/content/vibration-therapy/; pages of website downloaded on Oct. 16, 2020; 5 pages <https://vault.netvoyage.com/neWeb2/goid.aspx?id=4830-8375-9311>.
Lee, Anna, Chan, Simon K.C., Fan, Lawrence T.Y., Stimulation of the wrist acupuncture point PC6 for preventing postoperative nausea and vomiting, pp. 3-137, Cochrane Database of Systematic Reviews 2015, Issue 11. Art. No. CD003281, 2016 The Cochrane Collaboration. Published by John Wiley & Sons, Ltd.
Linked In, "Dr. Grame Massagers", https://www.drgraeme.com/articles/2019/08/scientific-effects; pages of website downloaded on Oct. 19, 2020; 9 pages <https://vault.netvoyage.com/neWeb2/goid.aspx?id=4838-7938-4271>.
English language abstract and machine-assisted English language translation of CN 210228475 U extracted from www.espacenet.com database on Mar. 20, 2024, 10 pages.
English language abstract and machine-assisted English translation for CN 200970326 Y extracted from espacenet.com database on Mar. 22, 2024, 7 pages.
English language abstract and machine-assisted English translation for CN 210933465 U extracted from espacenet.com database on Mar. 22, 2024, 8 pages.
English language abstract and machine-assisted English translation for JP 2000-244991 A extracted from espacenet.com database on Mar. 22, 2024, 5 pages.
English language abstract and machine-assisted English translation for JP 2008-086529 A etracted from espacenet.com database on Mar. 22, 2024, 16 pages.
Machine-assisted English translation of Abstract for KR 10-0235532 B1 extracted from espacenet.com database on Mar. 22, 2024, 1 page.
English language abstract for WO 2008/124978 A1 extracted from espacenet.com database on Mar. 22, 2024, 2 pages.
English language abstract for WO 2011/145364 A1 extracted from espacenet.com database on Mar. 22, 2024, 2 pages.
"U.S. Appl. No. 17/929,571, filed Sep. 2, 2022", 975 pages.
Youtube, "Core Meditation Device Hands-On at CES Video", https://www.youtube.com/watch?v=iGEWCysChoc, 2020, 3 pages.
Youtube, "Core Meditation Trainer and Meditation App on QVC Video", https://www.youtube.com/watch?v=labUjT5grDA, 2022, 2 pages.
"U.S. Appl. No. 18/601,138, filed Mar. 11, 2024", 59 pages.
International Searching Authority, Written Opinion for International Application No. PCT/US2023/018547, 2024, 6 pages.
Ohio State University, "Easeband Webpage", 2019, 2 pages.
Therabody, "RecoveryAir JetBoots Manual", 2023, 24 pages.

(56) References Cited

OTHER PUBLICATIONS

Uspto, "Non-Final Office Action dated Nov. 21, 2023 for U.S. Appl. No. 17/588,570", 18 pages.

* cited by examiner

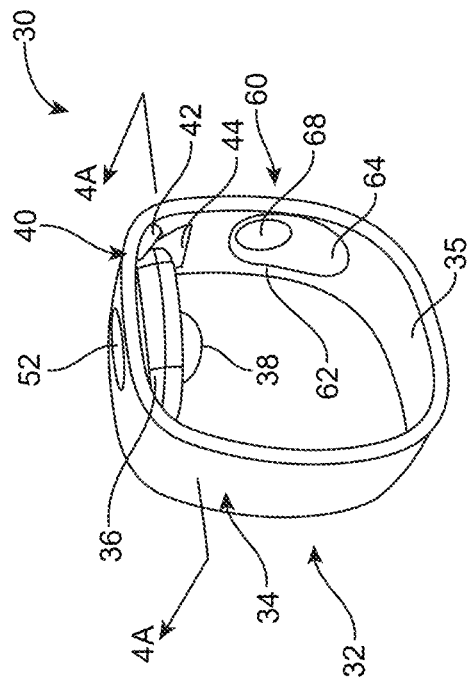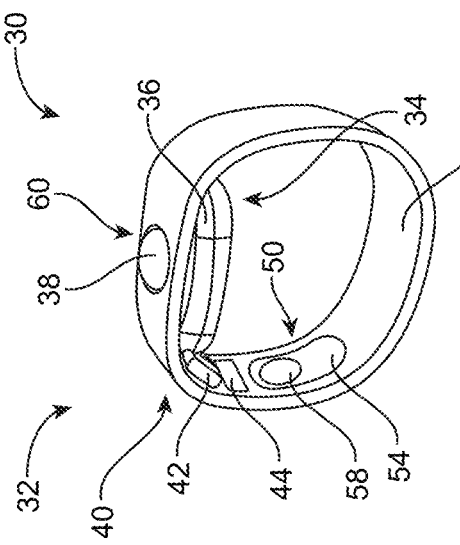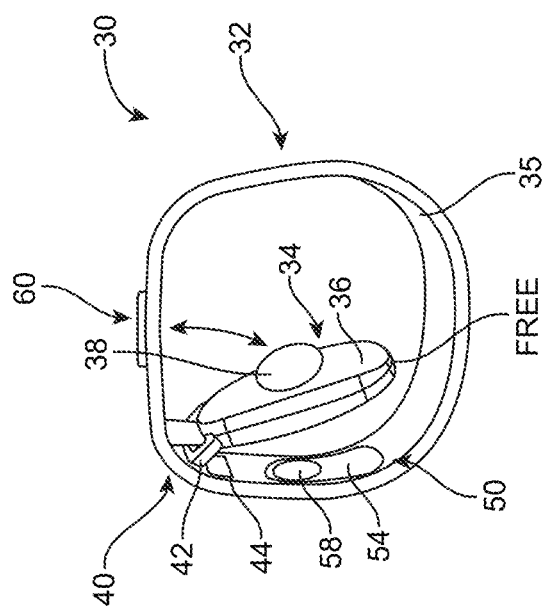

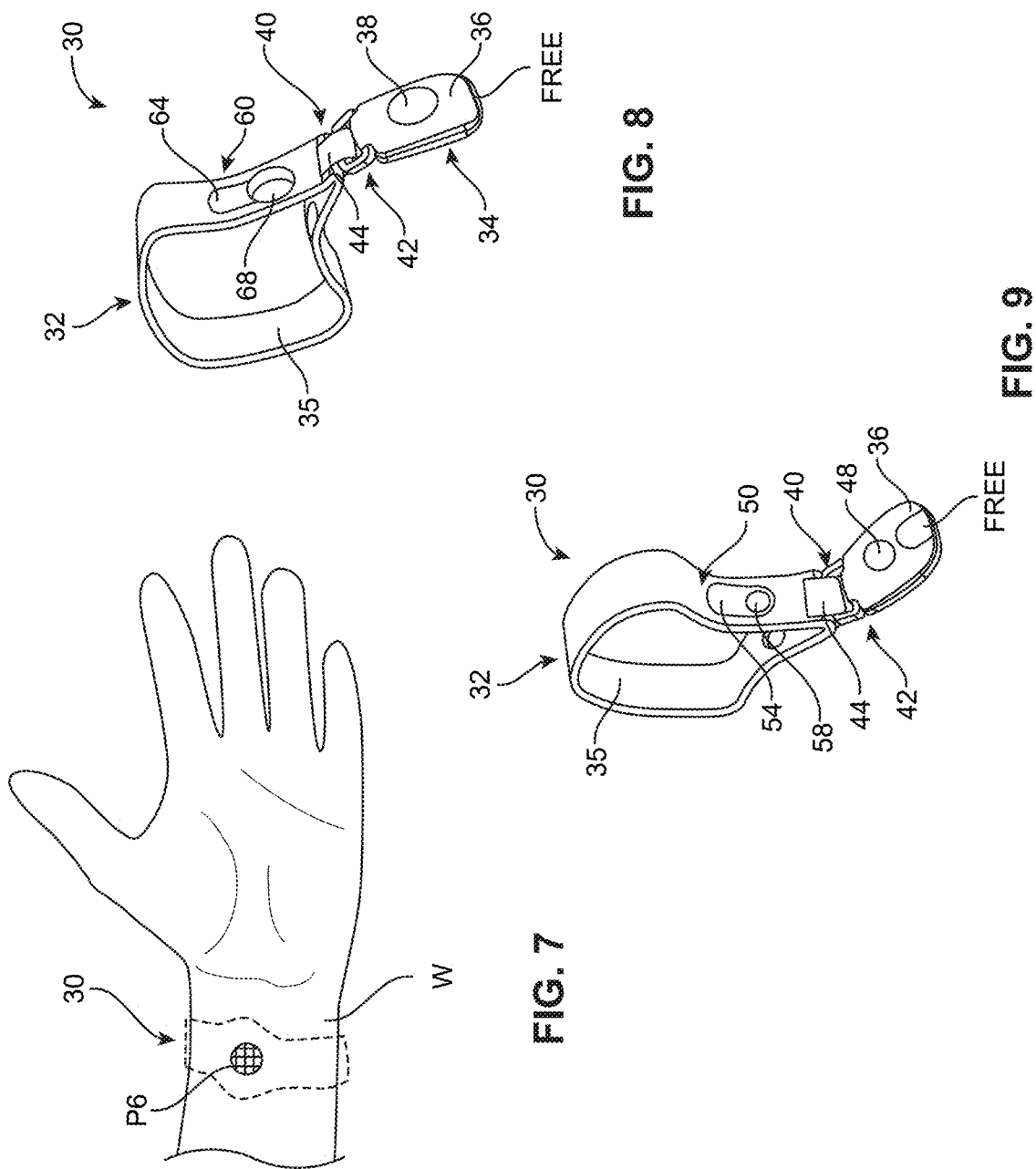

DEVICE FOR PROVIDING MULTIPLE TYPES OF THERAPY TO A USER

RELATED APPLICATIONS

This application is a continuation-in-part of International Application No. PCT/US2023/014896, filed on Mar. 9, 2023, which claims the benefit of U.S. Provisional Patent Application No. 63/318,591, filed on Mar. 10, 2022, U.S. Provisional Patent Application No. 63/333,595, filed on Apr. 22, 2022, U.S. Provisional Patent Application No. 63/408,564, filed on Sep. 21, 2022, U.S. Provisional Patent Application No. 63/415,007, filed on Oct. 11, 2022, U.S. Provisional Patent Application No. 63/421,602, filed on Nov. 2, 2022, and U.S. Provisional Patent Application No. 63/433,094, filed on Dec. 16, 2022, the disclosures of all of which are hereby incorporated herein by reference.

TECHNICAL FIELD

The present disclosure relates to devices, systems, and methods for providing therapy to a user and/or for measuring physiological parameters of the user.

BACKGROUND

Every day, more and more people are suffering from prolonged bouts of stress and anxiety. There is a need for alternative forms of therapy for such people to address their stress and anxiety, and to improve their stress resilience.

SUMMARY

In some embodiments, a device comprises one or more haptic generators, a user interface, and a housing. A projection is connectable to the housing and configured to provide haptic therapy to the user. A controller controls operation of the one or more haptic generators and enables the user to perform a combination of therapies with the device.

In some embodiments, a wearable device comprises a wearable support to be worn by the user and one or more haptic generators. A user interface activates the one or more haptic generators. A housing carries the one or more haptic generators. A projection protrudes from the housing to engage the user to provide therapy to the user. A hinge movably couples the housing to the wearable support. The housing has a free end configured to move relative to the wearable support between a first configuration and a second configuration. In the first configuration, the projection is directed toward the user to engage the user when the wearable support is worn by the user. In the second configuration, the projection is directed away from the user to avoid contact with the user when the wearable support is worn by the user.

In some embodiments, a wearable device comprises a band to be worn by a user and a housing movably coupled to the band. A projection extends from the housing to engage the user for therapy. A hinge couples the housing to the band. The housing has a hinged end coupled to the band and an opposing free end configured to swing relative to the band between a first configuration and a second configuration. In the first configuration, the projection is directed toward the user to engage the user when the band is worn by the user. In the second configuration, the projection is directed away from the user to avoid contact with the user when the band is worn by the user.

In some embodiments, a wearable device comprises a band to be worn by a user, one or more haptic generators, and a user interface. A projection engages the user. A controller is coupled to the user interface to control operation of the one or more haptic generators. The projection is movable to each of: (i) a first configuration in which the projection is directed toward the user when the band is worn by the user, wherein the controller enables the user to perform a combination of acupressure or massage therapy and haptic therapy by allowing the user to place the projection in contact with the user and thereafter activate the one or more haptic generators; (ii) a second configuration in which the projection is directed away from and out of contact with the user when the band is worn by the user, wherein the controller, in the second configuration, is configured to generate vibrations to be felt by the user; and (iii) a third configuration in which the band is reversed, wherein the controller, in the third configuration, is configured to generate vibrations to be felt by the user.

In some embodiments, a wearable device comprises a band to be worn by a user and one or more haptic generators. A user interface activates the one or more haptic generators. A housing carries the one or more haptic generators. A projection protrudes from the housing to engage the user to provide therapy to the user. The housing defines an opening to receive the projection such that the projection is movable relative to the housing when pressing the projection into the user. A controller and a force sensor operatively connected to the controller measure force exerted on the projection.

In some embodiments, a wearable device provides haptic therapy to a user. The wearable device comprises a wearable support to be worn by the user. One or more haptic generators are coupled to the wearable support. A controller coupled to a user interface is operable in a conditioning mode and a recall mode. The controller is configured to activate the one or more haptic generators using a predetermined haptic waveform to produce vibrations during each of a plurality of conditioning sessions in the conditioning mode in which the user performs a mind-body intervention, thereby pairing performance of the mind-body intervention and the vibrations to condition the user in the conditioning mode to associate the vibrations with the mind-body intervention. The controller is further configured to enable activation of the recall mode after conditioning the user in the conditioning mode thereby enabling the user to activate the one or more haptic generators using the predetermined haptic waveform to produce the vibrations in the recall mode to relax the user to a relaxed state from an elevated stress state.

In some embodiments, a wearable device provides haptic therapy to a user. The wearable device comprises a band to be worn by the user and one or more haptic generators. A housing encloses the one or more haptic generators. A projection protrudes from the housing. The housing is movably coupled to the band to move relative to the band between a first configuration in which the projection is directed toward the user to engage the user when the band is worn by the user and a second configuration in which the projection is directed away from the user to avoid contact with the user when the band is worn by the user. A controller is operable to control the one or more haptic generators, when the housing is in the first configuration, by activating the one or more haptic generators with a predetermined haptic waveform to produce vibrations during each of a plurality of acupressure sessions. The controller is also configured to activate the one or more haptic generators using the predetermined haptic waveform to relax the user when the housing is in the second configuration.

In some embodiments, a system comprises a wearable device and a smart device. The wearable device includes a wearable support to be worn by a user and one or more haptic generators to provide vibrational output to the user. A first controller is operable to activate the one or more haptic generators using a predetermined haptic waveform to generate vibrations to be felt by the user to haptically guide the user through multiple phases of a first breathing session. The smart device includes a display and a second controller capable of communication with the first controller. The second controller is operable, in a training mode, to visually guide the user through the multiple phases of the first breathing session using the display, while the first controller activates the one or more haptic generators using the predetermined haptic waveform. The first controller is also configured to haptically guide the user through multiple phases of a second breathing session, in a recall mode, by activating the one or more haptic generators using the predetermined haptic waveform, but without the second controller providing any visual guidance on the display to visually guide the user through the second breathing session.

In some embodiments, a wearable device comprises a wearable support to be worn by a first user. One or more haptic generators are coupled to the wearable support. A user interface activates the one or more haptic generators. A controller is operatively coupled to the user interface and a microphone. The controller is configured to activate the one or more haptic generators using voice-related data to generate vibrations felt by the first user, wherein the voice-related data is created from voice input received by the microphone from a second user. The voice input is converted to the voice-related data and stored in memory so that activation of the user interface by the first user generates the vibrations associated with the voice input of the second user.

In some embodiments, a wearable device is used by a first user and capable of communication with a smart device used by a second user. The wearable device comprises a wearable support to be worn by the first user. One or more haptic generators are coupled to the wearable support. A user interface activates the one or more haptic generators. A controller is operatively coupled to the user interface and configured to activate the one or more haptic generators using voice-related data to generate vibrations felt by the first user. The voice-related data is created from voice input from the second user using the smart device. The voice input is converted to the voice-related data and stored in memory so that activation of the user interface by the first user generates the vibrations associated with the voice input of the second user.

In some embodiments, a system provides haptic therapy to a first user. The system comprises a wearable device including a wearable support to be worn by the first user, one or more haptic generators coupled to the wearable support, a user interface to activate the one or more haptic generators; and a wearable controller configured to activate the one or more haptic generators to generate vibrations felt by the first user. A smart device is capable of communication with the wearable device. The smart device includes a smart controller, a microphone, and a software application running on the smart device. The smart controller is configured to receive voice input from a second user to create voice-related data such that the one or more haptic generators can be activated using the voice-related data to generate the vibrations to be felt by the user based on the voice input. The voice-related data is generated by the smart controller and transmitted to the wearable controller to be stored in memory connected to the wearable controller so that activation of the user interface by the first user generates the vibrations associated with the voice input.

In some embodiments, a wearable device comprises a wearable support to be worn by a user. One or more haptic generators are coupled to the wearable support. A user interface activates the one or more haptic generators. A controller is operatively coupled to the user interface and configured to activate the one or more haptic generators using haptic data to generate vibrations felt by the user. The haptic data is created from music, the music being converted to the haptic data and stored in memory so that activation of the user interface by the first user generates the vibrations associated with the music.

In some embodiments, a wearable device is used by a user and capable of communication with a smart device. The wearable device comprises a wearable support to be worn by the user. One or more haptic generators are coupled to the wearable support. A user interface activates the one or more haptic generators. A controller is operatively coupled to the user interface and configured to activate the one or more haptic generators using haptic data to generate vibrations felt by the user. The haptic data is created from music selected using the smart device, the music being converted to the haptic data and stored in memory so that activation of the user interface by the user generates the vibrations associated with the music.

In some embodiments, a system provides haptic therapy to a user. The system comprises a wearable device including a wearable support to be worn by the user, one or more haptic generators coupled to the wearable support, a user interface to activate the one or more haptic generators, and a wearable controller configured to activate the one or more haptic generators to generate vibrations felt by the user. The system also includes a smart device capable of communication with the wearable device. The smart device includes a smart controller and a software application running on the smart device. The smart controller is configured to create haptic data from music such that the one or more haptic generators can be activated using the haptic data to generate the vibrations to be felt by the user based on the music, wherein the haptic data is generated by the smart controller and transmitted to the wearable controller to be stored in memory connected to the wearable controller so that activation of the user interface by the user generates the vibrations associated with the music.

In some embodiments, a wearable device comprises a wearable support to be worn by a user and one or more haptic generators coupled to the wearable support. A user interface activates the one or more haptic generators. A controller is operatively coupled to the user interface and configured to activate the one or more haptic generators to generate vibrations felt by the user, wherein the vibrations are derived from an audio file of music so that activation of the user interface by the first user generates the vibrations associated with the music.

In some embodiments, a wearable device is capable of communication with a smart device. The wearable device comprises a wearable support to be worn by the user and one or more haptic generators coupled to the wearable support. A user interface activates the one or more haptic generators. A controller is operatively coupled to the user interface and configured to activate the one or more haptic generators to generate vibrations felt by the user, wherein the vibrations are derived from an audio file of music selected using the smart device, so that activation of the user interface by the user generates the vibrations associated with the music.

In some embodiments, a system provides haptic therapy to a user. The system comprises a wearable device including a wearable support to be worn by the user, one or more haptic generators coupled to the wearable support, a user interface to activate the one or more haptic generators, and a wearable controller configured to activate the one or more haptic generators to generate vibrations felt by the user. The system also comprises a smart device capable of communication with the wearable device. The smart device includes a smart controller and a software application running on the smart device, wherein the smart controller is configured to provide an audio file of music to the wearable device such that the one or more haptic generators can be activated to generate the vibrations to be felt by the user based on the music.

In some embodiments, a wearable device comprises a wearable support to be worn by the user and one or more haptic generators. A user interface activates the one or more haptic generators. A massager has a massage head to engage the user to provide massage therapy to the user by vibrating in response to activation of the one or more haptic generators. The massager is movably coupled to the wearable support to move relative to the wearable support between a first configuration in which the massage head is directed toward the user to engage the user when the wearable support is worn by the user and a second configuration in which the massage head is directed away from the user to avoid contact with the user when the wearable support is worn by the user.

In some embodiments, a method is provided for using a wearable device. The wearable device includes a band to be worn by the user, one or more haptic generators, a housing coupled to the band, and a projection protruding from the housing. The method comprises placing the housing in a first configuration so that the projection is directed toward the user. The method further includes performing a combination of acupressure therapy and haptic therapy by activating the one or more haptic generators with the housing in the first configuration and moving the housing from the first configuration to a second configuration so that the projection is directed away from and out of contact with the user. One or more haptic generators are activated with the housing in the second configuration to generate vibrations felt by the user. The band is reversed to place the housing in a third configuration.

In some embodiments, a method is provided for sensing force with a wearable device. The wearable device includes a band to be worn by the user, one or more haptic generators, a housing coupled to the band, a projection protruding from the housing, and a force sensor. The method comprises applying the projection protruding from the housing to skin of the user to provide therapy to the user and activating the one or more haptic generators to generate vibrations to be felt by the user while the projection is applied to the skin of the user. Force of the projection exerted on the user is measured while activating the one or more haptic generators.

In some embodiments, a method provides haptic therapy to a user using a wearable device. The wearable device includes a wearable support to be worn by the user, one or more haptic generators coupled to the wearable support, a user interface, and a controller operable in a conditioning mode and a recall mode. The method comprises activating the one or more haptic generators using a predetermined haptic waveform to produce vibrations during each of a plurality of conditioning sessions in the conditioning mode in which the user performs a mind-body intervention, thereby pairing performance of the mind-body intervention and the vibrations to condition the user in the conditioning mode to associate the vibrations with the mind-body intervention. The method also comprises enabling activation of the recall mode after conditioning the user in the conditioning mode thereby enabling the user to activate the one or more haptic generators using the predetermined haptic waveform to produce the vibrations in the recall mode to relax the user to a relaxed state from an elevated stress state.

In some embodiments, a method provides haptic therapy to a user using a wearable device. The wearable devices includes a band to be worn by the user, one or more haptic generators, a housing enclosing the one or more haptic generators, and a projection protruding from the housing. The method comprises placing the housing in a first configuration in which the projection is directed toward the user to engage the user and activating the one or more haptic generators with a predetermined haptic waveform, when the housing is in the first configuration to produce vibrations during each of a plurality of acupressure sessions. The housing is moved from the first configuration to a second configuration in which the projection is directed away from the user to avoid contact with the user and the one or more haptic generators are activated using the predetermined haptic waveform, when the housing is in the second configuration, to relax the user.

In some embodiments, a method is provided for using a wearable device in combination with a smart device. The method comprises activating one or more haptic generators of the wearable device using a predetermined haptic waveform to generate vibrations to be felt by a user to haptically guide the user through multiple phases of a first breathing session. The user is visually guided through the multiple phases of the first breathing session using a display of the smart device, while activating the one or more haptic generators using the predetermined haptic waveform. The user is haptically guided through multiple phases of a second breathing session, in a recall mode, by activating the one or more haptic generators using the predetermined haptic waveform, but without providing any visual guidance on the display to visually guide the user through the second breathing session.

In some embodiments, a method provides haptic therapy to a first user. The method comprises receiving voice input from a second user and converting the voice input to haptic data. One or more haptic generators of the wearable device are activated using the haptic data to generate vibrations felt by the first user associated with the voice input of the second user.

In some embodiments, a method provides haptic therapy to a first user in combination with a smart device used by a second user. The method comprises receiving, with the smart device, voice input from the second user and converting the voice input to haptic data. The haptic data is transmitted from the smart device to the wearable device. One or more haptic generators of the wearable device are activated using the haptic data to generate vibrations felt by the first user associated with the voice input of the second user.

In some embodiments, a method provides haptic therapy to a user. The method comprises receiving a selection of music from the user and converting the music to haptic data. One or more haptic generators of the wearable device are activated using the haptic data to generate vibrations felt by the user associated with the music.

In some embodiments, a method provides haptic therapy to a user. The method comprises receiving a selection of music from the user and converting the music to haptic data. The haptic data is transmitted from the smart device to the wearable device. One or more haptic generators of the wearable device are activated using the haptic data to generate vibrations felt by the user associated with the music.

In some embodiments, a method provides haptic therapy to a user. The method comprises receiving a selection of music from the user and providing data associated with the selection of music. The method also comprises activating one or more haptic generators of the wearable device using the audio data to generate vibrations felt by the user associated with the music.

In some embodiments, a method provides haptic therapy to a user in combination with a smart device. The method comprises receiving a selection of music from the user and providing audio data associated with the selection of music, transmitting the data from the smart device to the wearable device, and activating one or more haptic generators of the wearable device using the data to generate vibrations felt by the user associated with the music.

In some embodiments, a wearable system comprises a wearable and a smart device. The wearable includes a wrist band, a housing coupled to the wrist band, and a wearable controller. A vibration motor is disposed in the housing to generate vibrations to be felt by the user. One or more physiological sensors are connected to the wearable controller to monitor heart rate and heart rate variability of the user and to initiate the breathing therapy based on values of heart rate and heart rate variability. An inertial sensor is connected to the wearable controller to monitor whether the user is exercising, wherein the wearable controller is configured to automatically initiate the breathing therapy and activation of the vibration motor in response to one or more of the physiological parameters being outside normal values for the user while taking into account whether or not the user is exercising. The wearable lacks a display. A smart device includes a user interface with display to visually display the breathing therapy. The smart device includes a smart controller configured to communicate with the wearable controller to initiate the breathing therapy, wherein the wearable controller monitors values of heart rate and heart rate variability during the breathing therapy and transmits these values to the smart controller to determine whether the values improved during the breathing therapy.

In some embodiments, a wearable system comprises a wearable and a smart device. The wearable includes a wrist band, a housing coupled to the wrist band, a vibration motor disposed in the housing to generate vibrations to be felt by the user, one or more physiological sensors connected to the wearable controller to monitor one or more physiological parameters of the user used to calculate a stress-related metric, and an inertial sensor connected to the wearable controller to monitor whether the user is exercising. The wearable controller is configured to initiate the therapy in response to the stress-related metric being outside normal values for the user while taking into account whether or not the user is exercising. The wearable lacks a display. The smart device includes a user interface with display to visually display the stress-related metric. The smart device includes a smart controller configured to communicate with the wearable controller to initiate the therapy, wherein the wearable controller monitors values of the one or more physiological parameters during the therapy and transmits these values to the smart controller to determine whether the stress-related metric improved during the breathing therapy.

In some embodiments, a wearable system comprises a first wearable to be worn on a wrist of the user, a second wearable to be worn on a finger of the user, and a smart device. The first wearable includes: a wrist band, a housing coupled to the wrist band, a first wearable controller, and a vibration motor disposed in the housing and connected to the first wearable controller to generate vibrations to be felt by the user. The first wearable is configured to perform one or more therapies for reducing stress of the user. The second wearable includes a ring band having a housing, a second wearable controller disposed in the housing, and one or more physiological sensors disposed in the housing and connected to the second wearable controller to monitor one or more physiological parameters of the user. The first wearable and the second wearable both lack any display. The smart device includes a user interface with display and a smart controller configured to communicate with the first wearable controller and the second wearable controller to automatically initiate the therapy.

In some embodiments, a wearable system comprises a wearable and a smart device. The wearable includes a wrist band, a housing coupled to the wrist band, a wearable controller disposed in the housing, and one or more physiological sensors disposed in the housing and connected to the wearable controller to monitor one or more physiological parameters of the user to determine a stress-related metric based on the one or more physiological parameters of the user and to alert the user when the stress-related metric is above a threshold value. The smart device includes a user interface and a smart controller configured to calculate improvement of the stress-related metric and to determine therapy credits to be awarded to the user based on the improvement of the stress-related metric caused by the performance of breathing therapy. The smart controller is configured to access items currently inaccessible to the user that can be made accessible to the user as a result of the therapy credits thereby providing the user with incentive to perform the breathing therapy.

In some embodiments, a wearable system comprises a wearable and a smart device. The wearable includes a wrist band, a housing coupled to the wrist band, and a wearable controller disposed in the housing. One or more physiological sensors monitor one or more physiological parameters of the user to determine a stress-related metric based on the one or more physiological parameters of the user and to alert the user when the stress-related metric is at or above a threshold value. The smart device is capable of communication with the wearable. The smart device includes a user interface with display and a smart controller configured to allow the user to select a desired therapy to be automatically generated in response to the stress-related metric being at or above the threshold value.

BRIEF DESCRIPTION OF THE DRAWINGS

FIG. 1 is a perspective view of a wearable device.

FIG. 2 is a perspective view of the wearable device in a first configuration.

FIG. 3 is a perspective view of the wearable device in a second configuration.

FIG. 7 is an illustration of acupressure point P6.

FIG. 8 is a bottom perspective view of the wearable device in a third configuration.

FIG. 9 is a top perspective view of the wearable device in the third configuration.

DETAILED DESCRIPTION

Figure 4A:
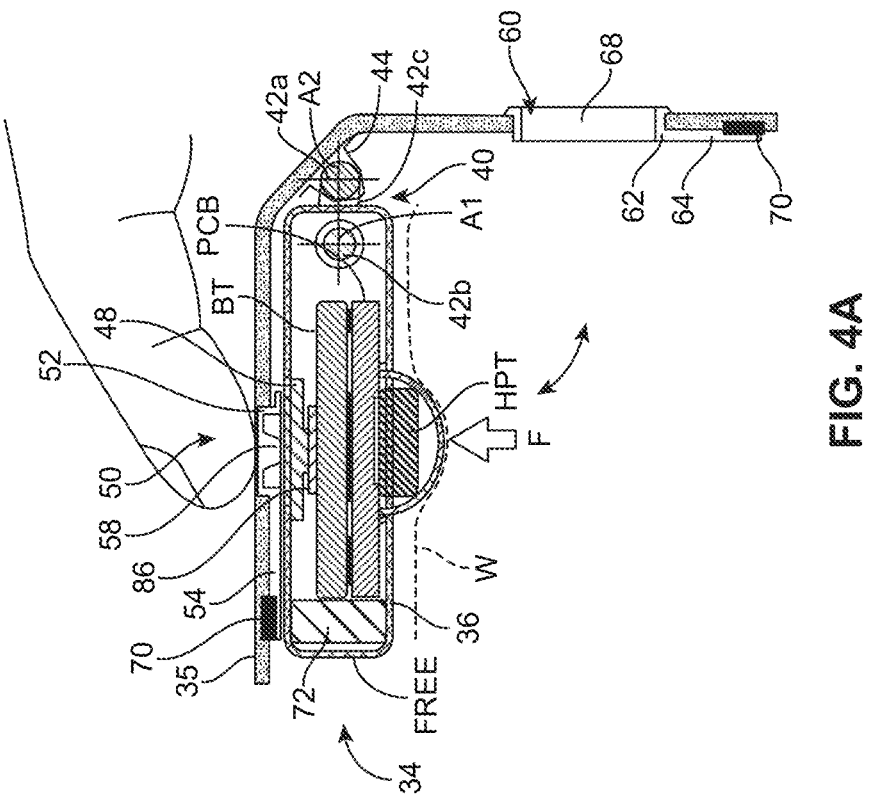
FIG. 4A is a partial and schematic cross-sectional view of the wearable device taken through a midline of the wearable device as shown in FIG. 2.

Referring to FIGS. 1-4, a therapy device is shown for providing therapy to a user to help ease stress, improve stress resilience, enhance sleep, and/or increase energy. The therapy device may be a wearable device 30 or any other suitable form of device. The wearable device 30 can also be used to treat other ailments, such as nausea, pain, headaches, fatigue, and menopause, and to generally improve overall health and wellbeing of users. The therapy that can be provided by the wearable device 30 includes self-administered acupressure therapy, breathing therapy, music therapy, affirmation therapy, haptic therapy, and combinations thereof. Haptic therapy includes vibration therapy and/or pressure therapy, as described further below. The wearable device 30 may also measure and/or monitor physiological parameters such as heart rate, heart rate variability (HRV), skin temperature, blood pressure, EEG readings, ECG readings, blood oxygen, glucose (in blood, sweat, interstitial fluid, etc.), combinations thereof, and the like. In some cases, the therapy performed by the wearable device 30 is automatically triggered in response to one or more of the user's physiological parameters falling outside normal levels, indicating that the user may be experiencing stress, anxiety, nausea, pain, etc., and needs therapy to resolve it.

The wearable device 30 comprises a wearable support 32 configured to be worn by the user. The wearable support 32 may include a band to be worn on any suitable limb or appendage of the user. In the version shown in FIGS. 1-4, the wearable support 32 is a wrist band to be worn on a user's wrist W, but the wearable support 32 may take other forms, such as a ring band to be worn on a finger, a head band to be worn on a head, an arm band to be worn on an arm, a leg band to be worn on a leg, an ankle band to be worn on an ankle, an ear piece to be worn on an ear, a garment (e.g., shirt, shorts, pants, dresses, undergarments, socks, shoes), an adhesive patch for attaching to skin, a clip for attaching to clothing, or the like. The wrist band shown in FIG. 1 may be formed of inelastic, elastic, and/or semi-elastic materials, or combinations thereof. Examples of suitable materials include, but are not limited to, vinyl, silicone, non-woven fabric, woven fabric, elastic fabric, Tyvek® plastic, Neoprene, leather, faux leather, and the like. In some versions, the wrist band includes one or more flexible layers 35. In some versions, the flexible layers may be formed of any suitable elastic material, such as silicone, neoprene, etc., so that the wrist band can stretch to accommodate larger and smaller wrist sizes. The wrist band shown in FIG. 1 is a continuous, elastic loop, but various strap configurations, connections, adjustment mechanisms, etc. may also be employed to fit the wrist band to the wrists of users. Other materials and configurations of the wrist band are contemplated.

Referring to FIGS. 1-4, a housing unit 34 is coupled to and supported by the wearable support 32. The housing unit 34 includes a housing 36. The housing 36 may be one-piece, two-piece, or any suitable configuration. The housing 36 shown in FIGS. 1-4 is a two-piece plastic housing comprising a top housing portion and a bottom housing portion that are fixed together during manufacture, such as via RF welding, ultrasonic welding, adhesive, combinations thereof, and the like. The housing unit 34 includes one or more haptic output devices, which can be used to provide haptic therapy to the user, guide the user during breathing therapy, play vibrational equivalents of music, condition the user as described further below, etc. The haptic output devices may comprise haptic generators HPT disposed in the housing 36. The haptic generators HPT may be haptic actuators in the form of vibration motors that generate vibrations that can be felt/sensed by the user. Such vibration motors may be electric DC vibration motors that have an eccentric mass that is rotated to generate such vibrations in response to supplied electrical current. The haptic generators HPT may also be haptic actuators in the form of linear resonant actuators (LRAs), another form of vibration motor. The haptic generators HPT may also be haptic actuators in the form of piezoelectric actuators that vibrate when supplied with electrical current or may include shape memory materials that change shape when heated and provide associated haptic output to the user. In some versions, the piezoelectric actuators may be configured to generate ultrasonic output that can be felt/sensed by the user. Combinations of vibration motors, piezoelectric actuators, other haptic generators, and/or other haptic output devices may be used.

Figure 4:
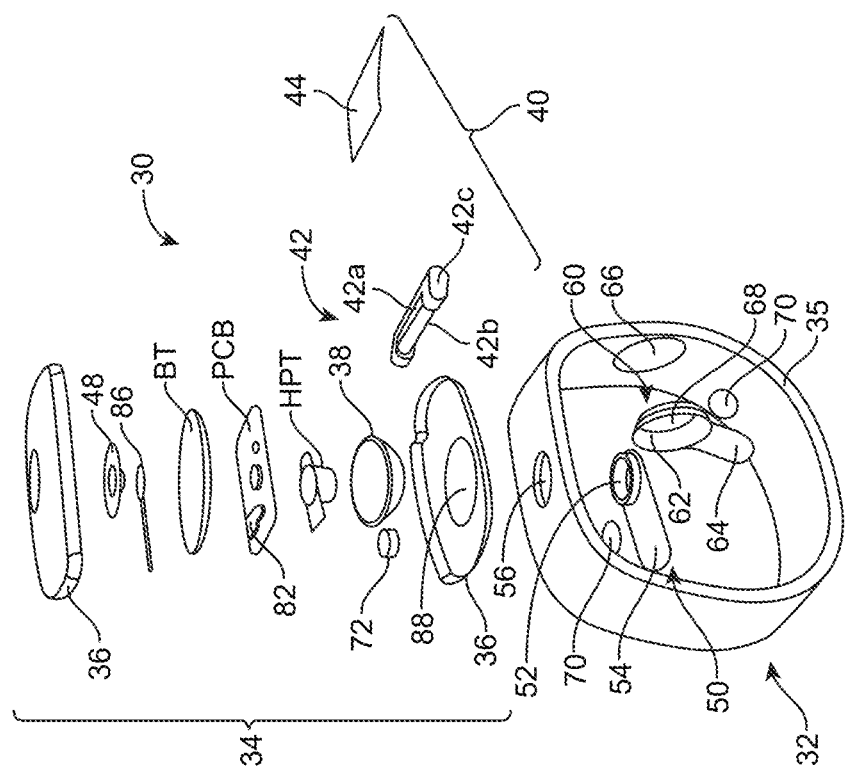
FIG. 4 is a perspective and exploded view of the wearable device.
Figure 5:
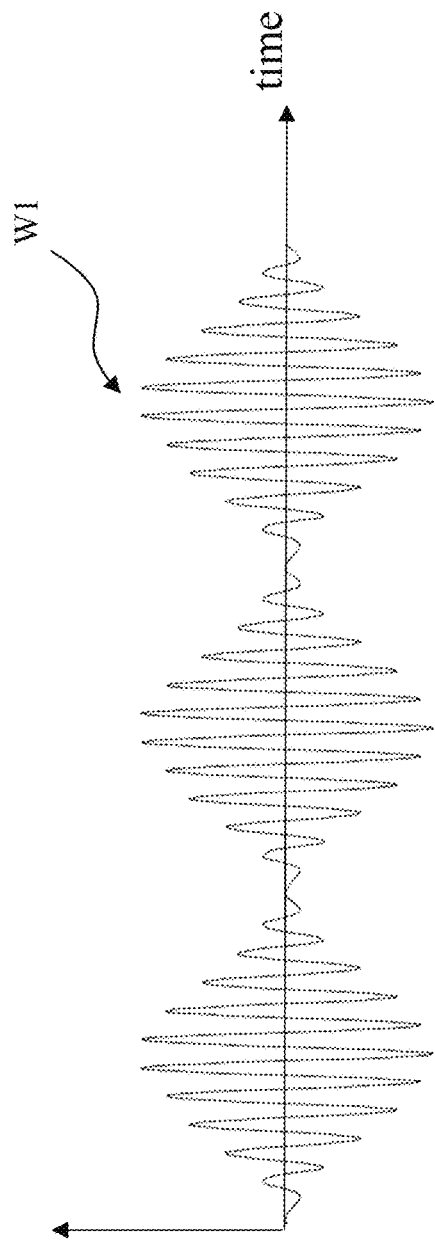
FIGS. 5 and 6 are examples of haptic waveforms.
Figure 6:
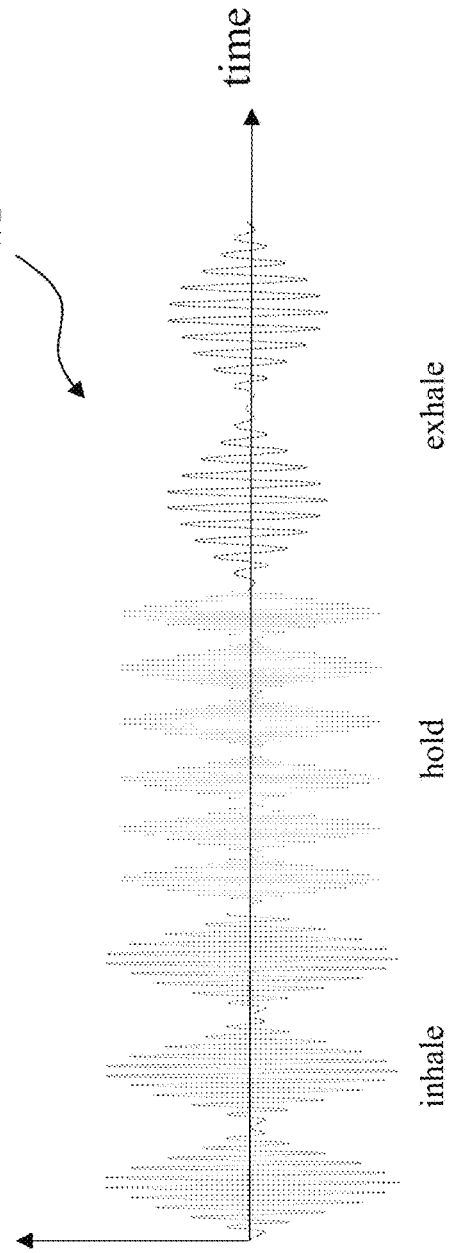

In some embodiments, the one or more haptic generators HPT includes an LRA from Vybronics Ltd. of Hong Kong, Model No. VG1040003D with a resonant frequency of around 175 Hz. The output of this linear resonant actuator can be varied from about 0-200 Hz by varying input voltage to achieve vibration frequencies of 150-200 Hz and with the use of well-known amplitude modulation to achieve vibrations with a frequency of 0.1-40 Hz. The amplitude-modulated control signals may be passed through a low pass filter to an LRA driver to drive the LRA. Examples of amplitude-modulated control signals are shown in FIGS. 5 and 6. Vibrations generated by the one or more haptic generators HPT may be of various magnitudes, frequencies, patterns, etc. In some cases, the vibrations may be gentle touch vibrations, that are configured to mimic another person's touch on the user's skin. The vibrations may also mimic breathing patterns, may indicate different phases of breathing protocols, may represent the vibrational equivalent of music, and the like. The vibrations may be additionally, or alternatively, be programmed from another person's voice recordings. Suitable modulation techniques include amplitude modulation, frequency modulation, or double-sideband, suppressed-carrier modulation. In the version shown in FIGS. 1-4, conventional amplitude modulation is employed according to the formula:

$$A \sin(\omega_0 t)(1-M/2(1+\sin(\omega_M t))) \quad (1),$$

where A is the amplitude, in the range of 0 to full-power; $\omega_0$ is the base frequency, 175 Hz by default; M is modulation depth, in the range of 0 to 1 (0% to 100%); and $\omega_M$ is the modulation frequency. In other versions, double-sideband-suppressed carrier (DSB-SC) modulation could be employed, but the output signal always goes to zero at some point so partial modulation is not possible. Additionally, an output signal from this form of modulation has the consequence of feeling as if the vibrations occur at twice the expected frequency. Other forms of modulation could also be employed.

In some versions, the haptic generators HPT are vibration motors that rotate in a range of rotations per minute (RPM) or that operate at a predetermined frequency. For instance, some of the haptic generators HPT may operate in a range of from 100 to 10,000 RPM, from 1,000 to 5,000 RPM, from 1,500 to 4,500 RPM, or the like. Some of the haptic generators HPT may operate at a frequency of from 5 to 100 Hz, from 10 to 80 Hz, from 30 to 80 Hz, from 40 to 70 Hz, or the like. Some of the haptic generators HPT may operate above 10,000 RPM or above 100 Hz, such as from 100 Hz to 200 Hz.

In one version, there are four haptic generators HPT embedded into the wearable support 32, beneath an interface surface of the wearable support 32. In other versions, the haptic generators HPT may be disposed on the interface surface for direct contact with the user. A single haptic generator HPT, or multiple haptic generators HPT could be employed. Other suitable haptic generators HPT include, for example, 3.0V DC micro coin vibration motors from Best-Tong, available at www.Amazon.com. Other suitable haptic generators HPT and controls for the haptic generators HPT include those available from Boreas Technologies Inc. located in Bromont, Quebec (e.g., PowerHap actuators, part no. 1204H018V060 and associated piezoelectric drivers available in the BOS1901-Kit).

In the version shown in FIGS. 1-4, the housing unit 34 includes an acupressure therapy interface to enable the user to self-administer acupressure therapy. The acupressure therapy interface may include a projection 38 to engage skin of the user during self-administered acupressure therapy. The projection 38 is generally in the form of a massage head, such as a generally dome-shaped body, coupled to the housing 36 and extending from the housing 36. The projection 38 may be coupled to the housing 36 in any suitable manner, including welding, adhesive, fasteners, sewing, heat staking, connectors, snap-fit connections, flexible connections, or the like. In some versions, the projection 38 is coupled to the housing 36, yet free to slide in/out relative to the housing 36. In some versions, the projection 38 is integrally formed with the housing 36 and extends from the housing 36. The projection 38 may extend from 0.1 to 0.5 inches from the housing 36. The projection 38 may extend from 0.2 to 0.4 inches from the housing 36 or may extend at least 0.2 inches from the housing 36. The projection 38 extends from the housing 36 to apply pressure on acupressure points of the user, or to otherwise massage the user. For example, the projection 38 applies pressure on acupressure point P6 of the user's wrist W when the wearable support 32 is worn on the user's wrist W and properly positioned so that the projection 38 is applying pressure to the acupressure point P6 (see FIG. 7). The projection 38 may be spherically shaped, hemi-spherically shaped, ball-shaped, or have any suitable shape for engaging the user's skin and applying pressure to acupressure points. The projection 38 may have a smooth arcuate side portion and arcuate and/or flat top portion as contact surfaces for engaging skin of the user. In some versions, multiple projections may be provided to engage the user's skin. The one or more projections 38 may be substantially rigid compared to the wearable support 32 or may be resilient. The one or more projections 38 may be formed of plastic, such as high-density polyethylene (HDPE), polystyrene (PS), polyethylene terephthalate (PET), or the like. A soft fabric layer, silicone layer, a low friction coating layer (e.g., Teflon), a silicone covering, etc. may be placed over the projection 38 to act as a skin interface between the projection 38 and the user's skin. In some versions, the housing unit 34, including the projection 38, may be referred to as a massage unit or a massager having a massage head.

The housing unit 34 is movably connected to the wearable support 32 via a hinge connection 40 to enable the wearable device 30 to be changed to different use configurations, as described further below. As best shown in FIG. 4, the hinge connection 40 includes a hinge 42, such as the D-ring shown, or any other suitable hinge. In the version shown, the D-ring includes a first hinge rod 42a connected to a second hinge rod 42b by a pair of side arms 42c to form a D-ring opening. The second hinge rod 42b passes through openings in the housing 36 to pivotally couple to the housing 36 (see FIG. 4A). The second hinge rod 42b may be fixed from rotation relative to the first hinge rod 42a or may be rotatable relative to the first hinge rod 42a and the side arms 42c. In some versions, both hinge rods 42a, 42b may be rotatable relative to the side arms 42c.

The hinge connection 40 also includes a strip 44 of flexible material that is connected along both its opposing ends to the flexible layer 35 of the wearable support 32. The strip 44 may be a rectangular strip of material connected at its opposing ends to the wearable support 32 by stitches, RF welding, ultrasonic welding, adhesive, combinations thereof, and the like. The strip 44 may be formed of nylon, woven fabric, non-woven fabric, silicone, canvas, or other suitable materials. The strip 44 is connected to the wearable support 32 such that a through opening is formed between the strip 44 and the wearable support 32 to receive the hinge 42. During manufacture, the strip 44 passes through the D-ring opening and is secured at its ends to the flexible layer 35 to thereby couple the hinge 42 to the flexible layer 35. In some versions, the hinge 42 may be detachable from the flexible layer 35 to allow different wrist bands to be interchanged with the housing unit 34. The hinge 42 is pivotally coupled to the wearable support 32 by virtue of the first hinge rod 42a being disposed in the through opening (see FIG. 4A). The housing 36 defines the openings to receive the second hinge rod 42b of the hinge 42 so that the hinge 42 is pivotally coupled to the housing 36 thereby enabling the hinge 42 to pivot relative to the housing 36.

In some versions, the hinge 42 may be fixed from pivoting relative to the housing 36 and/or the hinge 42 may be integrally formed with the housing 36. The hinge 42 may alternatively be fixed to the one or more flexible layers, or be integrally formed therewith, and pivotally coupled to the housing 36. Other pivot connections for enabling the housing unit 34 to pivot relative to the wearable support 32 are also contemplated. In some versions, the hinge 42 is a double hinge.

Owing to the hinge connection 40, the wearable device 30 is operable in three different configurations, including: (i) a first configuration in which the projection 38 is directed toward the user's wrist when the wearable support 32 is worn on the user's wrist (see FIGS. 2 and 4A); (ii) a second configuration in which the projection 38 is directed away from and out of contact with the user's wrist when the wearable support 32 is worn on the user's wrist (see FIG. 3); and (iii) a third configuration in which the wearable support 32 is reversed or inverted for use off the user's wrist (see FIGS. 8 and 9). In the first configuration, the wearable device 30 can provide self-administered acupressure therapy and/or haptic therapy to the user in the manner described herein, such as by placing the projection 38 in contact with the acupressure point P6 and/or by activating the one or more haptic generators HPT for haptic therapy. In the second configuration, self-administered acupressure therapy is unavailable due to the projection 38 being directed away from and out of contact with the user, but the wearable device 30 can still provide haptic therapy to the user in the manner described herein, such as by activating the one or more haptic generators HPT for haptic therapy or music therapy, or the one or more haptic generators HPT can be activated to guide the user during breathing therapy. In the third configuration, the user can grasp the wearable support 32 as a sort of handle to manipulate the housing unit 34 and apply the projection 38 to other acupressure points on the user for acupressure therapy, or to generally apply the projection 38 to other areas of the user's body for massage. The one or more haptic generators HPT can also be activated in the third configuration for haptic therapy.

The housing unit 34 is movable (swingable or pivotable) between the first configuration and the second configuration (see double arrow in FIGS. 1 and 4A). The housing 36 may pivot about one or more pivot axes A1, A2 that are arranged crosswise to the flexible layer 35 such that pivoting of the housing 36 about either or both pivot axes A1, A2 allows an entire free end FREE of the housing 36 to sweep through an arc from one portion of the wearable support 32 to a separate, spaced portion of the wearable support 32. In the version shown, the housing 36 has a single hinged end (where the hinge is located) and a single free end FREE (not hinged) that is opposite the hinged end, that swings between these configurations. The wearable support 32 defines an interior space in which to receive the wrist W of the user. The free end of the housing 36 is configured to move (e.g., swing or pivot) relative to the wearable support 32 through the interior space between the first configuration and the second configuration. The single hinged end is pivotally coupled to the wearable support 32 such that the free end FREE of the housing 36 is free to move relative to the wearable support 32 about the hinge 40 (or about one or more pivot axes thereof) in the interior space between the first configuration and the second configuration.

In the first configuration (enabling acupressure therapy and/or haptic therapy), a button 48 of the housing unit 34 (see FIG. 4A) is operable through the flexible layer 35 of the wearable support 32 via an actuator 50 that is fixed to the flexible layer 35, e.g., integrated into the flexible layer 35. In other words, in the first configuration, the user can indirectly depress the button 48 by pressing the actuator 50, which engages and depresses the button 48. The actuator 50, in the version shown, includes a separate insert that is attached to the flexible layer 35 (see FIGS. 4 and 4A). The actuator 50 may be formed of silicone or other suitable, flexible, material and may include a flexible button engager 52 and a flexible tab 54. During manufacture, the flexible button engager 52 is inserted through an opening 56 in the flexible layer 35 and the flexible tab 54 is fixed to the flexible layer 35 adjacent the opening 56. The flexible tab 54 may be fixed to the flexible layer via stitches, RF welding, ultrasonic welding, adhesive, combinations thereof, and the like. The flexible button engager 52 includes an annular hub fixed to the flexible layer 35 and a protrusion 58 connected by a thin wall of material to the annular hub. The protrusion 58 is capable of being moved by the user relative to the annular hub to engage the button 48. When a top of the flexible button engager 52 is depressed (see finger pressing in FIG. 4A), the protrusion 58 of the flexible button engager 52 flexes relative to the flexible layer 35, relative to the annular hub and relative to the flexible tab 54, and moves to engage and press the button 48 coupled to the housing 36 to activate the one or more haptic generators HPT. Force/pressure is applied to the projection 38 by the user's skin via the user depressing the button 48, which is aligned with the projection 38. Additional force/pressure is applied to the projection 38 by the user's skin, by virtue of tension on the wearable support 32 when worn by the user. In some versions, the button 48 may simply be activated through the flexible layer 35, without using a separate insert as shown, or the housing 36 may have an embossed portion that fits into the opening 56 in the flexible layer 35 to present the button 48 directly to the user.

In the second configuration (see FIG. 3), the button 48 faces the user's wrist and the projection 38 is captured in a receiver 60. The receiver 60 acts to constrain the projection 38, and thus the housing 36, from substantial lateral movements relative to the flexible layer 35 when in the second configuration. The receiver 60, like the actuator 50, includes a separate insert that is fixed to the flexible layer 35, e.g., integrated into the flexible layer 35 (see FIG. 4A). The receiver 60 may be formed of silicone or other suitable material and may include a pocket portion 62 and a flexible tab 64. The pocket portion 62 is inserted through an opening 66 in the flexible layer 35 and the flexible tab 64 is fixed to the flexible layer 35 adjacent the opening 66. The flexible tab 64 may be fixed to the flexible layer 35 via stitches, RF welding, ultrasonic welding, adhesive, combinations thereof, and the like. The pocket portion 62 includes a ring that defines a pocket 68 to receive the projection 38 when the housing 36 is pivoted/rotated/swung into the second configuration, in much the same manner as a detent pocket and detent operate.

Metallic connectors 70, such as small metal discs, may be disposed and captured between each of the flexible tabs 54, 64 and the flexible layer 35. The metallic connectors 70 may be fixed to the flexible tabs 54, 64 and/or the flexible layer 35 via adhesive, insert molding, friction, and/or by otherwise being constrained therebetween. The housing unit 34 may include a magnet 72 fixed in the housing 36 to attract the metallic connectors 70 to thereby attract the housing 36 and further secure the housing 36 from movement relative to the flexible layer 35 when in the desired first or second configuration. The magnet 72 and metallic connectors 70 may also be reversed such that magnets are disposed and captured between each of the flexible tabs 54, 64 and the flexible layer 35 and fixed relative to the flexible layer 35, and a metallic connector is fixed to the housing 36. Other fastening mechanisms/connectors are also contemplated to further secure the housing 36 from movement relative to the wearable support 32 in the desired configuration. The metallic connectors and the magnets, as well as any other suitable couplings, form complementary couplings that releasably hold the housing 36 in the desired first or second configuration. These complementary couplings can be of any suitable form for releasably holding the housing 36 from easily being dislodged in the first or second configuration.

Referring to FIGS. 8 and 9, in the third configuration, in which the wearable support 32 has been reversed (inverted inside-out), the wearable support 32 is operable as a handle for the user to grasp in their palm while manipulating the housing 36 and positioning the projection 38 against one or more acupressure points during self-administered acupressure therapy and/or haptic therapy. Thus, with a single hand, the user can place the projection 38 against an acupressure point for acupressure therapy, or for general massage, and depress the button 48 (in this case directly) to activate the one or more haptic generators HPT for haptic therapy. Alternatively, the user could simply manipulate the housing 36 (and not the wearable support 32) to position the projection 38 for acupressure therapy, general massage, and/or haptic therapy. In the third configuration, the user can easily place the projection 38 on other anatomical sites to stimulate multiple acupressure points, while the one or more haptic generators HPT simultaneously produce vibrations through the projection 38 to be felt by the user at the multiple acupressure points.

Figure 10:
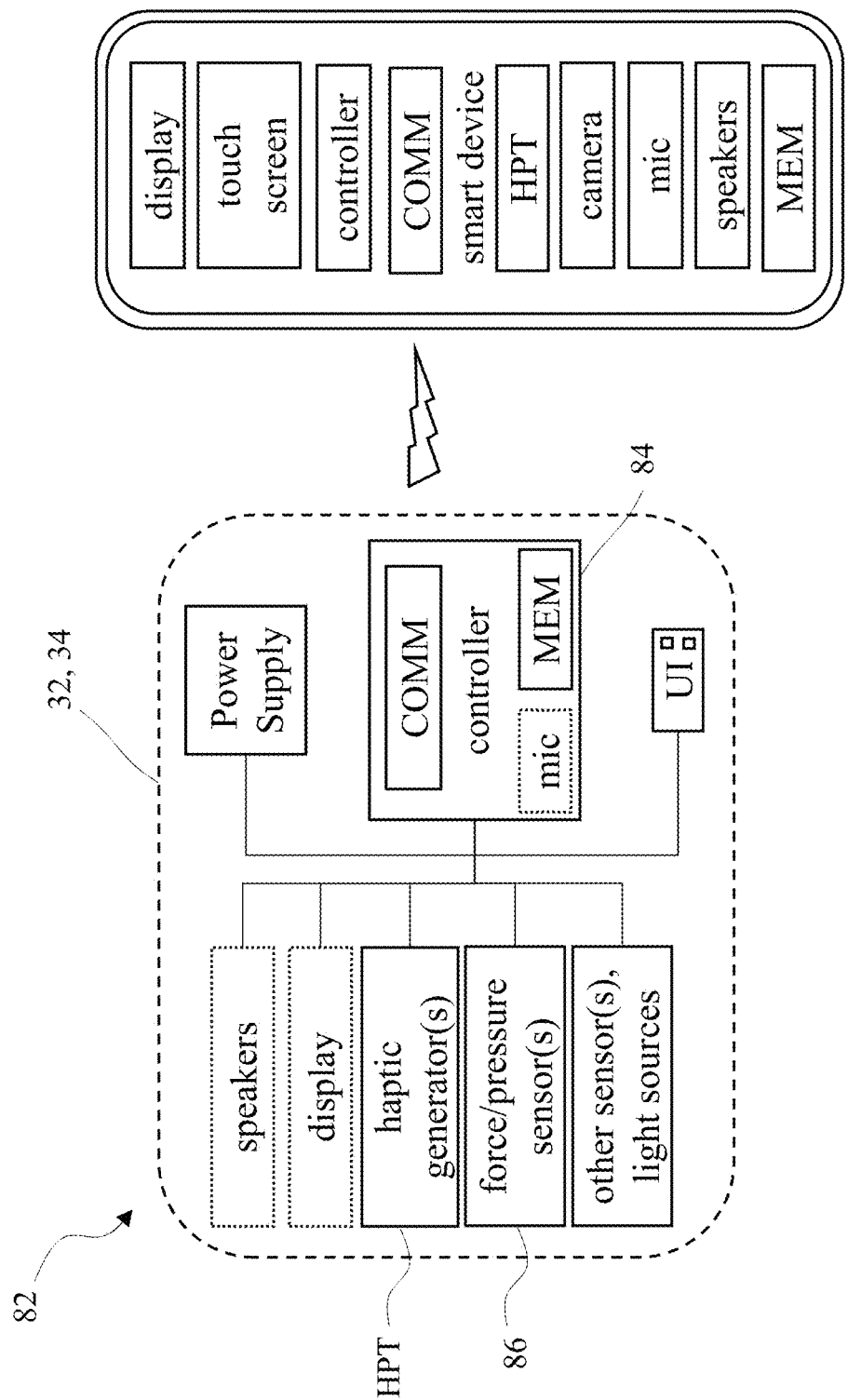
FIG. 10 is a block diagram of a control system.

Referring to FIG. 10, a control system 82 for the wearable device 30 is shown. The control system 82 includes a controller 84 that is operatively coupled to the haptic generators HPT to control activation and deactivation of the one or more haptic generators HPT. The controller 84 may include one or more microprocessors, microcontrollers, field programmable gate arrays, systems on a chip, volatile or nonvolatile memory, discrete circuitry, and/or other hardware, software, or firmware capable of carrying out the functions described herein. In some versions, the controller 84 is part of the housing unit 34 and disposed in the housing 36, such as on printed circuit board PCB. In some versions, the controller 84 is part of the wearable support 32. In some versions, the controller 84 is part of a separate smart device (e.g., smartphone, smartwatch, tablet, etc.). The term controller 84 may refer to a controller of the housing unit 34, a controller of the wearable support 32, and/or a controller of the smart device, or any combinations thereof. The filter and driver for the one or more haptic generators HPT may form parts of the controller 84 of the wearable device 30. In some versions, the control system 82 may also include a display, such as a liquid crystal display (LCD), a light emitting diode (LED) display, organic light emitting diode (OLED) display, or other type of display on the wearable device 30 and/or the smart device. In some versions, the housing unit 34 includes a smart watch display unit, such as an Apple Watch, Samsung Watch, or other form of smart watch display unit with associated display and touch screen interface. The housing unit 34 may carry one or more batteries BT (see FIG. 4A) coupled to the controller 84 and other electronic components in the housing unit 34 for providing power to such components. The one or more batteries BT may be rechargeable, disposable, of any suitable form, and may be enclosed within the housing 36.

A user interface UI is provided by the control system 82 for interacting with the user to receive input from the user. The user interface UI is operatively coupled to the controller 84 to control the electronic components described herein. The user interface UI of the wearable device 30 may include buttons, such as the button 48. In some versions, the button 48 forms part of a momentary contact switch so that the one or more haptic generators HPT are activated/deactivated by pressing/releasing the button 48. More specifically, when the button 48 forms part of a momentary contact switch, operation of the one or more haptic generators HPT stops when the user ceases applying force/pressure on the button 48 (e.g., by virtue of spring force of the momentary contact switch opening a circuit). In some versions, the button 48 is an integral part of the housing 36 that either flexes or has connectivity to the controller 84 to register user input when pressed. In some versions, the user interface UI may include a separate button that is depressed to activate the one or more haptic generators HPT such that the one or more haptic generators HPT remain active until the separate button is subsequently depressed a second time. The user interface UI may additionally, or alternatively, include a touch screen (e.g., capacitive touch screen, etc.), sensors (e.g., touch sensors, gesture sensors, accelerometers, gyroscopes, 6-axis inertial sensors, etc.), other buttons, or other forms of user input devices.

In the version shown, the user interface UI includes the physical button 48 for being engaged by the user (either directly or indirectly) and a touch sensor for detecting touching/tapping input by the user. The touch sensor may include one or more accelerometers, gyroscopes, 6-axis inertial sensors, and the like to detect user gestures, such as single taps, double taps, etc. of the user on the housing unit 34. For example, the controller 84 may be programmed to detect a double tap on the housing unit 34 via an accelerometer connected to the controller 84. This double-tap input may act to "wake" certain electronic components to otherwise preserve battery life. For example, upon detecting a double tap, the controller 84 may activate wireless communication COMM to begin advertising a radio frequency signal (e.g., Bluetooth, Zigbee, WiFi etc.) to connect to the smart device. In some versions, the controller 84 may activate a short, gentle burst (e.g., 1 second) of the one or more haptic generators HPT to generate vibrations on the user's wrist to indicate to the user that the wearable device 30 is now active and ready for further input. The controller 84 may enable activation of the one or more haptic generators HPT in response to detecting the double tap. For example, once the double tap input is received, then the switch associated with the button 48 may be enabled by the controller 84 so that pressing of the button 48 results in activation of the one or more haptic generators HPT. Without "waking" the wearable device 30, the switch associated with button 48 may be disabled such that pressing of the button 48 fails to result in activation of the one or more haptic generators HPT. This may be helpful in preventing inadvertent activations of the one or more haptic generators HPT. In some versions, the switch associated with the button 48 is always active and acts to both "wake" the wearable device 30 and cause activation/deactivation of the one or more haptic generators HPT. It should be appreciated that enabling and disabling of the switch associated with the button 48 may be performed via software running on the controller 84.

Double taps may be detected based on input into the controller 84 from the one or more accelerometers, gyroscopes, 6-axis inertial sensor, or the like indicating a sequence of high-acceleration readings associated with a double tapping action, separated by a low/normal acceleration reading associated with the wearable device 30 being relative still or having small accelerations (e.g., the two high-acceleration readings are within a preset amount of time of each other to indicate that double tapping action has occurred, such as being less than 1 or 2 seconds apart). Once the wearable device 30 is active and ready for further input in response to the controller 84 receiving the double tap input, then another double tap input may result in the wearable device 30 activating the one or more haptic generators HPT to generate vibrations at the last vibration settings stored in the memory MEM of the wearable device 30. In some cases, in response to detecting a double tap input, instead of merely activating the wearable device 30 to make it ready for further input, the wearable device 30 may automatically activate the one or more haptic generators HPT to generate vibrations based on the last vibration settings stored in the memory MEM of the wearable device 30. A further double tap input may deactivate the one or more haptic generators HPT. Single taps, other tapping sequences, or other user gestures may be used in place of double tap inputs to wake the wearable device 30 or activate/deactivate the one or more haptic generators HPT.

The control system 82 may include one or more force and/or pressure sensors 86 connected to the controller 84 to measure the force (or pressure) exerted on the projection 38, such as when the projection 38 is pressing onto the user's skin at various acupressure points (see Force F shown in FIG. 4A). In the version shown, the pressure/force sensor 86 includes a force sensing resistor (FSR) coupled to the controller 84 and disposed between the button 48 and the projection 38. Referring to FIG. 4A, the load path of the force F is transmitted from an interface of the projection 38 with the user, through the projection 38, to the printed circuit board PCB, through the battery, and to the pressure/force sensor 86. The projection 38 is located to extend from the printed circuit board PCB through an opening 88 in the housing 36 such that the projection 38 can move, albeit slightly, relative to the housing 36 through the opening 88 so that force readings can be taken. In the version shown in FIG. 4A, the projection 38 is captured in the housing 36 between a wall of the housing and a stack of components, including the printed circuit board PCB. As a result, the projection 38 is free to move relative to the wall of the housing 36 to apply further force onto the pressure/force sensor 86. In other versions, the housing 36 may be suitably flexible to allow force readings to be taken. In some versions, the pressure/force sensor 86 is located between the printed circuit board PCB and the projection 38 to receive force (see hidden lines in FIG. 4A). This can be useful, for example, when the printed circuit board PCB is fixed to the housing 36 such that pushing on the housing 36 alone to apply pressure through the projection 38 onto the user's skin also pushes on the pressure/force sensor 86 to measure such force/pressure and to measure force/pressure exerted on the projection 38 by the user's skin by virtue of the band alone.

An amplifier coupled to the controller 84 may be used in concert with the FSR to receive the force-dependent resistance from the FSR and generate a force-dependent voltage signal for reading by the controller 84. In some versions, force readings are taken using a force sensor that do not take into consideration the dimensions of the projection 38 (e.g., readings are in lbs. or grams) and then pressure is calculated by the controller 84 or another controller (such as on the smart device) based on the force readings (e.g., lbs. or grams) and the dimensions of the projection 38 (e.g., in$^2$, cm$^2$, etc.)(P=Force/Area).

In some cases, the pressure/force readings (or calculations) may be taken or made periodically, e.g., every second, millisecond, etc. and collected by the controller 84 and stored in the memory MEM for later retrieval by the smart device or may be sent to the smart device in real-time for force/pressure feedback to the user. This may be helpful when the user is trying to maintain the force/pressure within a predetermined, desirable range of forces/pressures. In some cases, the one or more haptic generators HPT may provide haptic feedback to indicate to the user when the force/pressure is outside the range, or within the range, or when a predefined force/pressure value is reached, or exceeded (e.g., via a sharp burst of vibrations). Other feedback devices, such as a speaker, display, or other haptic generator, may also be used for such feedback.

The control system 82 also includes one or more other sensors and/or light sources coupled to the controller 84 that may be used to measure one or more physiological parameters of the user, or to measure selected parameters associated with use of the wearable device 30. These sensors and/or light sources may be disposed in the housing 36. The sensors and/or light sources may include one or more optical sensors (e.g., photodiodes or photodetectors), light sources, ECG sensors, and any other electronic components described herein that transmit signals to and/or receive signals from the controller 84. The one or more force/pressure sensors 86 may be used to measure forces/pressures exerted on the user by the projection 38 during use. The one or more optical sensors and one or more light sources may be used to measure heart rate, heart rate variability (HRV), glucose levels, and/or blood pressure using photoplethysmography (PPG), in which case, the light sources emit light from the housing 36 onto a tissue of the user (e.g., user's wrist W, behind ear, etc.) and the optical sensors in the housing 36 receive and measure the reflected light from the tissue. The reflected light is proportional to blood volume variations. The light sources may include one or more infrared light emitting diodes (IR-LED) and/or one or more green light emitting diodes (G-LED). Other types of near-infrared (NIR) and/or visible light emitting sources and sensors may also be used, which can emit/detect light at various visible and infrared wavelengths. Such light emitting sources may be used for sensing, light therapy, or for other potential uses. Blood volume changes can be measured (calculated) based on the amount of the reflected light using conventional PPG measuring techniques. The optical sensors and the light sources may be mounted the housing 36 or any other suitable location. Suitable sensors and light sources for measuring heart rate, glucose, or other physiological parameters are disclosed in U.S. Patent Application Publication No. 2016/0058375 to Rothkopf, entitled "Wearable Electronic Device," which is hereby incorporated herein by reference.

The wearable device 30 may be configured to wirelessly communicate with one or more smart devices (e.g., via Bluetooth, Zigbee, WiFi, or any other suitable protocol). Such communication may provide data from the wearable device 30 to the smart device, and vice versa, via communication modules COMM. Data may be stored in the memory MEM and later sent from the wearable device 30 to the smart device, to a cloud server, or to any other suitable location for storage, analysis, collection, etc. Data stored on the wearable device 30 may be data related to the number and timing of activations of the wearable device 30, e.g., through the touch sensor and/or the momentary contact switch. Data may also be data from sensors (e.g., from the force/pressure sensor 86) or other input devices. Data may also be sent in real-time between the devices. Communication between the wearable device 30 and the smart device may include the transfer of device settings, instructions, and the like. In some cases, the data sent from the smart device to the wearable device 30 may be data relating to haptic waveforms to be generated by the one or more haptic generators HPT during haptic therapy, during breathing therapy, or during music therapy, and the duration of vibrations desired by the user. For example, the user may be able to select certain parameters of the vibrations to be generated, including the duration of vibrations, and the smart device can transmit the associated waveforms and times to the wearable device 30. In some cases, stored haptic waveforms may be those generated based on voice recordings of other people, or of the user, derived from music, or may be haptic waveforms that are later developed and uploaded to the wearable device 30 via Bluetooth, WiFi, Zigbee, etc., for improved performance.

Various processor/computer-implemented steps are described herein and may be carried out via software modules and software applications that correspond to a set of executable instructions for performing the one or more functions described herein and the methods described in this application (e.g., the processor/computer-implemented methods and other information processing methods described herein). These modules and applications (e.g., sets of instructions) need not be implemented as separate software programs, procedures, or modules, and thus various subsets of these modules can be combined or otherwise rearranged in various embodiments. In some embodiments, the memory MEM stores a subset of the modules and data structures. Furthermore, memory MEM stores additional modules and data structures not described herein. The software modules and/or software applications operable on the wearable device 30 and/or the smart device may wirelessly interface with data storage, such as a cloud server, or may provide local storage for data associated with therapy history, a symptom diary, health data such as heart rate, HRV, etc., applied force/pressure history, or the like, and correlations between such data may be displayed by the smart device, or on the wearable device 30. The wearable device 30 and/or the smart device may also provide reminders to the user to perform therapy, such as when the user wishes to routinely perform such therapy on a predefined schedule programmed into the software application.

Figure 11:
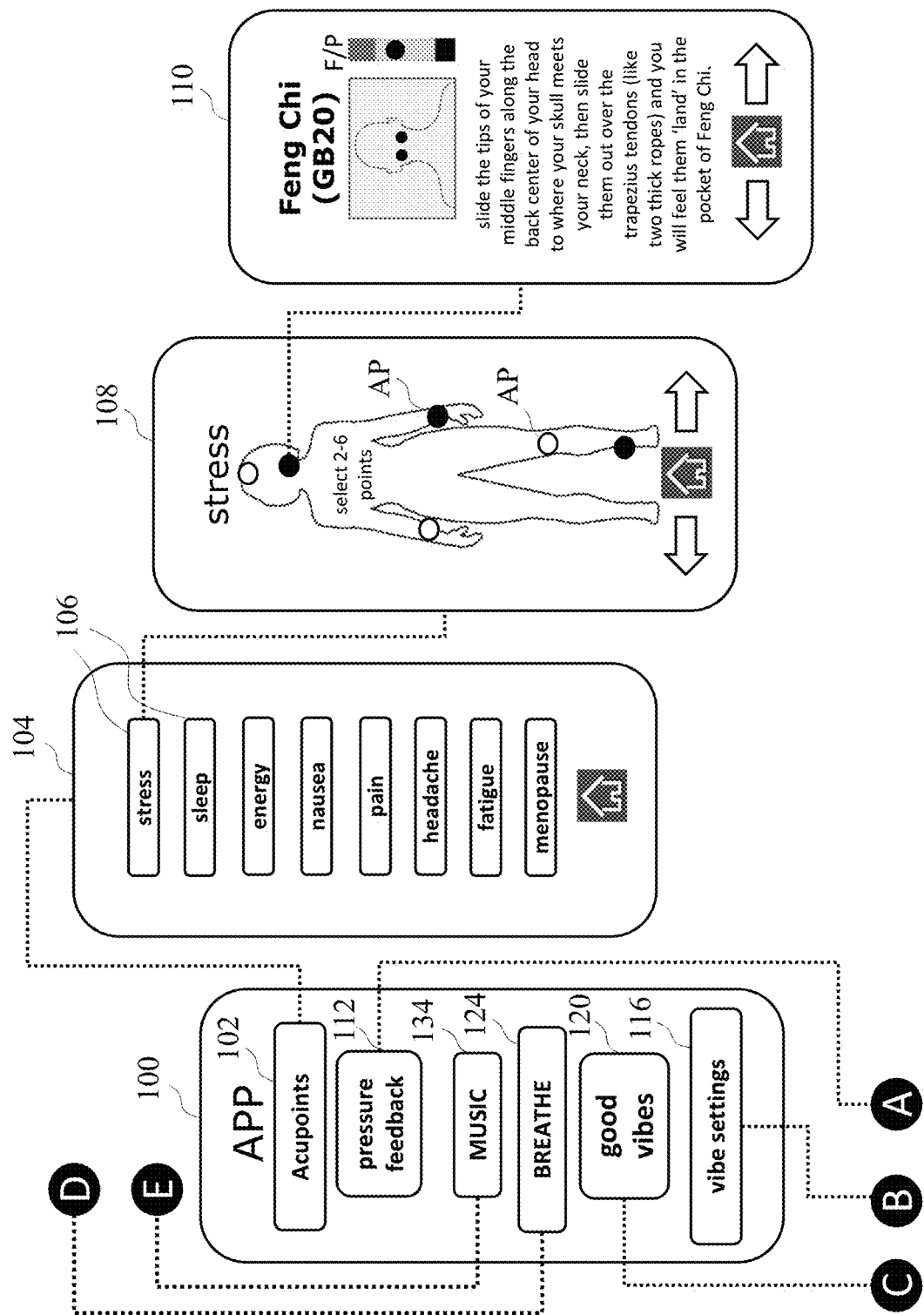
FIG. 11 illustrates an example set of screens output by a software application on a smart device to perform acupressure therapy.

FIGS. 11-14 illustrate examples of display screens output to a display of the smart device by a software application APP. The software application APP may be operable on the smart device, such as the smartphone shown, to: (i) guide users in how to wear or use the wearable device 30; (ii) guide therapy sessions; (iii) facilitate communication between the wearable device 30 and the smart device; (iv) control operational settings on the wearable device 30; (v) receive data from the wearable device 30, and display, analyze, or store such data; and/or (vi) transmit data relating to the user and/or the wearable device 30 to an external server or cloud storage. The software application APP runs on a controller of the smart device. FIG. 11 illustrates a home screen 100 of the software application APP. On the home screen, the display of the smart device identifies user input areas of the touch screen ("buttons") for selection by the user. It should be appreciated that the wearable device 30 may also incorporate all the functions of the smart device described herein, including operation of the software application APP with the display of information/screens, playing of music, etc. being performed on the wearable device 30.

Referring to FIG. 11, the home screen 100 includes a button 102 for "acupoints". Selection of this button 102 causes the software application APP to display a screen 104 for the user to select one of a plurality of buttons 106 associated with different sets of acupressure points. In the example shown, the user selects "stress", which causes the software application APP to display screen 108 associated with the "stress" selection. On screen 108, six acupressure points AP known for reducing stress when stimulated are shown for possible selection by the user (selected acupressure points shown by black-filled circles). If another was selected, such as "sleep", then a different set of acupressure points (with some possible overlap) would be shown for possible selection by the user. Once the user has selected all the acupressure points desired for their acupressure therapy session (e.g., from 2-6 acupressure points), in this case to ease stress, the user is able to select a right arrow button that leads to the software application APP displaying instruction screens 110 on how to find and stimulate each of the selected acupressure points. FIG. 11 shows an example of how the software application APP may provide instructions to the user on how to find and apply pressure to one or more acupressure points with the wearable device 30. In this example, visual images of the acupressure points are shown (points shown on back of neck in FIG. 11), along with text instructions on how to locate these acupressure points and/or apply pressure and/or massage the acupressure points. In other versions, videos may be automatically generated and started with information on how to find and/or apply pressure to each of the acupressure points.

The user may rely on the software application APP to provide instructions on how to find and apply pressure to the acupressure points being stimulated by the wearable device 30, or the user may operate the wearable device 30 to stimulate/massage multiple acupressure points without relying on instructions from the software application APP. In some cases, users will rely on the software application APP to initially train them on how to find the acupressure points and/or how to apply pressure or massage the acupressure points, but will thereafter be able to locate the acupressure points and stimulate them without any reliance on the software application APP. During training, for example, while viewing an instruction screen (not shown) for how to find acupressure point P6 (see FIG. 7), the user may place the wearable device 30 in the first configuration (FIG. 2) in which the projection 38 is directed toward the user's wrist when the wearable support 32 is worn on the user's wrist. The user may then adjust the wearable device 30 so that the projection 38 is directed at the acupressure point P6. Once properly positioned, the user may then press the button 48 via the actuator 50 to further press the projection 38 into the acupressure point P6 and massage the acupressure point P6 by moving the projection 38 in small circles on the acupressure point P6. Simultaneously, because of pressing the button 48, haptic therapy begins on acupressure point P6 by virtue of the controller 84 activating the one or more haptic generators HPT to generate vibrations to be felt by the user through the projection 38 at the acupressure point P6. To access acupressure points off the wrist, the user may switch the wearable device 30 from the first configuration (FIG. 2) to the third configuration (FIGS. 8 and 9) and thereafter stimulate and provide haptic therapy to the other acupressure points in a similar manner based on further instructions viewed on other instruction screens. Having now been trained to locate the acupressure point P6 and other acupressure points off the wrist, the user will be able to provide acupressure therapy on such acupressure points without needing to access the software application APP on the smart device.

Figure 12:
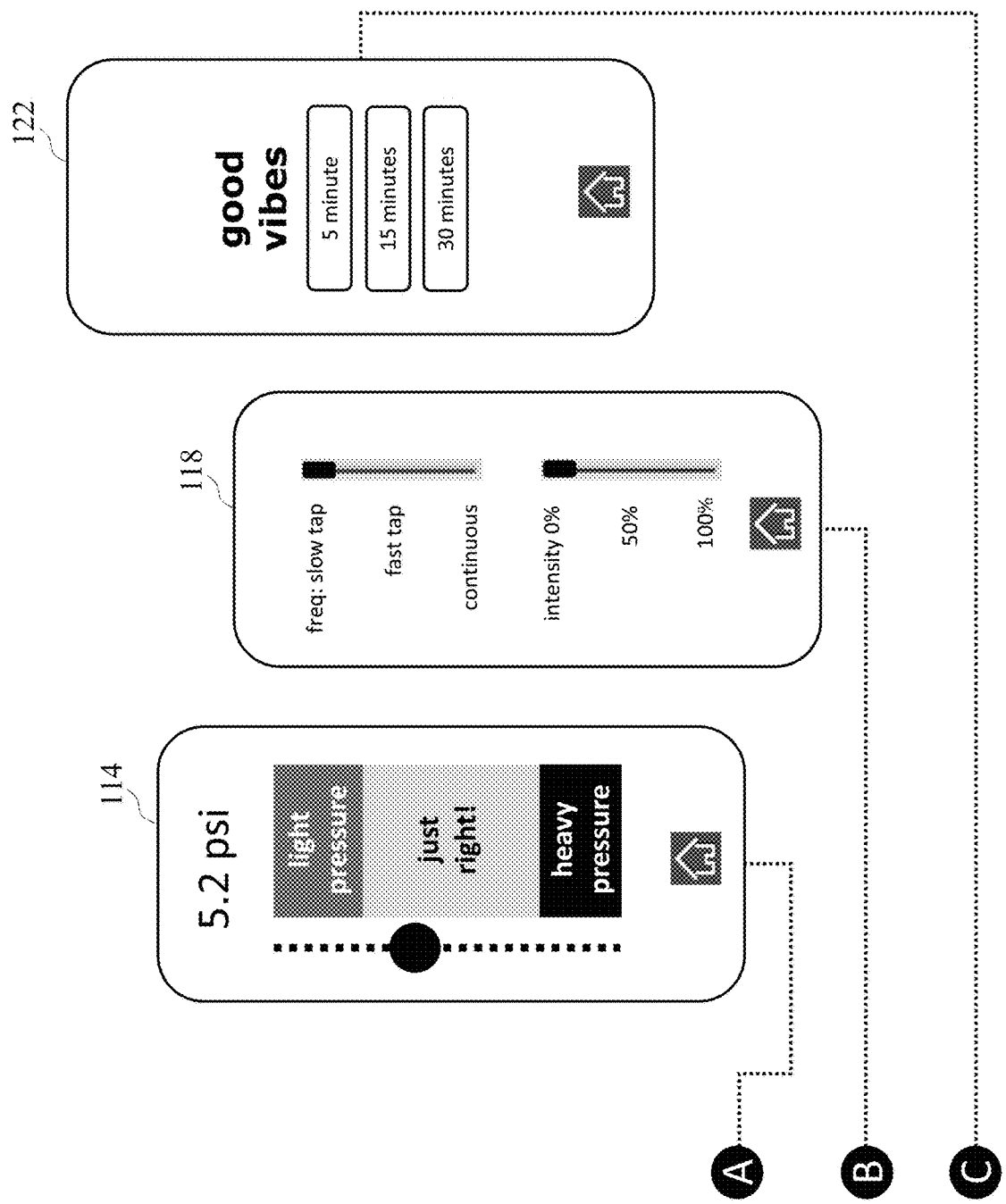
FIG. 12 illustrates an example set of screens output by the software application on the smart device to show pressure feedback, adjust vibration settings, and initiate haptic therapy.

Still referring to FIG. 11, the home screen 100 includes a button 112 for "pressure feedback". Selection of this button 112 causes the software application APP to display screen 114 shown in FIG. 12. The screen 114 depicts force/pressure measurements associated with the force/pressure applied by the projection 38 onto the user (or by the user on the projection 38) during acupressure therapy. For example, once the projection 38 is properly positioned relative to an acupressure point, the user may then press the button 48 via the actuator 50 to further press the projection 38 into the acupressure point and massage the acupressure point by moving the projection 38 in small circles on the acupressure point. The software application APP, via the screen 114, displays a force/pressure value for the user to see how much force/pressure is being applied in relation to a desired force/pressure or range of forces/pressures. The screen 114 may include any of various visual representations or indications of the force/pressure, including a text readout of a discrete value of force/pressure (e.g., "5.2 psi", in the case of pressure readings), and/or scales that show bands of light force/pressure ("light pressure"), acceptable force/pressure ("just right"), or heavy force/pressure ("heavy pressure"). A visual representation of the projection 38 (in this case a black-filled circle) moves along the scale to show where the force/pressure falls along the scale. In FIG. 12, the black-filled circle is shown in the "just right!" range. The intent is to show the user when the force/pressure is inside or outside desired ranges, or when the force/pressure is too light, in range, or too heavy, etc.

The controller 84 on the wearable device 30 determines the force/pressure data based on input into the controller 84 from the force/pressure sensor 86 on the wearable device 30. Once the force/pressure data is collected, the controller 84 transmits the force/pressure data from the wearable device 30 to the smart device in real-time for display to the user so that the user can adjust the force/pressure while self-administering acupressure therapy to themselves. In some versions, the acceptable range of pressure from the projection 38 on the user's skin is from 2-8 psi, with 4-6 psi being desirable. In some versions, the acceptable range of force from the projection 38 on the user's skin is from 0.5-2.0 lbs. In some cases, pressure readings under 2 psi are indicated on the display as "light pressure", with pressure readings over 8 psi being indicated as "heavy pressure" and with pressure readings of 2-8 psi being indicated as "just right!". Similarly, force readings under 0.5 lbs may be indicated as "light force", force readings over 2.0 lbs may be indicated as "heavy force" and force readings of 0.5-2.0 lbs may be indicated as "just right!". Force/pressure readings may be stored on the wearable device 30 over time and transmitted to the smart device to be shown on the display in a graph or chart form that shows trends in the force/pressure readings over time. Force/pressure visual feedback ("F/P") may also be shown on the instructions screens 110 (see FIG. 11) so users can get an idea of whether their force/pressure is in range while being trained to self-administer acupressure therapy via the instruction screens 110. As previously noted, either or both of force and pressure can be displayed, and the pressure displayed may be calculated/derived from a sensed force F, taking into account the area over which the force acts.

The home screen 100 also includes a button 116 for "vibe settings". Selection of this button 116 causes the software application APP to display screen 118 shown in FIG. 12. Examples of settings for the wearable device 30 that may be set or changed via the software application APP running on the smart device, include vibration settings, such as settings relating to the type of vibrations (e.g., tapping, periods of tapping separated by continuous vibrations, etc.), the frequency of the vibrations (e.g., from 0-200 Hz, with 1 Hz being a tapping frequency similar to a resting heart rate and 200 Hz giving the user an impression of a continuous vibration), and the intensity (magnitude) of the vibrations (e.g., from 0-100%). On the screen shown in FIG. 12, the software application APP is programmed to display slider-type inputs for selecting different frequencies (from slow tap to continuous, e.g., from around 0.1-200 Hz) and for selecting different intensities (from 0-100% intensity) with the maximum intensity being a maximum voltage applied to the one or more haptic generators HPT by the haptic driver of the controller 84. Other vibrations parameters capable of being set, beyond those shown, are also contemplated. In some versions, the software application APP may present other user-selectable inputs to be selected by the user on the touch screen. For example, the screen 118 may instead present the user with buttons labeled "slow tapping", "fast tapping", or "continuous" and buttons labeled "low intensity", "medium intensity", or "high intensity". Once the user sets the vibration parameters, the smart device transmits the selected parameters, and/or a haptic waveform (e.g., a waveform file) derived therefrom, to the wearable device 30 via its own communication module COMM and the wearable device 30 receives and stores the parameters/waveform in the memory MEM. Thereafter, the controller 84 of the wearable device 30 operates the one or more haptic generators HPT of the wearable device 30 based on those vibration settings and/or waveform. In some versions, when the user makes a selection on the screen 104, predetermined vibration settings and/or a waveform are set and stored in the memory MEM that are associated with that particular selection and may be different than the settings/waveforms for other selections.

Referring back to FIG. 11, the home screen includes a button 120 for "good vibes". Selection of this button 120 causes the software application APP to display screen 122 shown in FIG. 12. On this screen 122, the user is presented with selectable time periods for which to activate the one or more haptic generators HPT, e.g., "5 minutes", "15 minutes", or "30 minutes". Other time periods are also contemplated and/or a slider bar allowing the user to slide from 1-60 minutes, or any other desirable time, could also be presented. Once the user selects a desired time period on the touch screen, the smart device automatically transmits a signal via its wireless communication module COMM to the wearable device 30 and the time period is received and stored in the memory MEM of the wearable device 30. The controller 84, upon receiving this selection, activates the one or more haptic generators 84 and operates them continuously for the selected time period to provide vibration therapy, using the last vibration settings and/or waveform stored in the memory MEM. In some versions, the wearable device 30 may need to be activated ("wake") first (e.g., via an initial double tap input) to receive these or other selections from the smart device. The controller 84 could be programmed to deactivate the one or more haptic generators HPT early (before the time period expires) and discontinue such vibrations by double tapping the housing unit 34, or by activating the button 48, or by some other input.

During use of the wearable device 30, if the wearable device 30 is first activated (e.g., by double tapping input), and thereafter receives another double tapping input to activate the one or more haptic generators HPT, then the vibration settings/waveform at which the one or more haptic generators HPT operate are the last vibration settings/waveform stored in the memory MEM of the wearable device 30, which may be based on the last settings set by the user on screen 118, e.g., the prior settings/waveform are overwritten by the controller 84. In some versions, the time period for which the one or more haptic generators HPT continue to operate, could be at the last time period stored in the memory MEM, which may be based on the last time period selected by the user on screen 122. Alternatively, the one or more haptic generators HPT may continue to operate at the last stored vibration settings/waveform until another double tap input is received by the controller 84, which would instruct the controller 84 to deactivate the one or more haptic generators HPT.

Being able to activate vibrations based on the last stored settings/waveform allows the user to conveniently operate the wearable device 30 without requiring connection to the smart device. In other words, if the user wishes to quickly operate the wearable device 30 to generate soothing vibrations to calm the user, such as during a meeting, trip, interview, etc., the user merely needs to double tap the wearable device 30 (or provide some other suitable form of input) to start the vibrations. This can be particularly useful, for example, when the user is wearing the wearable device 30 in the second configuration at bedtime and the user wishes to activate soothing vibrations to assist the user in sleeping. A simple double tap activates the vibrations and soothes the user to place the user in a restful sleep. In this case, ending the vibrations at the end of the last stored time period could be beneficial.

Figure 13:
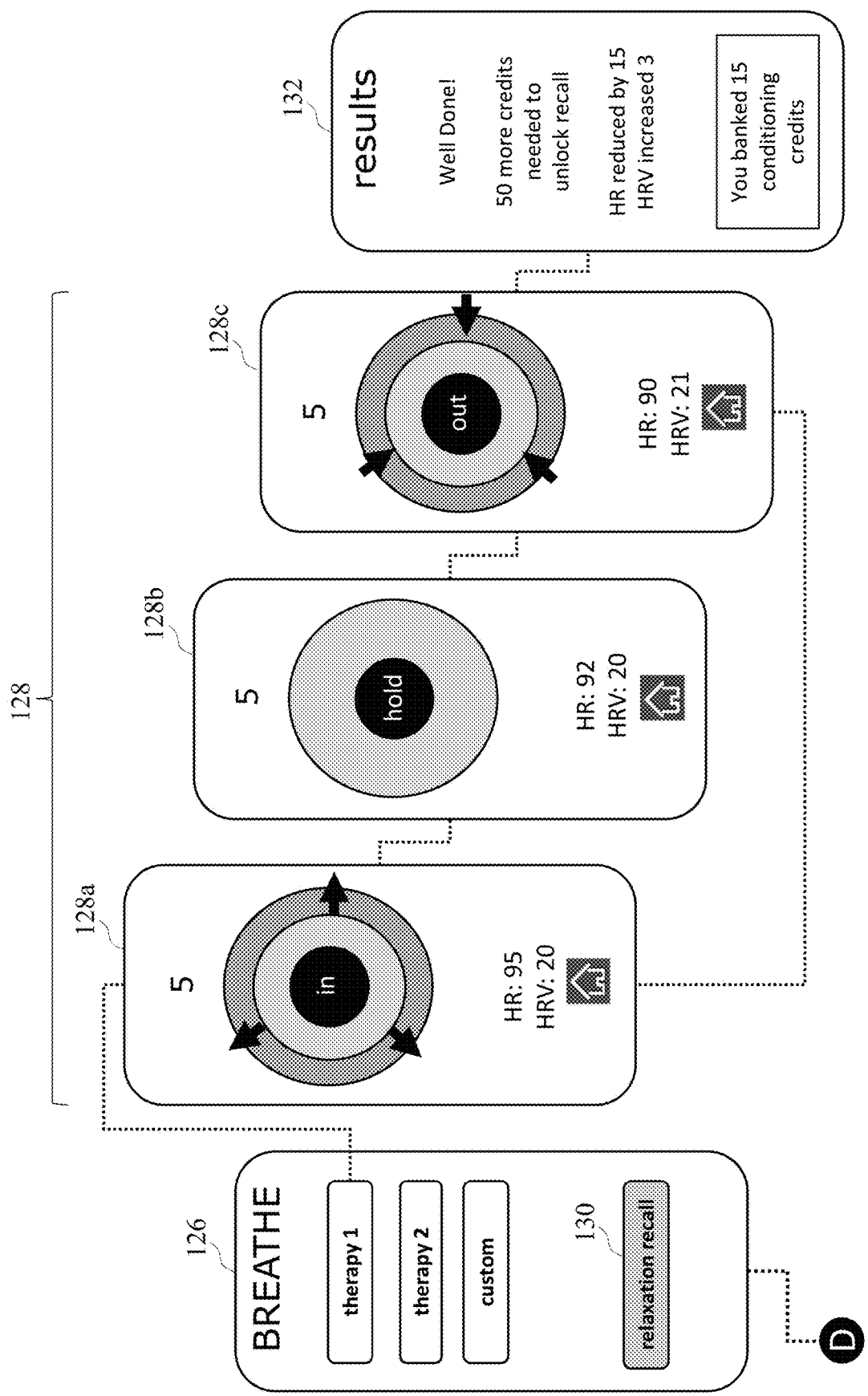
FIG. 13 illustrates an example set of screens output by the software application on the smart device to perform breathing therapy.

Referring back to FIG. 11, the home screen 100 includes a button 124 for "BREATHE". Selection of this button 124 causes the software application APP to display screen 126 shown in FIG. 13. On this screen 122, the user is presented with selectable breathing therapies that the user wishes to perform (also referred to as selectable breathing exercises or sessions). FIG. 13 shows two breathing therapies being selectable, plus the ability of users to customize a breathing therapy. Such customization, not shown, may enable the user to select the phases to be included in the breathing therapy, including inhaling, holding breathe after inhaling, exhaling, holding breather after exhaling, and any combinations thereof for the breathing therapy. The customization may also enable the user to select the amount of time for each of the phases, e.g., for each of inhaling, holding breathe after inhaling, exhaling, holding breathe after exhaling, and any combinations thereof for the breathing therapy. The customization may also allow users to set how many breathing cycles are to be performed during the breathing therapy.

Once the breathing therapy is selected/created, then the software application APP proceeds to screen 128 to show animations that visually depict each breathing cycle, including specific visualizations for all phases of the breathing cycle, e.g., inhaling, holding, exhaling, holding, etc. Screen 128 is represented in FIG. 13 by screen shots 128a-128c showing various stages of the animations. Screenshot 128a displays an inflating circle animation (see arrows indicating expansion of the circle) to represent the inhaling phase ("in"). Screenshot 128b displays a filled circle with the text "hold" to represent the holding phase. Screenshot 128c displays a deflating circle animation (see arrows indicating contraction of the circle) to represent the exhaling phase ("out"). A countdown timer could also be displayed (see the "5" on screenshots 128a-128c) to show how much time (e.g., in seconds) is spent for each phase of the breathing cycle. A separate countdown timer may also show how much time is spent for the entire breathing session. A counter could also be displayed to show how many breathing cycles are to be performed for the breathing therapy, which may count up as each cycle is completed. Values for heart rate and HRV, as measured by the wearable device 30 and transmitted to the smart device via the control system 82, could also be displayed in real-time on the screen 128 to show the user their improvement during breathing therapy (could also be shown during acupressure therapy or other therapy). The animations on screen 128 continue until the final breathing cycle for the selected/created breathing session is completed.

When the breathing therapy is selected/created, the software application APP also transmits a corresponding haptic waveform/file/data to the wearable device 30 to be output as vibrations by the wearable device 30 through the one or more haptic generators HPT in step with the breathing therapy. For example, the screenshots 128a-128c shows animations that visually depict inhaling, holding, and exhaling. Stored in memory on the smart device is a haptic waveform/file/data that corresponds to this breathing therapy, with the waveform/file/data having discrete components for each of the inhaling, holding, and exhaling phases of the breathing cycle. One such waveform that corresponds to the breathing therapy shown in FIG. 13 is shown in FIG. 6, with the separate inhale, hold, and exhale components of the waveform being output via the one or more haptic generators HPT in sync with the inhale, hold, and exhale animations. Thus, as the software application APP is displaying the animations on the screen 128, the wearable device 30 is generating vibrations to be felt by the user that coincide with the phases of the breathing cycle. The vibrations repeat for each breathing cycle in the breathing therapy. In some versions, the vibrations may repeat until stopped by the user via an input on the wearable device 30. Accordingly, users can be trained to perform breathing therapy via the vibrations alone, without the visual animations on the smart device. As a result, the wearable device 30 can be used without the smart device to guide the user through breathing therapy. For example, upon receiving a double tap input to wake the wearable device 30, and another double tap input to activate the one or more haptic generators HPT, the same vibrations that were used to train the user to perform breathing therapy, can now be used to haptically guide the user through the breathing therapy. This has the advantage of allowing users to be guided in their breathing therapy without needing their smart device. Of course, as previously mentioned, the wearable device 30 may also be a smart device and incorporate all the functions described herein for the smart device.

In some versions, the one or more sensors of the wearable device 30 may be used to monitor the one or more physiological parameters of the user to determine if the one or more physiological parameters are outside of threshold or normal values as described herein. The wearable device 30 may be configured to automatically activate the one or more haptic generators HPT to output the vibrations associated with the breathing phases to try to induce the user to perform breathing therapy and bring their physiological parameters back to within normal ranges. For example, if the controller 84 detects that the user's heart rate is exceeding a predetermined threshold (e.g., 90 bpm) or their HRV is below a predetermined threshold, and data from the accelerometer, gyroscope, and/or other inertial sensor connected to the controller 84 indicates that the user is not exercising, then the controller 84 may automatically activate the one or more haptic generators HPT to begin breathing therapy by generating the vibrations associated with the breathing phases of the last breathing therapy performed by the user to induce the user to begin breathing therapy.

Figure 14:
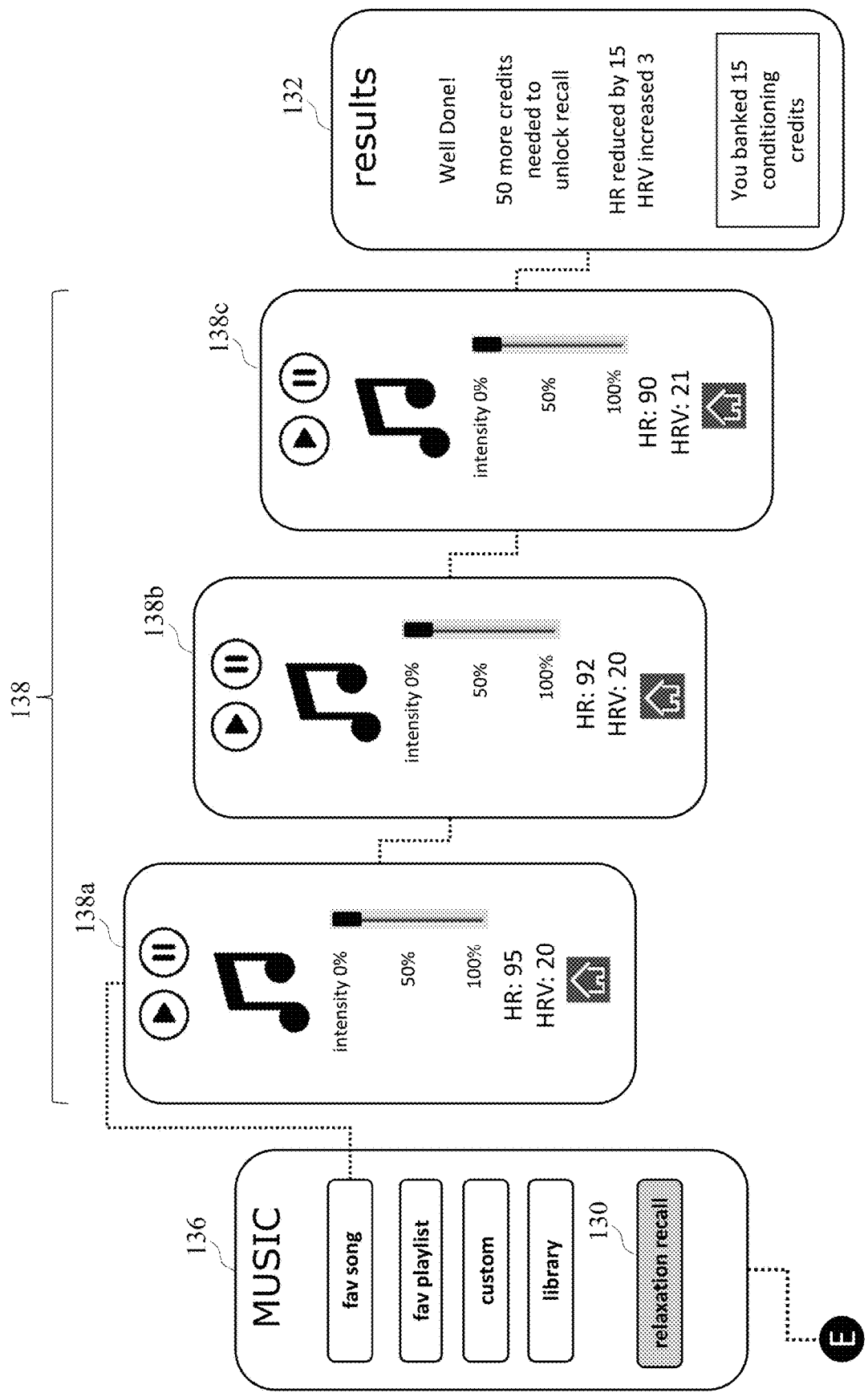
FIG. 14 illustrates an example set of screens output by the software application on the smart device to perform music therapy.

Referring back to FIG. 11, the home screen 100 includes a button 134 for "MUSIC". Selection of this button 134 causes the software application APP to display screen 136 shown in FIG. 14. On this screen 136, the user is presented with selectable songs that the user wishes to play through the smart device. These songs may be provided by the user's music app on their smart device (such as iTunes), streamed from other known music platforms, created by the manufacture of the wearable device 30, etc. The screen 136 shows that the user may store favorite songs, favorite playlists, etc., which would be identified on this screen 136, or the user may access a music library to select music to be played through the smart device, e.g., through the smart device speakers, headphones, etc. FIG. 14 shows a "fav song" and a "fav playlist" being selectable, plus the ability of users to customize music. Such customization, not shown, may enable the user to create music using the software application APP.

Once the music is selected/created, then the software application APP proceeds to screen 138 to allow the user to play/pause/stop the music through the speakers of the smart device, through headphones, etc. so that the user is able to hear the music in its original form. Screen 138 is represented in FIG. 14 by screen shots 138a-138c showing various stages of playing the music. Values for heart rate and HRV, as measured by the wearable device 30 and transmitted to the smart device via the control system 82, could also be displayed in real-time on the screen 138 to show the user their improvement during this music therapy. The animations on screen 138 continue until the music therapy is completed, which may be after the song finishes playing, after the playlist finishes playing, or after any other song or playlist, or other compilation of music finishes or is stopped by the user.

When the music is selected/created, the software application APP transmits a corresponding haptic waveform/file/data or associated audio file/data to the wearable device 30 to be output as vibrations by the wearable device 30 through the one or more haptic generators HPT in step with the music therapy. Stored in memory on the smart device is a haptic waveform/file/data or associated audio file/data that corresponds to each music selection. In some versions, the controller 84 may be programmed to "play" the audio files/data of the music selection, such as .wav files or .mp3 files, via the one or more haptic generators HPT. For example, ERM or LRA vibration motors can be driven with an audio signal or music files using the Haptic Feedback Evaluation Kit from Precision Microdrives Ltd. of London, England, which provides access to a haptic driver DRV2605 with an "audio-to-vibe" function used to create vibrations from audio sources.

As the software application APP is playing the music via the screen 138 and the music is being heard in its audible form via speakers, headphones, etc., the wearable device 30 is also generating vibrations to be felt by the user that coincide with the music. Accordingly, users can be trained to "listen" to the music via the vibrations alone, without playing of the music through one or more speakers. As a result, the wearable device 30 can be used without the smart device to provide a form of haptic therapy based on music. For example, upon receiving a double tap input to wake the wearable device 30, and another double tap input to activate the one or more haptic generators HPT, the same vibrations that were felt by user associated with the last music therapy session, can now be output to the user. This has the advantage of allowing users to receive music therapy, but through vibrations, and without needing their smart device. Of course, as previously mentioned, the wearable device 30 may also be a smart device and incorporate all the functions described herein for the smart device.

In some versions, the one or more sensors of the wearable device 30 may be used to monitor the one or more physiological parameters of the user to determine if the one or more physiological parameters are outside of threshold or normal values as described herein. The wearable device 30 may be configured to automatically activate the one or more haptic generators HPT to output the vibrations associated with the music to try to bring their physiological parameters back to within normal ranges. For example, if the controller 84 detects that the user's heart rate is exceeding a predetermined threshold (e.g., 90 bpm) or their HRV is below a predetermined threshold, and data from the accelerometer, gyroscope, and/or other inertial sensor connected to the controller 84 indicates that the user is not exercising, then the controller 84 may automatically activate the one or more haptic generators HPT to begin haptic therapy (derived from the music therapy) by generating the vibrations associated with the last music played by the user to induce the user to relax.

The wearable device 30 may also be used to condition users in a conditioning mode to associate a relaxed state with vibrations felt by the user. Such vibrations may be generated from a unique, predetermined, haptic waveform. For example, using classical conditioning principles, the vibrations generated from the unique haptic waveform (neutral stimulus) are paired with the acupressure therapy, breathing therapy, or music therapy (unconditioned stimulus) in the conditioning mode by activating the vibrations each time the user applies the projection 38 to the one or more acupressure points during acupressure therapy, each time the user performs breathing therapy, and/or each time the user performs music therapy.

Acupressure therapy using selected acupressure points, such as acupressure points P6, HT7, SP6, LV3, GB34, and/or others, breathing therapy, and music therapy, naturally results in the user achieving a relaxed state (an unconditioned response). The vibrations generated using the unique haptic waveform, when paired with the acupressure therapy, breathing therapy, or music therapy long/often enough, creates an association or link in the user's mind between the vibrations (the unique haptic waveform) and the acupressure therapy, breathing therapy, or music therapy. Conditioning sessions may be conducted at any time by using the wearable device 30 for self-administered acupressure therapy, breathing therapy, and/or music therapy. Conditioning of the user occurs through these forms of therapy by relaxing the user from an elevated stress state to a relaxed state. During a conditioning session, as the user is applying the projection 38 to certain areas of their body, as the user is performing guided breathing, and/or as the user is performing music therapy, whatever the case may be, the controller 84 activates the one or more haptic generators HPT to produce vibrations felt by the user based on the unique haptic waveform.

Such conditioning sessions may additionally, or alternatively, be initiated automatically in response to one or more physiological parameters of the user being outside certain thresholds or normal values, e.g., reaching, falling below, falling above, or exceeding certain threshold or normal values. For example, the conditioning session may be initiated automatically upon the controller 84 detecting the user's heart rate reaching or exceeding a threshold value (e.g., reaching or exceeding 85 beats per minute, 90 beats per minute, etc.) or the user's HRV reaching or falling below a threshold (e.g., reaching or falling below 20, 30, etc.) (e.g., indicating an elevated state of stress). In some cases, the thresholds or normal values may be discrete values or ranges of values. The thresholds or normal values may be user-specific and/or set by a therapist based on typical values of the user.

The wearable device 30 may also learn the thresholds or normal values in a learning mode that occurs before the conditioning mode. In the learning mode, the wearable device 30 may monitor the user for a predetermined duration, e.g., one day, one week, etc. and may then define the thresholds or normal values based on averages (e.g., average heart rate, average HRV, average blood pressure, etc.), based on low values, based on high values, based on predetermined offsets from the low values or the high values, based on look-up tables for similar users or groups of users, and the like.

The wearable device 30, or another device, can be used to confirm that the user achieved their relaxed state during each of the conditioning sessions, e.g., by measuring the user's heart rate, blood pressure, HRV, etc. with the one or more sensors previously described, and confirming that the user was relaxed from an elevated state of stress. Such confirmation may be useful to show that the user performed sufficient acupressure therapy, breathing therapy, or music therapy, such that it contributes to the conditioning described.

Activation of the conditioning mode may be triggered automatically when the user conducts the acupressure therapy, breathing therapy, and/or music therapy, such as when using the software application APP for guidance in performing the acupressure therapy, breathing therapy, and/or music therapy. The controller 84 may be programmed to prompt the user to perform conditioning sessions at the same time each day, multiple times throughout the day, or the like, or the user may choose when and where to conduct conditioning sessions. Conditioning sessions may occur through normal use of the wearable device 30 as well. Users may need to be reconditioned in the conditioning mode periodically to maintain the association or link and combat extinction of the conditioning.

Once conditioning is complete, e.g., after the user performs acupressure therapy, breathing therapy, and/or music therapy, for a suitable amount of time and/or sessions, a recall mode can be triggered to activate the one or more haptic generators HPT on the wearable device 30 and generate vibrations using the same unique haptic waveform that was used to generate vibrations in the conditioning mode. Now, even without the user performing further acupressure therapy, breathing therapy, or music therapy, the wearable device 30, through the vibrations felt by the user, can cause the user to achieve a relaxed state from an elevated state of stress. This occurs because the user's relaxed state they achieved during conditioning has become a conditioned response that can now be achieved simply by generating the vibrations from the same unique haptic waveform, owing to the conditioning of the user in the conditioning mode. The analogy is the case of Pavlov's dog, in which a dog associated ringing of a bell (neutral stimulus) with food (an unconditioned stimulus). The food (unconditioned stimulus) naturally made the dog salivate (unconditioned response), but by pairing the bell with the food, the dog eventually was conditioned to salivate (now a conditioned response) when the bell (now a conditioned stimulus) was rung without the food. In our case, the user naturally relaxes (unconditioned response) when performing the acupressure therapy, breathing therapy, or music therapy (unconditioned stimulus), but by pairing the vibrations from the unique haptic waveform (neutral stimulus) with the acupressure therapy, breathing therapy, or music therapy (unconditioned stimulus), the user is conditioned to relax (now a conditioned response) when the vibrations from the unique haptic waveform (now a conditioned stimulus) are generated and felt by the user, without performing further acupressure therapy, breathing therapy, or music therapy.

The conditioning mode may be carried out over several conditioning sessions, such as two, three, four, five, or more conditioning sessions. These conditioning sessions may last a few seconds, one minute, two minutes, five minutes, or longer. Once conditioning is complete, e.g., by measuring the total number, length, etc. of the conditioning sessions and comparing to a conditioning threshold, then the recall mode may be enabled for activation. In some versions, the recall mode may be disabled, e.g., the user input for activating it is disabled or ignored, until such time as the controller 84 determines that the user has completed conditioning in the conditioning mode. For example, conditioning may require a predetermined number and duration of conditioning sessions, e.g., conditioning could require at least three conditioning sessions and a total duration of conditioning of at least one hour. Other suitable numbers of sessions and/or total durations to complete conditioning are also contemplated. In some versions, the user may also manually enable or select the recall mode once the user is satisfied that suitable conditioning has been completed, i.e., the recall mode may always be unlocked.

One advantage such conditioning provides to the user is the ability to cause the user to relax simply by activating the vibrations from the same unique haptic waveform on the wearable device 30 in the recall mode via some form of input, e.g., user input such as the button 48, a separate button on the wearable device 30, double tapping on the wearable device 30, a touch screen button on the smart device provided via the software application APP, or the like. For example, the user may perform several acupressure therapy sessions with vibrations (also called acu-haptic therapy sessions) using the same unique haptic waveform to generate vibrations via the one or more haptic generators HPT, and thereby becomes conditioned to associate this unique haptic waveform (or the vibrations generated from it) with their relaxed state. Accordingly, vibrations from the same unique haptic waveform (now a conditioned stimulus) can be recalled in the recall mode via the "good vibes" selection of time period in FIG. 12 to cause the wearable device 30 to generate vibrations based on the same unique haptic waveform and cause the user to achieve their relaxed state from an elevated state of stress without having to perform any further acupressure therapy.

If the user performs several breathing therapy sessions using the same haptic waveform (see, e.g., the waveform of FIG. 6), and thus becomes conditioned to associate such vibrations from the haptic waveform with their relaxed state, then the same haptic waveform can be recalled in the recall mode via the "relaxation recall" button 130 on screen 126 of FIG. 13, which by its selection transmits the same haptic waveform to the wearable device 30 and causes the wearable device 30 to activate the one or more haptic generators HPT to generate vibrations associated with this haptic waveform, resulting in relaxation of the user, without having to perform further breathing therapy. The unique haptic waveform may be generated once, or multiple, repeated times in the recall mode. Similarly, if the user performs several music therapy sessions using the same haptic waveform (e.g., a waveform associated with music), and thus becomes conditioned to associate such vibrations from the haptic waveform with their relaxed state, then the same haptic waveform can be recalled in the recall mode via the "relaxation recall" button 130 on screen 136 of FIG. 14, which by its selection transmits the same haptic waveform to the wearable device 30 and causes the wearable device 30 to activate the one or more haptic generators HPT to generate vibrations associated with this haptic waveform, resulting in relaxation of the user, without having to perform further music therapy. The unique haptic waveform may be generated once, or multiple, repeated times in the recall mode.

The controller 84 can be programmed to weight "success" of conditioning based on how much certain physiological parameters improved, e.g., amount of decrease in heart rate, increase in HRV, etc. The controller 84 could further require an amount of conditioning in the conditioning mode, taking into consideration the weighted "success" of the acupressure therapy, breathing therapy, music therapy, or other mind-body intervention. For instance, a 5 bpm (beats per minute) reduction in heart rate could equate to a weighted factor of 0.8, while a 10 bpm reduction in heart rate could equate to a weighted factor of 1.0, whereby the controller 84 may require 5 conditioning sessions to complete the conditioning mode, and a session with a weighted factor of 0.8 only counts as 0.8 sessions, while a session with a weighted factor of 1.0 counts as 1 session. Completion of conditioning could also be based on points banked. Completion of conditioning could additionally, or alternatively, be based on other factors, such as the number of minutes, hours, days, etc. of conditioning, the number of interventions performed, the number of exercises performed, etc. Different configurations of therapy may have different results. For example, different breathing therapies may provide better or worse reductions in heart rate. The controller 84 may be programmed to identify which therapies work best and provide output to the user indicating which therapies work best after the user performs multiple types of therapy. This can be performed by an artificial intelligence engine backed by deep-learning algorithms.

Once conditioning is complete, then the user can activate the one or more haptic generators HPT in the recall mode to replay the same, unique haptic waveform to produce the vibrations to be felt by the user, without having to perform any further intervention, but while still receiving the same stress-reducing benefits that the therapy/intervention provides, owing to the conditioning of the user. In some versions, users may be required to bank a predetermined amount of points, tokens, currency, or some other form of conditioning credits before being allowed to activate the recall mode. The wearable device 30 may be configured to only vibrate when therapy is being conducted and thus is unable to vibrate alone (without accompanying therapy) until the user has the requisite amount of conditioning credits. Once the user has achieved the requisite conditioning (e.g., collected the predetermined amount of conditioning credits), the recall mode is unlocked and a therapy trigger (some form of user input on the wearable device 30 or a connected smart device), is enabled and activatable by the user to generate the same vibrations without requiring the user to perform therapy. The recall mode may be enabled for a predetermined period of time based on the amount of conditioning credits collected, and each activation in the recall mode may deplete the amount of conditioning credits until the user no longer has enough conditioning credits and has to perform additional conditioning sessions until they are once again conditioned—this helps to alleviate any extinction of the conditioning of the user, by effectively reconditioning the user. During reconditioning, different haptic waveforms could be generated to make reconditioning easier and avoid any potential issues with attempting to recondition the user with the same haptic waveform as the original conditioning.

The software application APP may also generate visual, audible, and/or haptic messages via the wearable device 30 or the smart device to acknowledge that the user performed the particular therapy, what the reduction in heart rate or increase in HRV was for the user, how many conditioning credits were banked, and how far the user is from unlocking the recall mode. For example, as shown in FIG. 13, after breathing therapy is complete, the software application APP generates messages on the screen 132 showing the user's results and how close the user is to unlocking the recall mode (e.g., unlocking the "relaxation recall" button 130). In some versions, the "relaxation recall" button 130 is always unlocked, but in some versions, this button represents the recall mode and is unlocked (and available for activation to cause vibrations without having to perform therapy) once the user has achieved enough conditioning credit. As shown, the results on screen 132 include text messages such as "Well Done!", "50 more credits needed to unlock recall", "HR reduced by 15", "HRV increased 3", and "you banked 15 conditioning credits". Other methods of gamifying the performance of therapy/interventions are also contemplated and are used to provide incentive for users to perform such therapy/interventions. For example, in some clinical settings, users may be required to perform a certain amount of therapy/interventions and creating some form of "credit" or "currency" that can be accumulated by the user for performing such therapy/interventions may inspire further use of the wearable device 30. Other events, activities, promotions, etc. could also be unlocked once a predetermined amount (number, time, etc.) of use of the wearable device 30 for performing therapy/interventions is performed. In some cases, health insurance premiums may be reduced based on the amount of therapy/interventions performed.

In some versions, there may be a correlation between the amount of time that the recall mode will be operable based on the amount of therapy performed, e.g., the amount of time or number of sessions that the user performed therapy. The controller 84 (either on the wearable device 30, the smart device, or both) can measure the amount of time the user performed acupressure therapy, breathing therapy, and/or music therapy by measuring the amount of time that the button 48 was activated and/or the time that the screens from the software application APP for these therapies was open. This can then directly correlate to the amount of time granted for the recall mode. For example, the user may be given 5 minutes of recall mode time for every 20 minutes of time spent performing acupressure therapy, breathing therapy, music therapy, etc. As another example, the user may be given 1 minute of recall mode time for every breathing session or music session. In some versions, this correlation may also take into account success of the therapy, e.g., was heart rate reduced by a threshold amount or HRV improved by a threshold amount—to ensure that the therapy was actually performed. This concept could also be applied to other forms of mind-body interventions.

In some versions, the user input for the recall mode, to activate the unique haptic waveform that was paired with the acupressure therapy, breathing therapy, and/or music therapy, in the one or more conditioning sessions during conditioning of the user, may be a separate user input device on the wearable device 30, the smart device, or both. As a result, the user can activate the recall mode via the wearable device 30 and/or smart device to generate the same unique haptic waveform used during conditioning to relax the user. In some versions, this user input may be one or more inputs displayed on the touch screen of the smart device, e.g., one button for 1 minute, 3 minutes, or 5 minutes, of activation in the recall mode. When one of these inputs is selected, the controller of the smart device communicates with the controller 84 on the wearable device 30 (e.g., via wireless communication via WiFi, Bluetooth, Zigbee, etc.) to activate the one or more haptic generators HPT to generate the unique haptic waveform and produce vibrations to be felt by the user for that selected amount of time. Other correlations between conditioning and recall can be used, as can other forms of recall triggers, time options, etc. In some cases, a separate button on the wearable device 30 can additionally, or alternatively, be used to activate the recall mode, or could be used to deactivate the recall mode. The button 48, which is aligned with the projection 38 centrally along an axis, could alternatively, or additionally, be programmed to activate and/or deactivate the one or more haptic generators HPT in the recall mode.

In some versions, only a single haptic generator HPT generates the unique haptic waveform for the conditioning mode and the recall mode. In some versions, multiple haptic generators HPT are used to generate the unique haptic waveforms. In some versions, the unique haptic waveform has a repeating vibration pattern owing to the haptic generator HPT being active for a first duration, at a predefined power level, and then being inactive for a second duration (the same or different than the first duration), and this pattern being repeated over and over until a conditioning/recall session is complete. The controller 84 is programmable to be capable of changing the waveform that is generated by the haptic generator HPT. The waveform may be such that vibrations are periodically felt by the user, i.e., the waveform periodically increases/decreases in amplitude, frequency, etc. The waveform may be an amplitude-modulated waveform with peaks of increased amplitude to resemble tapping on the user's skin. Different waveforms may be generated in an alternating pattern, or other pattern, etc. The waveform(s) may be generated for 1-10 seconds, or longer, or may be generated over 1 minute or more, such as when the waveform or different waveforms are periodically generated. The waveforms may cause vibrations that initially start with relatively high intensity (amplitude), but that then gradually decrease in intensity or taper over time. This decrease may be a linear decrease in intensity over time. The waveform(s) may be intended to affect nerve signals to the brain that cause stress/anxiety, nausea, and pain. Thus, the waveform(s) may also be those that are known to reduce or ease stress/anxiety, nausea, and pain.

The unique haptic waveform may mimic a breathing pattern of the user. For example, some relaxation techniques prescribe inhaling for five seconds and exhaling for five seconds to relax the user. Repeated patterns of activation and deactivation of the one or more haptic generators HPT may emulate such breathing patterns, e.g., by being active for five seconds and then inactive for five seconds. An amplitude-modulated waveform may also mimic such breathing patterns. Other patterns are also contemplated. In some cases, the vibrations generated by the one or more haptic generators HPT are consciously sensed by the user, i.e., the user can consciously feel vibrations caused by the haptic generators HPT on their skin. In some cases, the vibrations may be subtle and unable to be easily felt by the user, but nonetheless can be sensed by one or more mechanoreceptors of the user. In some versions, the vibrations are silent and can only be felt by the user, not heard. In some versions, the one more sensors of the control system 82 may be used to record a heart rate of the user which could then be used to select the frequency of haptic waveform, so that the vibrations are output in a pattern that feels like a heartbeat. In some cases, the one or more sensors may monitor a user over the course of a day, week, or the like, and determine a normal resting heart rate for that user, with the user's resting heart rate being used to select the frequency of the haptic waveform used to drive the one or more haptic generators HPT. As a result, when the user has an elevated heart rate (above resting heart rate), feeling vibrations that mimic their resting heart rate will tend to lower their current heart rate to lower levels. As these vibrations are felt during the mind-body intervention (e.g., during the acupressure therapy, breathing therapy, music therapy, etc.), and can be recalled after the intervention, the user can be conditioned to achieve a lowered heart rate in multiple, stressful situations.

In some versions, the waveforms may be created by the user, therapist, or by another. This can be done by recording the user, therapist, or other person with a microphone on the wearable device 30 or on the smart device. The controller 84 records an audio track of the user from voice signals output by the user, therapist, or other person, and received by the microphone, and then transforms the audio track into a haptic file for the one or more haptic generators HPT. The waveform may also be a song selected by the user or therapist with the associated audio file (e.g., .mp3, .wav, etc.) being converted to a haptic file and saved in the memory MEM of the control system 62 for playback through the one or more haptic generators HPT during the conditioning mode. In some versions, the controller 84 may be programmed to play audio files, such as .wav files, directly through the one or more haptic generators HPT, without first converting the audio file to a haptic file. One suitable software program for creating and playing such audio files is Audacity® 2.3.2 available through www.AudacityTeam.org. Suitable haptic generators HPT and controls therefor that can be used with this software program to generate desired waveforms include those available from Boreas Technologies Inc. In some versions, the same waveform may be employed for multiple users, or a unique haptic waveform may be employed for each user. In some versions, the user may be able to select one from a plurality of possible waveforms via the user interface UI.

Conditioning of the user can also be employed for other mind-body interventions that relax the user besides acupressure therapy, breathing therapy, or music therapy, such as for massage therapy, acupuncture therapy, energy therapy, psychological therapy, mindfulness techniques, meditation, and the like. In those cases, the wearable device 30 or any other suitable wearable device can be used to pair a unique haptic waveform with the mind-body intervention, e.g., the unique haptic waveform is activated to generate vibrations felt by the user during the massage therapy, during the acupuncture therapy, during the energy therapy, during the psychological therapy, during the mindfulness techniques, during the meditation, and the like to create the association in the user's mind between the vibrations of the unique haptic waveform and the mind-body intervention. After one or more conditioning sessions in the conditioning mode, the same unique haptic waveform can be recalled in the recall mode using any suitable user input to bring the user back to their relaxed state from an elevated state of stress.

Figure 15:
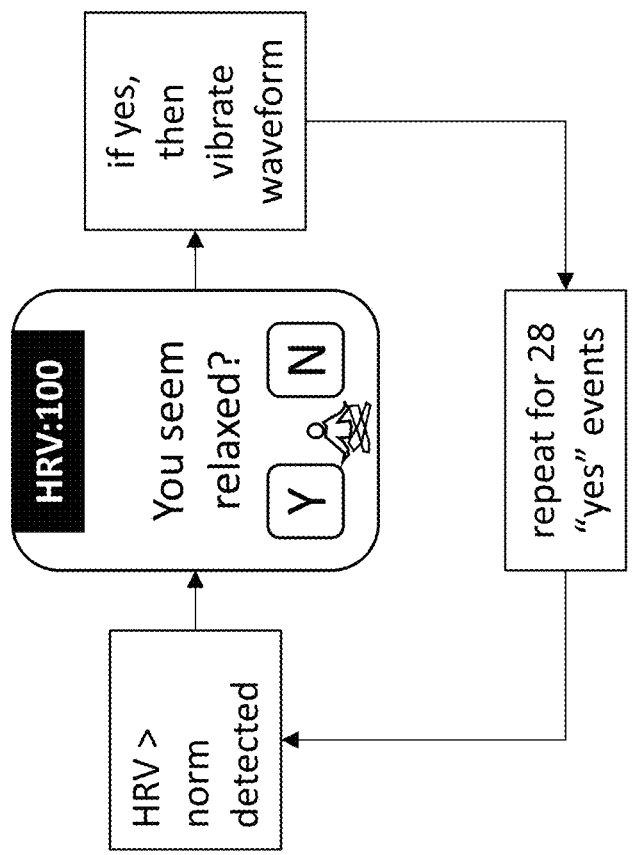
FIGS. 15, 16, and 17 are flow diagrams illustrating examples of steps to be performed using the wearable device.

In some versions, conditioning of the user in the conditioning mode may occur after a relaxed state is achieved, such as when the user has a low heart rate (compared to their normal heart rate), a good HRV (compared to their normal HRV), etc. In one example, shown in FIG. 15, the conditioning mode is carried out via a software application loaded on the wearable device 30. In this version, the wearable device 30 includes a touch screen display, like that on a smartwatch. The sensors carried by the housing unit 34 can measure the several physiological parameters (also referred to as biometrics) of the user. The controller 84, in this example, continuously monitors the user's heart rate and HRV via the sensors (e.g., every second heart rate measurements are taken and HRV calculated while the wearable device 30 is being worn). Other parameters could additionally, or alternatively, be measured as well.

After each measurement of heart rate and/or calculation of HRV, the controller 84 compares the measured and calculated values to baseline normal values of heart rate and/or HRV established for the user during the learning mode (e.g., an average heart rate and/or HRV for each day could be identified as the normal value for the user) or compared to predefined normal values for similar users that are stored in memory MEM. If the measured heart rate is less than the normal value (and/or equal to) and/or the calculated HRV value is greater than (and/or equal to) the normal value, the controller 84 automatically generates a message on the display such as "you seem relaxed?". The controller 84 also generates user input icons on the touch screen for the user to select (touch) corresponding to their answer "yes" or "no". If the user selects yes (which sends corresponding input to the controller 84 via the touch screen), then the unique haptic waveform for the user is generated by the one or more haptic generators HPT to be sensed by the user. The input could also be a simple push button or other user input on the wearable device 30, such as on the touch screen display, that the user is instructed to press whenever they feel relaxed, which then subsequently triggers the unique haptic waveform to be generated and sensed by the user. If the user selects "no", then the response is stored in memory MEM, but the unique haptic waveform is not generated (a different waveform could be generated in other embodiments).

Other messages may also be generated on the touch screen display, such as asking the user to "select your stress level", which the controller 84 also provides buttons labeled 1-5 (or more or less) that are selectable by the user and the associated input to be received by the controller 84 so that the controller 84 is able to analyze and store such input. If the user selects 1, then the controller 84 responds by generating the unique haptic waveform. If the user selects 2 or higher, then this is stored in memory MEM, but no haptic waveform is generated. In some cases, no messages are generated and the controller 84 automatically activates the one or more haptic generators HPT to generate the unique haptic waveform when the HRV is above the normal value.

This post-relaxation conditioning process is repeated for a predetermined period of time, a predetermined number of successful events, etc., e.g., 28 days or 28 events in which the user selects "yes". The goal is for the user to ultimately associate this unique haptic waveform with their relaxed state and this can be accomplished by conditioning the user over time through receiving this unique haptic waveform each time they indicate they are relaxed. If a relaxed state is detected by the controller 84 and a successful event occurs, this may cause the controller 84 to wait a predetermined amount of time before again repeating these steps. For example, if the user selects "yes", the controller 84 may generate the unique haptic waveform, but then wait for a predetermined period of time before asking the user again if they're relaxed, even if their heart rate is below normal and/or their HRV is above normal several times during that timeframe. The predetermined period may be a few hours, or even until the next day. The controller 84 may also be limited to certain timeframes in which to ask this question and generate the corresponding unique haptic waveform, such as during the evening, but not during normal sleep hours.

Figure 16:
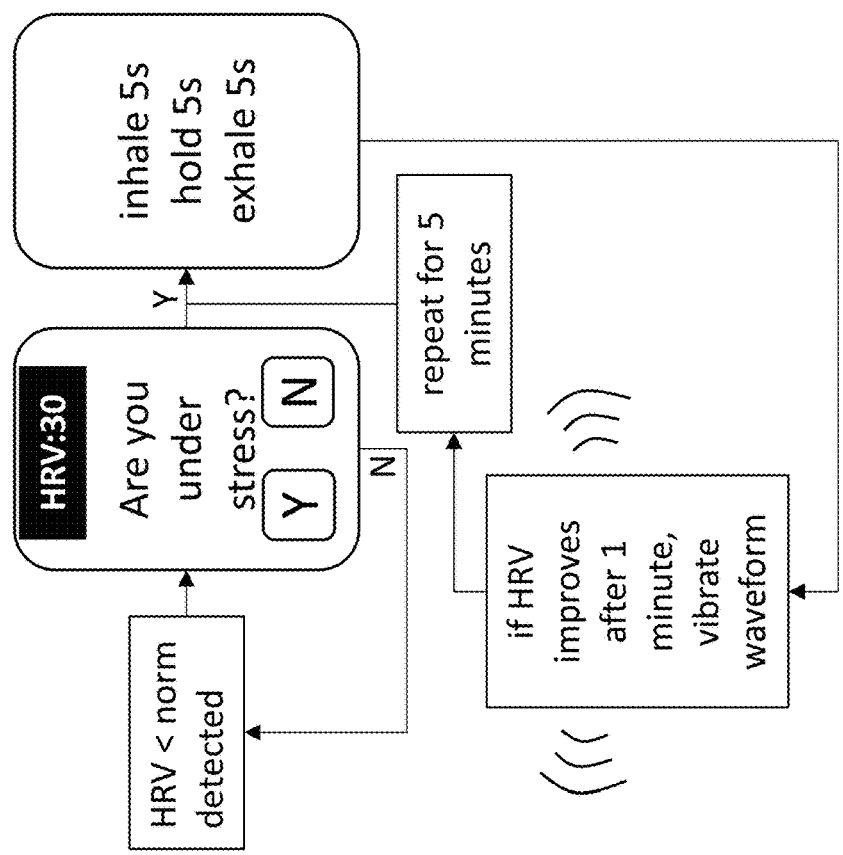

Once conditioning is completed, then the recall mode may be activated. In the example steps shown in FIG. 16, in the recall mode, when the user's heart rate is at or above normal (and the user is detected to be relatively sedentary, i.e., not exercising) and/or the user's HRV is detected to be below the normal value, then the controller 84 automatically generates a message on the display asking the user "Are you under stress" (or asking their stress level). If the user responds "Y" via the corresponding icon on the touch screen display, then this input is sent to the controller 84 to generate a second message on the display guiding the user through breathing therapy designed to decrease the user's heart rate and/or increase the user's HRV, as shown in FIG. 16 (e.g., inhale for 5 seconds, hold your breath for 5 seconds, exhale for 5 seconds). Other breathing therapies could also be employed. Visualization of such breathing phases as previously described could also be displayed on the wearable device 30.

The controller 84 then monitors the user's heart rate and/or HRV, presumably after they have completed the breathing therapy, to determine if the user's heart rate and/or HRV have improved after indicating they were under stress. This monitoring could continue for a predetermined monitoring time, such as 30 seconds, 1 minute, or longer. If after the predetermined monitoring period, the heart rate improves (e.g., the heart rate is lowered or lowered by 10% or more, or other calculatable improvement is determined), and/or the HRV improves (e.g., the HRV value is higher, the HRV value is higher by 10% or more, or other calculatable improvement is determined), then the controller 84 automatically activates the one or more haptic generators HPT to generate the vibrations based on the unique haptic waveform that the user was conditioned on in the conditioning mode. This additionally places the user in a relaxed state and acts as an enhancement to the breathing therapy. The predetermined monitoring time could be repeated every 30 seconds, 1 minute, etc. for a total of 1 minute, 2 minutes, 3 minutes, 4 minutes, 5 minutes, etc., with the unique haptic waveform being generated every time the heart rate and/or HRV is shown to improve via the calculatable improvement metric. For example, if the predetermined monitoring time is 30 seconds and is repeated for 2 minutes, then there are 4 monitoring periods and the unique haptic waveform could be generated 4 times if the heart rate and/or HRV measurably improve after each monitoring period.

Figure 17:
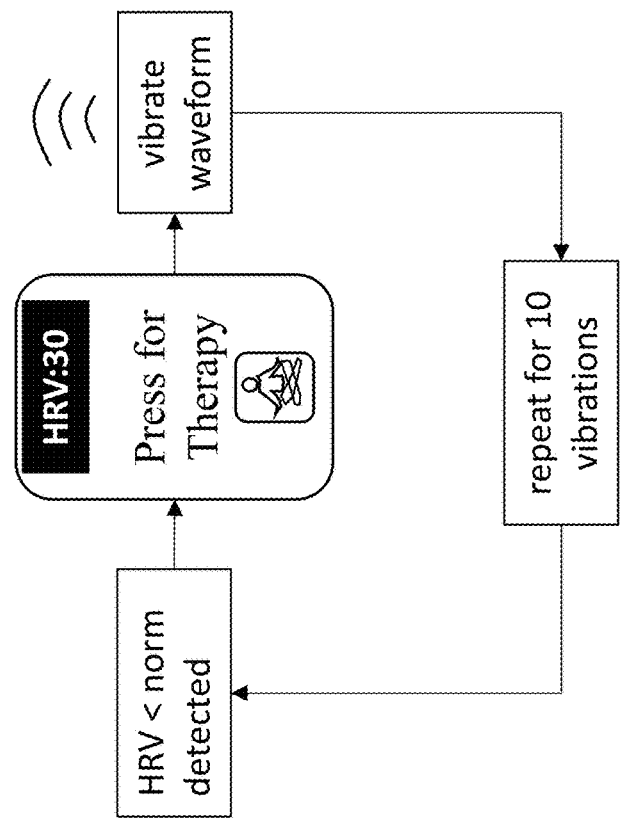

FIG. 17 shows another set of steps that could be employed in the recall mode. In this example, the steps are the same as in FIG. 16, except that the user is instead offered a recall button on the user interface UI to cause the controller 84 to activate the one or more haptic generators HPT to immediately begin generating the vibrations based on the unique haptic waveform that the user was conditioned on in the conditioning mode. In this example, the user is not guided through breathing therapy in combination with the haptic therapy and instead selection of the recall button (e.g., therapy trigger) by the user activates the vibrations for haptic therapy.

Imagine, for example, a child that has difficulty being separated from a parent and has an elevated state of stress as a result, but is provided the wearable device 30, with which the child has been conditioned to associate relaxation with vibrations of a unique haptic waveform to ultimately achieve a relaxed state with mere recall of the vibrations. The child can be conditioned by the parent using the acupressure therapy, breathing therapy, music therapy, or using other mind-body interventions (or other naturally relaxing interventions). That same child is now better equipped to be separated from the parent by being able to simply touch an input on the wearable device 30 to generate the same vibrations from the unique haptic waveform that placed them in a relaxed state. In that case, the child may be able to activate the recall mode all day long on their wearable device 30, and the parent may be required to recondition the child every night at bedtime via the conditioning mode.

Relaxation of the child could be bolstered if the unique haptic waveform was a waveform created from the parent's voice as previously described, such as creation of affirmations of love and affection, e.g., "I love you", into an audio file or haptic file to be played by the one or more haptic generators HPT. In that case, the wearable device 30 could be placed on the child's wrist, or other location, and the parent could speak "I love you" into the microphone on the wearable device 30, or into a microphone on the smart device (smart phone, smart watch, tablet, or the like) wirelessly connectable to the wearable device 30, and the child could immediately feel the vibrations of the associated haptic waveform generated on their wrist, or other location, owing to the voice-to-haptic creation being completed nearly instantaneously and the one or more haptic generators HPT being activated after receiving the spoken words in the microphone of the wearable device 30 or smart device. This further enables the child to face separation from the parent.

This configuration enables the wearable device 30 to communicate the affirmations of love and affection from parents or other loved ones to the child remotely, through the vibrations resulting from generation of the associated haptic waveform, such as when the child is at school, daycare, a friend's house, or anywhere the child needs the affirmation of love and affection so that they know they're safe. While the embodiments described herein for communicating affirmations of love and affection could be performed with the wearable device 30 described herein, other wearable devices could also be used, including any wearable device that has one or more haptic generators HPT coupled to a wearable support, which includes the one or more haptic generators HPT being embedded in the wearable support or disposed in a housing attached to the wearable support. As previously described, the wearable support could take several forms.

In some cases, a software application APP runs on the controller provided on the smart device that enables the loved one to say the affirmation of love and affection, e.g., "I love you", "I miss you", etc. into the microphone connected to the controller of the smart device so that the controller can save an audio file into memory connected to the controller. The audio file can be played and output directly to the one or more haptic generators HPT or the audio file can be first converted into a haptic file, such as an Apple Haptic Audio Pattern (AHAP) file, a .HAPT file, or other suitable file type. A MPEG-4 codec may be used to record and/or play back the audio files using Advanced Audio Coding (AAC) codec. Suitable file types may be, for example, .M4A and .MP4.

Figure 18:
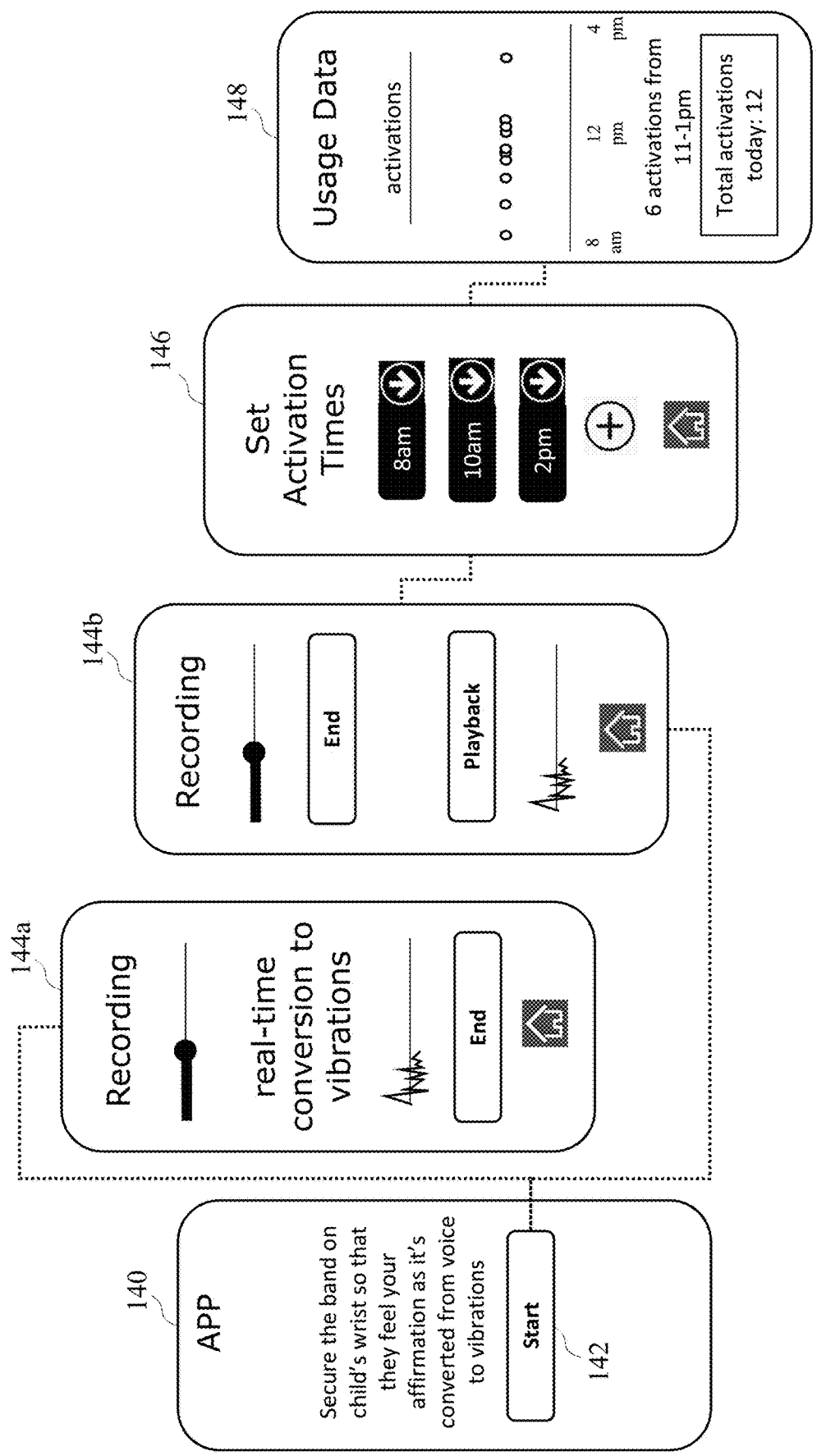
FIG. 18 illustrates an example set of screens output by the software application on the smart device to perform affirmation therapy.

Referring to FIG. 18, in some versions, a software application APP runs on the smart device, by including a home screen 140 on the display with a start button 142 to record the user's voice and create audio data, such as in the form of the audio file. In this case, the software application APP also includes instructions to secure the wearable device 30 to the child or other wearer because the haptic feedback may occur within 2 seconds or less of the user recording their voice affirmation (substantially simultaneously). As a result, the child or other wearer can feel the associated haptic feedback (vibrations) in nearly real-time with hearing the user's voice. As the user's voice is recorded, e.g., via the recording screen 144a generated by the software APP, the user's voice (e.g., the associated audio data/file or haptic data/file) can be substantially simultaneously transmitted (streamed) to the controller 84 to activate the one or more haptic generators HPT of the wearable device 30 via Bluetooth, Zigbee, WiFi, or other suitable wireless or wired connection. In some cases, as shown in the alternative recording screen 144b, an audio file is first fully created using the recording screen by recording the user's voice, then converted to haptic data/haptic file. Both the audio data/file and haptic data/file, which are both voice-related data, are thereafter played back simultaneously via the software application APP so that the child or other wearer simultaneously hears and feels (via the vibrations from the wearable device 30) their loved one's affirmation of love and affection. Audio recordings from the user may be a few seconds in length, or may be longer, and may include simple one- or two-word phrases, or longer messages. In some versions, the software application APP may set a maximum message length to ensure suitable battery life from the wearable device 30. In some versions, the controller 84 may be programmed to "play" audio data/files, such as .wav files, through the one or more haptic generators HPT.

Although voice input is being recorded in the version shown in FIG. 18, heartbeat data from the parent (or other person) could additionally, or alternatively, be recorded via the one or more sensors previously described, or via a camera on the smart device. The heartbeat data could then be converted into a pulse width modulated (PWM) signal with a frequency that matches the parent's heartbeat in beats per minute (bpm), and with a magnitude that could be set by the parent via the software application APP. The magnitude could also be set by the software application APP to be a predetermined percentage of maximum amplitude capable of output by the one or more haptic generators HPT, or some other specification of output. The heartbeat data/signal could subsequently be sent to the wearable device 30 for playback to the child via the one or more haptic generators HPT, at preselected times set by the parent, upon request by the child, or combinations thereof. In some versions, both the affirmation and the parent's heartbeat could be converted into audio/haptic data to drive the one or more haptic generators HPT, either simultaneously, or sequentially. In some cases, one haptic generator HPT could playback the audio/haptic data/signal associated with the heartbeat, while another haptic generator HPT could playback the audio/haptic data/signal associated with the voice affirmation. In some versions, the heartbeat data could also be slowed such that the audio/haptic data/signal to be sent to the wearable device 30 is slower than the parent's current heart rate, so that the associated vibrations felt by the child reflect a calmer heart rate. The audio/haptic data/signal could also be based on an artificial heart rate typically associated with a calm/relaxed state.

The affirmation and/or heartbeat, i.e., the associated audio/haptic data and corresponding waveforms, are stored in memory MEM connected to the controller 84 of the wearable device 30 for later recall by the child (or other user) by simply activating a user input, such as a button or other user input. In some versions, the wearable device 30 may include a separate user input, such as a button for recalling the parent's heartbeat separate from the parent's affirmation.

The audio/haptic data/waveforms may remain in storage in the memory MEM on the wearable device 30, until replaced by a new affirmation/heartbeat, which can be provided by the user of the smart device at any time upon connection to the wearable device 30. As a result, the child can recall the affirmation/heartbeat and feel the associated vibrations, even when remote from the parent, and without requiring any WiFi, cellular, or any other network connection. In some versions, the wearable device 30 may support WiFi connectivity, cellular communication, or the like. This may enable communication between the smart device of the parent and the wearable device 30 over a network, through cellular communication or the like. In this case, the parent can speak further messages into the smart device that can then be converted as described herein, into audio/haptic data that is subsequently felt by the child via the network connected wearable device 30. Such messages can be delivered in near real-time, as with current communication technology.

Conversion of audio data, such as a digital audio signal, to haptic data, such as a haptic signal can be carried out in the manner shown in U.S. Pat. No. 8,717,152, hereby incorporated herein by reference. The audio/haptic data may also be electronically filtered using low/high pass filters to remove certain frequencies, such as any frequency above 200 Hz, above 100 Hz, or above 20 Hz, such that the haptic waveform fed to the one or more haptic generators 46 has a frequency range of from 0-200 Hz, from 0-100 Hz, from 0-20 Hz or some other suitable range of acceptable frequencies that produce a relaxing or calming effect on the user of the wearable device 30 when played. Men and women typically speak in different ranges, men typically from 85 to 155 Hz and women typically from 165 to 255 Hz. It may be beneficial for the haptic frequency used to generate the vibrations felt by the child be at a relatively low frequency. For this reason, it may be helpful to instruct the parent, via the display, to speak softly into the microphone when providing their affirmation and/or to filter out high frequencies. Also, in some versions, the entire audio/haptic waveform may additionally, or alternatively, be adjusted via the controller 84 and/or filtered to equally reduce the frequencies across the waveform so that the highest frequency is below a predetermined value, such as all below 100 Hz, 50 Hz, etc.

Playback of the audio and/or haptic files simultaneously, e.g., audio on the smart device and audio/haptics on the wearable device 30, can be performed multiple times so that the child is fully conditioned to associate the vibrations on their wrist with the audio of the parent's affirmation. In some cases, instructions may be generated by the controller and displayed on the display to instruct parents to repeat playback 2, 3, or more times. Thus, these can be considered conditioning sessions in the conditioning mode as previously described in which the child is trained/conditioned to associate a neutral stimulus, such as the vibrations, with their parent's affirmation of love and affection.

Later activations of the wearable device 30 to generate the vibrations occur in the recall mode. In some versions, the user input (e.g., switch and button) of the wearable device 30 is only operational to generate vibrations once the parent has programmed an audio/haptic waveform/file into the wearable device 30 via the software application APP. In some versions, the controller 84 of the wearable device 30 may be programmed so that a single press of the button 48 plays back the entire audio/haptic file that was created from the parent's voice a single time, such that multiple presses of the button 48 plays it back multiple times in series. In other words, two more successive pushes of the button 48, even if within 2-3 seconds, would result in the same number of playbacks even if each one lasted several seconds, such as 5-10 seconds. In some versions, a single press may play back the entire audio/haptic file multiple times. Activation of a separate user input on the wearable device 30, such as a separate switch and button may separately playback the parent's heartbeat for a preselected period of time, such as 1 minute, 2 minutes, etc. This period of time may be set by the parent via the software application APP.

In some cases, the wearable device 30 may have a clock connected to the controller 84 to monitor time. Users of the smart device, such as a parent, can then select one or more times throughout the day that the controller 84 of the wearable device 30 will activate the one or more haptic generators HPT. In other words, the wearable device 30 can be configured to automatically activate the audio/haptic waveform and generate associated vibrations at predetermined times to be felt by the child, such as times when the loved one knows the child may be suffering from high levels of separation anxiety. This can be based on the feedback data described below. As shown in FIG. 18, the software application APP may provide an input screen 146 on the smart device to select/set days/times in any of various ways known to set days/times, such as common calendar entry formats for appointments or events.

The software application APP may also be programmed to provide feedback data, such as usage data to the user of the smart device, such as a parent, loved one, etc. Such feedback data may come in various forms, including charts, text, etc. For example, the feedback data may include the controller 84 of the wearable device 30 tracking and storing in memory MEM each activation of the wearable device 30 and associated time, and then plotting those results on a graph as shown on the usage screen 148 in FIG. 18. This may give the parent an idea of when the child is most anxious or nervous and the parent can then more accurately isolate events or situations that seem to be contributing to this stress. Total activations in each time period may also be captured and reported. In embodiments where the wearable device 30 includes one or more physiological sensors, this feedback data may also be correlated to physiological data stored in the memory of the wearable device 30 and later transmitted to the smart device, such as heart rate data, heart rate variability data, blood oxygen data, temperature data, and the like, so that parents can see how physiological changes correlate to their child's need to activate the wearable device 30. The embodiments described could also be applied to a single parent sharing an affirmation with multiple children by connecting multiple wearable devices 30, one for each child, to the parent's smart device, and then transmitting the same audio file or haptic file to all the associated wearable devices 30.

In some cases, the wearable device 30 and/or the smart device includes one or more speakers so that the software application APP is able to play soothing audio through the speakers, while simultaneously generating the vibrations to be felt by the user via the one or more haptic generators HPT of the smart device. For instance, if the user launches a software application on the smart device for meditation or mindfulness and selects a user input option for "stress relief", then the controller on the smart device may simultaneously output the soothing audio stored in memory MEM connected to the controller (or streamed from another service) through the speakers and the user's mimicked heart beat may be output via the one or more haptic generators HPT of the smart device. The user could then place the smart device on their chest so that the vibrations are felt through their chest to enhance relaxation. In some cases, if the resting heartbeat waveform is used to generate the vibrations, and the user is experiencing an elevated heart rate at the time, placing the smart device on their chest will cause the user's heart rate to reduce and come into tune with their resting heart rate.

In some versions, the wearable device 30 includes a display unit that includes a display. The display may simply display the time of day, or any other information as described herein, and may be an interactive touch screen display for receiving user input. The display unit may be powered by a separate battery from the battery used to power the one or more haptic generators HPT and the sensor system. The display unit may be configured to be located diametrically opposed from the projection 38 so that users can easily align the projection 38 with acupressure point P6 when wearing the wearable device 30. It can also show users, such as child users, the times that the wearable device 30 has been programmed to replay their parent's affirmation of love and affection. In some cases, the display may also display a text message and/or photo along with the replayed affirmation of love and affection, such as a text message that matches the affirmation of love and affection, so that it is reinforced. In other words, when the button 48 is pressed, or at the preselected times, the one or more haptic generators HPT are activated to vibrate in the pattern that the child has been conditioned to associated with the parent's voice input of their affirmation, and the display simultaneously shows a text version of the affirmation written out across the display. Again, the text and vibrations can occur without the wearable device 30 being connected to any network, as the wearable device 30 was preprogrammed with the affirmation to playback on request or at certain times. Of course, in some cases, such as when the wearable device 30 is connected to a network, then real-time messages could be transmitted to the controller 84 of the wearable device 30, including text messages and voice messages converted into haptic data used to drive the one or more haptic generators HPT.

Figure 19:
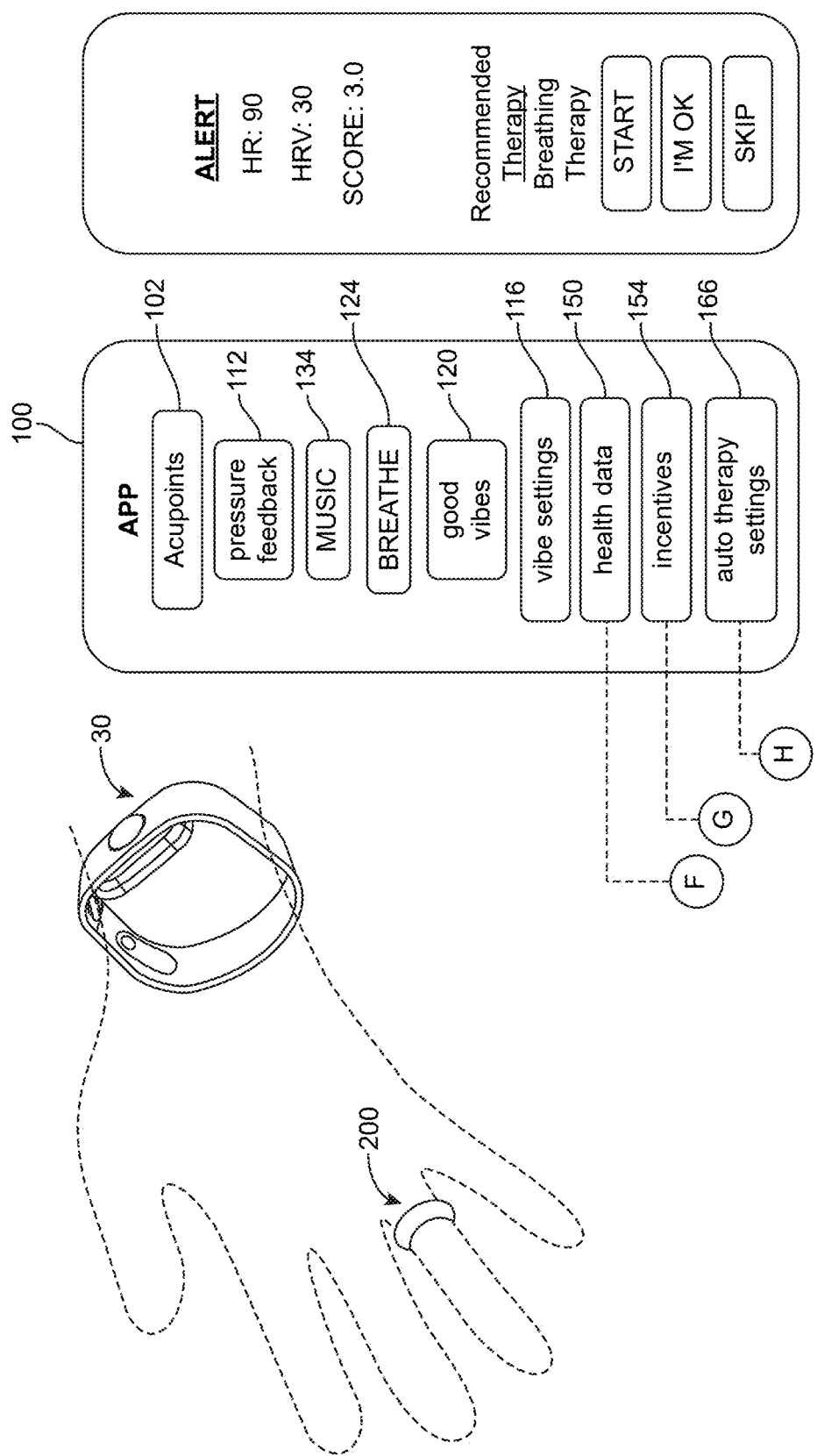
FIG. 19 illustrates another example set of screens output by a software application on a smart device.
Figure 20:
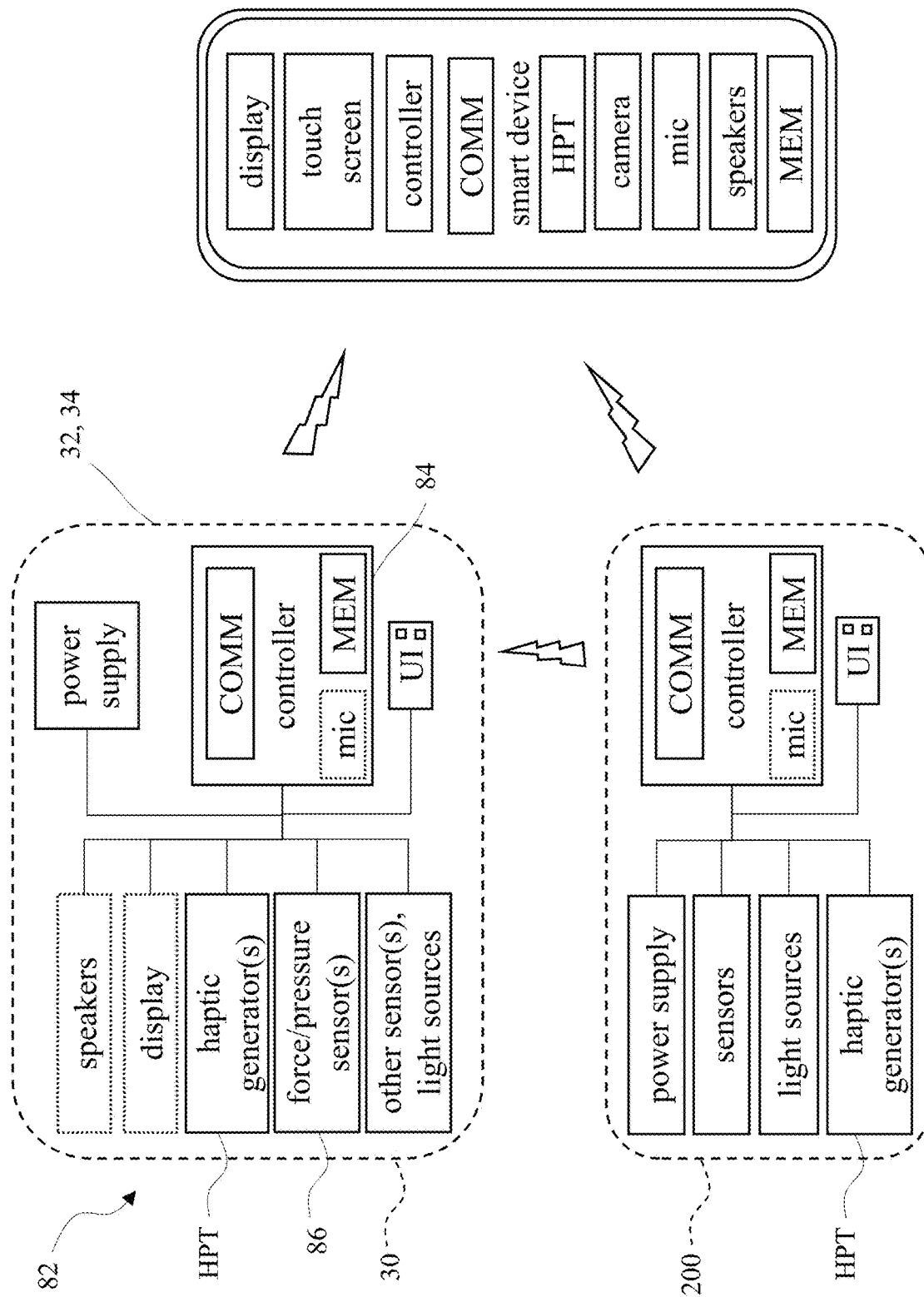
FIG. 20 is a block diagram of another control system.

Referring to FIGS. 19 and 20, a separate wearable device 200 may be provided to measure the one or more physiological parameters of the user as described herein, and may be considered a health wearable. The wearable device 200 may be equipped with all the same components described herein for the wearable device 30, except that the wearable device 200 may lack any massage heads for performing acupressure therapy. In the version shown, the wearable device 200 is a ring/finger band worn on a finger of the user to monitor one or more physiological parameters of the user, such as heart rate, HRV, body temperature, blood pressure, ECG, EKG, glucose, etc. The electronic components described herein are disposed inside a housing of the ring/finger band. The wearable device 200 is able to communicate with the smart device in the same manner as the wearable device 30, and may also be configured to communicate with the other wearable device 30. In some versions, the wearable device 200 may be an Oura Ring sold by Oura Health Oy or Ouraring Inc. of Oulu, Finland.

In some versions, the smart device or the wearable devices 30, 200, or all of these, may calculate values for a stress-related parameter/metric based on the measured physiological parameters and then display such values and/or changes in such values that result from performing any of the therapies described herein. For example, the stress-related parameter/metric may be a stress metric SCORE that is calculated based on heart rate, HRV, and/or body temperature, and that takes into account the user's movement as measured by one or more of the inertial sensors described herein. In other words, the inertial sensor can detect accelerations in any direction that rise above a threshold value indicative of excessive movement likely caused by exercising, e.g., running or other cardio activity that requires movement, and thus the software application APP would be able to neglect or otherwise adjust for such heart rate or HRV values when calculating the stress metric SCORE. In some versions, the stress metric SCORE is based on the following formula: SCORE=(heart rate/HRV)*(body temp./98.6), and can be configured by the controller 84 of the smart device to only be calculated when values of acceleration measured by the one or more inertial sensors in Ax, Ay, Az directions are less than the threshold values for a threshold period of time, such as less than 10.0 ms$^{-2}$ in each of the directions, or less than 3.0 ms$^{-2}$ after zeroing for gravity compensation, for at least 5 minutes. As an example, if the user's heart rate is 90 bpm, their HRV is 30 ms, and their body temperature is 98.6° F., then their stress metric SCORE=(90/30)*(98.6/98.6)=3.0. In some versions, the stress metric SCORE is based on heart rate, HRV, body temperature, ECG, EKG, O2 readings, and/or blood pressure, or any combinations of these values. In some versions, the stress metric SCORE=(heart rate/2)/(HRV/2). So for a heart rate of 95 bpm and an HRV of 30, the stress metric SCORE=(95/2)/(30/2)=3.2.

In some versions, the one or more sensors of the wearable devices 30, 200 may be used to monitor the one or more physiological parameters of the user to calculate the user's stress metric SCORE so that the controller 84 can determine if the user's stress metric SCORE is outside of/meets threshold or normal values as described herein. For example, normal values may range from 0.0-1.5, indicating low stress, 1.5-2.5 indicating medium stress, but higher stress values may be 2.5-3.0 or higher. Other values for the stress metric SCORE that indicate an elevated state of stress are also contemplated.

The wearable device 30, 200 and/or the smart device may be configured to automatically activate the one or more haptic generators HPT on the wearable device 30 to output the vibrations associated with one of the therapies described herein to try to bring their stress metric SCORE back to within normal ranges, and/or to bring the one or more physiological parameters back to within normal ranges. For example, if the controller of the smart device detects that the user's stress metric SCORE is exceeding/meets a predetermined threshold (e.g., 2.5), and data from the accelerometer, gyroscope, and/or other inertial sensor connected to the controller 84 of the wearable device 30, 200 indicates that the user is not exercising (or otherwise excessively moving), or has not been exercising for at least a threshold amount of time (e.g., for 5 minutes or more), then the controller of the smart device (and/or any of the controllers) may automatically activate the one or more haptic generators HPT to initiate breathing therapy, music therapy, and/or vibration therapy. For example, the controller 84 of the wearable device 30 may automatically activate the one or more haptic generators HPT to begin generating the vibrations associated with the last therapy performed by the user, e.g., breathing therapy, music therapy, and/or vibration therapy, in response to an activation signal from the controller of the smart device. Once a therapy is automatically activated, then the display of the smart device may automatically be switched to showing a visual/text representation of the real-time values of the stress metric SCORE, heart rate, HRV, etc., along with initial values of these variables at the time of the alert. The display may also show text/visual representations of improvement of one or more of these variables over time.

In some versions, if the controller of the smart device and/or the controller of the wearable device 200 detects that the user's one or more physiological parameters, e.g., heart rate, HRV, etc. are outside/reach predetermined thresholds (e.g., above 90 bpm, below 30 ms, etc.) as measured by the wearable device 200, and data from the accelerometer, gyroscope, and/or other inertial sensor connected to the controller 84 of the wearable device 30, 200 indicates that the user is not exercising (or otherwise excessively moving), or has not been exercising for at least a threshold amount of time (e.g., for 5 minutes or more), then the controller of the smart device (and/or any of the controllers) may automatically activate the one or more haptic generators HPT to initiate breathing therapy, music therapy, and/or vibration therapy. Thus, in some versions, the wearable device 200 is provided to measure the one or more physiological parameters of the user, the wearable device 30 provides therapy to the user via vibrations from the one or more haptic generators HPT based on measured values of the one or more physiological parameters or metrics calculated therefrom, and the smart device acts as a hub for running the software application APP to display information to the user, calculate/display stress-related metrics and/or display values of the measured physiological parameters/stress metrics, and/or for receiving input from the user.

In some cases, users may desire for automatic therapy to only be initiated once or twice a day to limit the amount of therapy performed. Users may also set the days/times that automatic therapy may be initiated, such as during the morning, afternoon, set time periods, etc. Setting of the days and/or times that automatic therapy is operational may be done via the software application APP, such as in a settings screen or the like. In some versions, the controller of the smart device may be programmed to monitor the user's physiological parameters and stress metric over a threshold period of time, such as one day, one week, one month, etc. in the training mode to determine trends of values for such parameters/metrics and to isolate daily/weekly/monthly lows, averages, and highs. As a result, the controller may store such information in the memory and determine the lows, averages, and highs for each parameter/metric in the training time period, and thereafter base activation of the automatic therapy on such information. For example, if after a week of operation in the training mode, the controller identifies that the stress metric SCORE had a high of 2.8, the controller may then set 2.8 as the threshold to meet to activate the automatic therapy. In other words, after the training mode, the controller of the smart device and/or the controller 84 of the wearable device can set and store in memory MEM 2.8 for the stress metric SCORE threshold to be reached before automatically activating the one or more haptic generators HPT. Additionally, in some cases, the user can view the data stored from the training mode, and may be prompted by the software application APP to do so, and can thereafter approve/confirm the set threshold to be set by the controller. Similarly, during the training mode, the controller of the smart device can generate prompts via the software application APP when stress-indicative values of the parameters/metrics are reached that ask the user whether they are "okay", "stressed", "not stressed" or to select a level of stress from 1-3, 1-10, etc. This additional information can be used by the controller of the smart device to determine the threshold for automatic therapy. For instance, if the stress metric SCORE reaches 2.5, but when prompted on the software application APP, the user is asked to rate their stress from 1-10 and they select 2, then 2.5 may not a good threshold for that user. Instead, if the user rates their stress at 8, then this may be a good threshold for the user. The software application APP can be programmed to identify 8 or higher, for example, as a suitable response from the user to set the stress metric SCORE of 2.5 as the threshold.

As shown in FIG. 19, instead of automatically initiating therapy, or in addition to, the software application APP may also provide a visual indication to the user on the display of the smart device to alert the user that they have a heart rate HR, HRV, and/or stress metric SCORE outside their normal ranges, even though the controller of the smart device has determined that the user has not exercised for at least a threshold amount of time. The software application APP may also recommend one of the therapies for the user based on the measured success of each of the therapies. This may include a visual alert on the display of the smart device stating "ALERT" for example, to alert the user that they may need to conduct one or more of the therapies provided by the wearable device 30. In some versions, the software application APP may monitor heart rate, HRV, body temperature, stress metric SCORE, etc. when each of the various therapies are being performed and can determine which therapy is the most successful for the user in improving such values, e.g., in improving heart rate, HRV, body temperature, stress metric SCORE, or any combination of these. The software application APP may also be able to provide a ranking or score for each of the therapies to the user based on their improvement levels so that the user is able to see which therapy is most useful in reducing their stress, such as a relative ranking of 1, 2, 3, etc. for each of the therapies with 1 being the best. Such ranking could be based on the percentage of improvement in heart rate, HRV, and/or stress metric SCORE resulting from performance of the therapy and could also be adjusted based on time. For example, each therapy may be given a percentage heart rate improvement/time, e.g., 1.2% reduction/minute, 2.3% reduction/minute, etc. with the best rate being given the top rank. In FIG. 19, breathing therapy is recommended by the software application APP and the user has three buttons to select from, (i) to start the breathing therapy "START" (ii) to indicate that they don't need the therapy "I'M OK"; or (iii) to skip the therapy "SKIP". If the "START" button is selected, then the vibrations for breathing therapy are triggered and breathing therapy continues based on the previously used breathing cycle. If the "I'M OK" button is selected, then no therapy is triggered and the controller of the smart device saves this event as a non-stress event and stores the values of heart rate, HRV, and the stress metric SCORE for this non-stress event so that the controller can account for these values in determining when it is appropriate to generate alerts to the user. For example, if the stress metric is 2.5, but the user chooses "I'M OK", then the controller now knows that alerts should only be generated if the stress metric SCORE is above 2.5. If the "SKIP" button is selected, then this event is ignored and it's assumed that the user is experiencing stress but unwilling to perform any therapy at the moment. If no button is selected within 5 minutes, then the software application APP is automatically closed and the system treats this as a "SKIP" input.

Referring to FIG. 19, in the version shown, the home screen 100 includes an additional button 150 for "health data". Selection of this button 150 causes the software application APP to display screen 152 shown in FIG. 21. On this screen 152, the user is presented with health data, such as data relating to current heart rate, HRV, stress metric SCORE, and/or any other health-related data (e.g., ECG values, O2 values, EKG values, body temperature, glucose readings, etc.). Values for this data may come from sensors of the wearable device 30 or from the wearable device 200. Trends of any of the parameters may also be shown over time, with indications of when therapy was performed by the user (see black circles). The controller 84 of the wearable device 30 may be able to track when therapy was performed based on operation of the one or more haptic generators HPT. In some versions, whenever the one or more haptic generators HPT are active, the controller 84 stores time stamps for such active states and saves these as therapy events that are then logged and displayed here or elsewhere on screens of the software application APP. Each black circle may also be a button that is user-selectable to show details of the therapy events, such as length of therapy, type of therapy, initial heart rate, HRV, stress metric SCORE, etc. when therapy started and when therapy ended, and the results of therapy, such as changes in heart rate HR, HRV, stress metric SCORE, and the like.

Referring to FIG. 19, in the version shown, the home screen 100 includes an additional button 154 for "incentives". Methods of gamifying or incentivizing the performance of therapy/interventions are contemplated and are used to provide incentive for users to perform such therapy/interventions. For example, users may be required to perform a certain amount (e.g., number) of therapy/interventions and thereby create some form of "credit" (e.g., "currency") that can be accumulated by the user for performing such therapy/interventions and this may inspire further use of the wearable device 30. Other events, activities, promotions, etc. could be unlocked once a predetermined amount (number, time, etc.) of use of the wearable device 30 for performing therapy/interventions is performed. In some cases, health insurance premiums may be reduced based on the amount of therapy/interventions performed.

The controller of the smart device can be programmed to consider "success" of a particular therapy based on how much certain physiological parameters or the stress metric SCORE improved, e.g., amount of decrease in heart rate, increase in HRV, reduction in stress metric SCORE, etc. The controller could further determine the amount (e.g., number) of credits to award based on "success" of the therapy, e.g., acupressure therapy, breathing therapy, music therapy, vibration therapy, or other mind-body intervention. For instance, a 5 bpm (beats per minute) reduction in heart rate during therapy could equate to the controller awarding 5 credits to the user, while a 10 bpm reduction in heart rate could equate to the controller awarding 10 credits to the user. If there is no corresponding improvement during therapy, then no credits are awarded. Credits could also be based on changes in the stress metric SCORE (e.g., reductions of 0.1 generates 10 credits, so a reduction of 0.4 would generate 40 credits, etc.). Awarding credits based on the stress metric SCORE has the added benefit of avoiding users cheating the system by exercising first to raise their heart rate. Of course, the inertial sensors could be used by the controller to track user movement and the software application APP may require the user to be relatively still for a threshold amount of time before therapy is counted for credits, regardless of which metric is being used to determine credits to be awarded.

Credits may be awarded based on any form of therapy "success" such as improved values, % of improvement over initial values, etc. Any suitable method for awarding therapy credits based on therapy success is contemplated herein. In some versions, credits may be awarded to users for simply performing the therapy, independent of the success of the therapy, and/or in addition to the success of the therapy. In some versions, each performance of therapy may result in 1 or more credits being awarded. In some cases, different forms of therapy may be given different weights in terms of the amount of credits awarded for success during therapy. For example, a 5 bpm improvement in breathing therapy may result in 5 credits being awarded, but a 5 bpm improvement during acupressure therapy may result in 10 credits being awarded, e.g., acupressure therapy may be rewarded 2:1 over breathing therapy.

Figure 21:
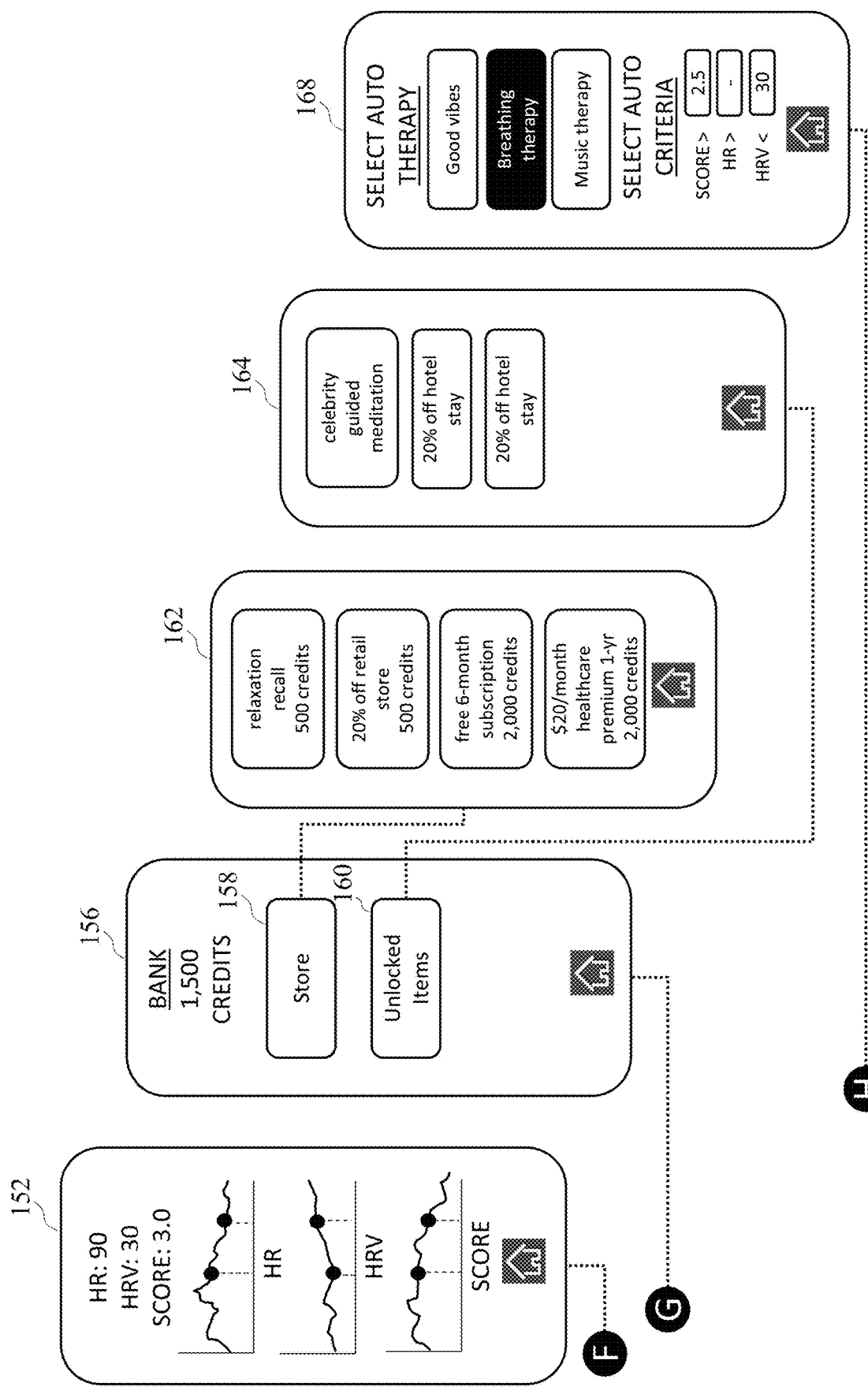
FIG. 21 illustrates another example set of screens output by the software application on the smart device.

Referring to FIG. 21, the software application may include the screen 156 that provides a visual indication of the amount of credits accumulated by the user (e.g., 1,500 credits is shown). The amount of credits accumulated by the user may be stored in the memory MEM of the wearable device 30, the smart device, or in a cloud server accessible by the software application APP. For instance, every time the one or more haptic generators HPT are activated on the wearable device 30 by the controller 84, the controller 84 generates a time stamp for the activation. This activation can be in response to selecting a breathing therapy on screen 126, a song on screen 136, or a time period for "good vibes" on screen 122. In each of these cases, the controller 84 of the wearable device 30 and/or the smart device generates credits for the user based on the selection of the therapy, also referred to as a therapy event and/or an associated therapy time based a look-up table of therapy times stored in the memory MEM for each of the selectable therapies. For instance, if 5 minutes of "good vibes" is selected, the therapy time in the look-up table is 5 minutes. In this case, the user may be given a credit of 1 for one therapy event or may be given a credit of 5 for five minutes of therapy, or a combination thereof, or any other suitable correlation of credits for performing the therapy, such as being based on whether the therapy was successful as described above. Likewise, if a breathing therapy is selected on screen 126, the controller accesses the look-up table to see how many therapy minutes are associated with that selection and then stores the therapy event and the therapy time in the memory MEM and associates this therapy event and therapy time with the date and time of the therapy for later display on the smart device. The controller accumulates therapy events and therapy time to determine the amount of "credits" in the user's "BANK". Additionally, every time the user activates the button 48 for acupressure therapy, the controller 84 generates a starting time stamp and an ending time stamp, e.g., to indicate when the button 48 was depressed and then released in the case of a momentary switch button. The controller 84 can then calculate the amount of time that the button 48 was depressed and the memory controller 84 of the wearable device 30 and/or the smart device generates credits for the user based on the performance of acupressure therapy and the associated therapy time, which in this case is based on an accumulation of activations/deactivations of the button 48 for a single hour, day, etc. The therapy credits can then be based on the total therapy time. In some cases, a therapy event may be generated and stored in the memory MEM by the controller 84 for every 5, 10, or 15 minutes of acupressure therapy performed. Other therapy times required to generate and store a single therapy event in the memory MEM are also contemplated.

This screen 156 also includes a button 158 for accessing a "Store" to redeem the credits, (e.g., use the credits to purchase/unlock items.) and a button 160 for accessing previously unlocked or purchased items. As shown, when selecting the button 158 to access the "Store," software application APP generates screen 162, which shows various options to be purchased/unlocked and the number of credits required. In some versions, items may be automatically unlocked once the user reaches certain credit thresholds (e.g., once the user performs predetermined numbers/ amounts of therapy and/or successful therapy). When selecting button 160 to access the "Unlocked items", software application APP generates screen 164, which shows previously unlocked/purchased items that can now be accessed by the user. Selection of any of these items provides details of these items, such as when redeemed, links to external websites or software applications, links to videos, real US dollar value of the items, codes associated with the items, etc.

Figure 22:
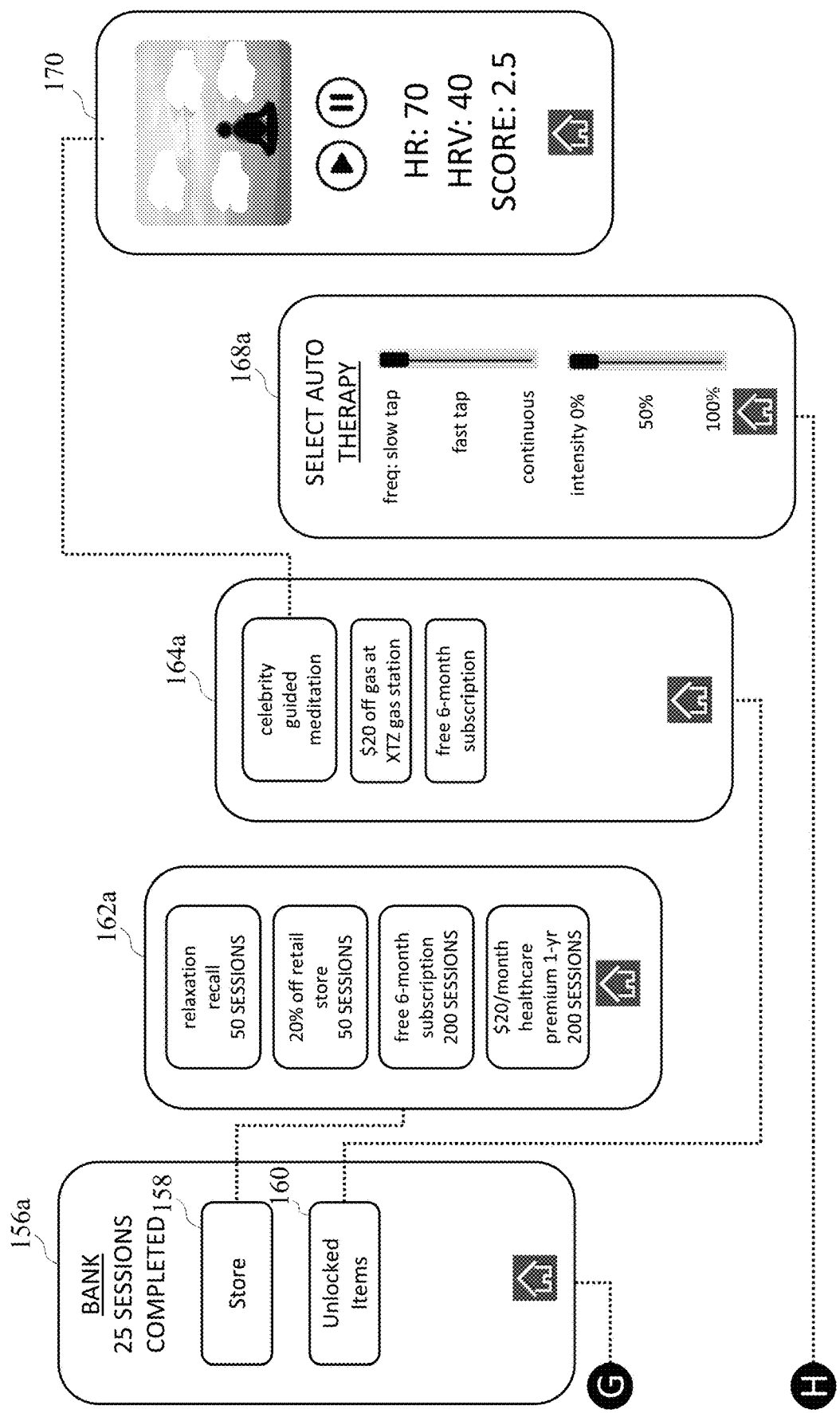
FIG. 22 illustrates another example set of screens output by the software application on the smart device.

For example, as shown in FIG. 22, when the "celebrity guided meditation" is selected by the user, screen 170 is generated, in which the software application APP provides access to a video (with or without audio) that the user can play/pause in a conventional manner. In this case, playing of the video/audio by the controller of the smart device also causes the controller 84 of the wearable device 30 to activate the one or more haptic generators HPT in a manner customized to the video. Such customization can be stored as a haptic file in the memory MEM of the smart device (e.g., cloud memory, local memory, etc.) to be transmitted or streamed to the wearable device 30 for real-time playback via the one or more haptic generators HPT. In other words, the haptic file is stored in the memory MEM of the smart device, wearable device 30, or both, and when the user selects the "play" button on screen 170, the haptic file also starts to be played by the controller on the wearable device 30. Selection of "pause" similarly pauses the video/audio and the haptic file. The vibrations associated with the haptic file may simple be a pattern of calming vibrations (e.g., low frequency and/or low intensity) that matches the calm nature of the meditation video. Of course, if the video is for purposes of energizing a user, then the vibrations generated via the haptic file may be energizing vibrations (e.g., high frequency and/or high intensity). As a result, the user can be coached via video, audio associated with the video, and/or haptically through vibrations on the wearable device 30. Other coaching sessions may also be accessible, such as coaching sessions for breathing therapy, coaching sessions for acupressure therapy, and the like. In the case of a coaching session for breathing therapy, then the haptic file would correspond to breathing cycles used in the video by the coach (real or avatar). In the case of acupressure therapy, the coach (real or avatar) may simple show the user how to find certain acupressure points, where to apply the projection 38 relative to the acupressure points, how much pressure to apply for each of the acupressure points, and/or how long to stimulate each of the acupressure points. During each of the coaching sessions, the controller of the smart device may also display via the screen 170 real-time values of one or more physiological parameters and/or metrics so that the user is able to see how these values change while performing the session. Summary screens could also be generated by the software application APP after the session to show results, such as initial values, final values, changes, % changes, etc., and may also show how many credits were generated by performing the coaching session to be added to the user's "BANK".

Items that are initially inaccessible to the user but that may become accessible as a result of the therapy credits include guided-meditation videos; discounts for hotels, gas, food, airfare, retail stores etc.; discount for subscription costs; healthcare reductions or discounts; and the like. In some cases, users may be given a free subscription for being able to access the incentives on the software application APP, and if the user performs enough therapy, they can continue to receive the subscription for free. For example, users of this system may pay a monthly fee for a subscription, but through enough therapy sessions and accumulation of therapy credits, may be able to pay for the entire subscription or a portion of the subscription indefinitely.

Referring back to FIG. 19, in the version shown, the home screen 100 includes an additional button 166 for "auto therapy settings". Selection of this button 166 causes the software application APP to display screen 168 shown in FIG. 21. On this screen 168, the user is presented with options to program in the software application APP which desired therapy is to be automatically initiated in response to the controller determining that the user has physiological parameters and/or a stress metric SCORE outside of normal values. In some versions, the user may select the therapy to be automatically initiated in response to the one or more operating parameters and/or the stress metric SCORE indicating that the user is experiencing high stress, e.g., values are well outside of normal values indicating an elevated state of stress. Such values may be established based on user baseline values established in the training mode or may be based on normal values for a given population of users. In this case, the user may access the settings via the software application APP and mark which therapy is to be automatically activated by selecting the therapy button associated with that therapy. In some versions, instead of the controller determining which values of the one or more physiological parameters and/or stress metric SCORE indicate high stress for purposes of automatically triggering therapy, the user may be able to set these "triggering values" via the screen 168. In screen 168, the user is able to input which values automatically trigger therapy to begin by inputting the values in text boxes on the screen 168. Other methods of establishing this triggering criteria may also be used, such as selectable options of values. Other physiological parameters, metrics, etc. could also be set by the user.

Once the desired therapy type and the triggering criteria is set by the user via inputs in the screen 168, the software application APP stores these selections in the memory MEM of the smart device, which may also be communicated to the controller 84 and memory of the wearable device 30. Accordingly, the wearable device 30 can thereafter monitor the values for the respective physiological parameters and/or metrics and determine when the triggering criteria is met. In response, the wearable device 30 automatically activates the one or more haptic generators HPT to begin the selected therapy, based on the last settings of that particular therapy. The smart device may trigger the therapy and/or the wearable device 30 or 200 may trigger the therapy. The wearable device 200 may monitor/calculate the values and transmit them to the smart device and/or the wearable device 30, which may then automatically trigger the therapy.

FIG. 22 shows a set of alternative screens 156a, 162a, 164a, 168a. In this version, the therapy credits are based solely on the number of therapy sessions (therapy events) completed by the user (see, e.g., 25 SESSIONS in the "BANK"). In this version, the user has already unlocked a free 6-month subscription. If this item was selected, another screen (not shown), would provide details of this subscription, including its start and end dates and how the user obtained the subscription (e.g., how many credits were required).

FIG. 22 also shows an alternative screen 168a for the user to set what happens in the case of automatic therapy, i.e., when one or more of the physiological parameters and/or the stress metric SCORE fall outside normal levels, reach/meet alert levels (high or low), meet user-set levels, etc. In the version shown, the user is able to set a vibration frequency and/or vibration intensity for the one or more haptic generators HPT for vibration therapy. Accordingly, for users that wish for automatic therapy to be subtle, and less distracting, they are able to select a low frequency vibration with a low intensity, but for users that wish to be alerted immediately when automatic therapy begins, they can set a higher frequency and higher intensity. If breathing therapy or music therapy are the automatically activated therapies, then the settings for frequency may be absent on this screen 168a, but the user may still vary the intensity of the one or more haptic generators HPT via this screen 168a.

Figure 23:
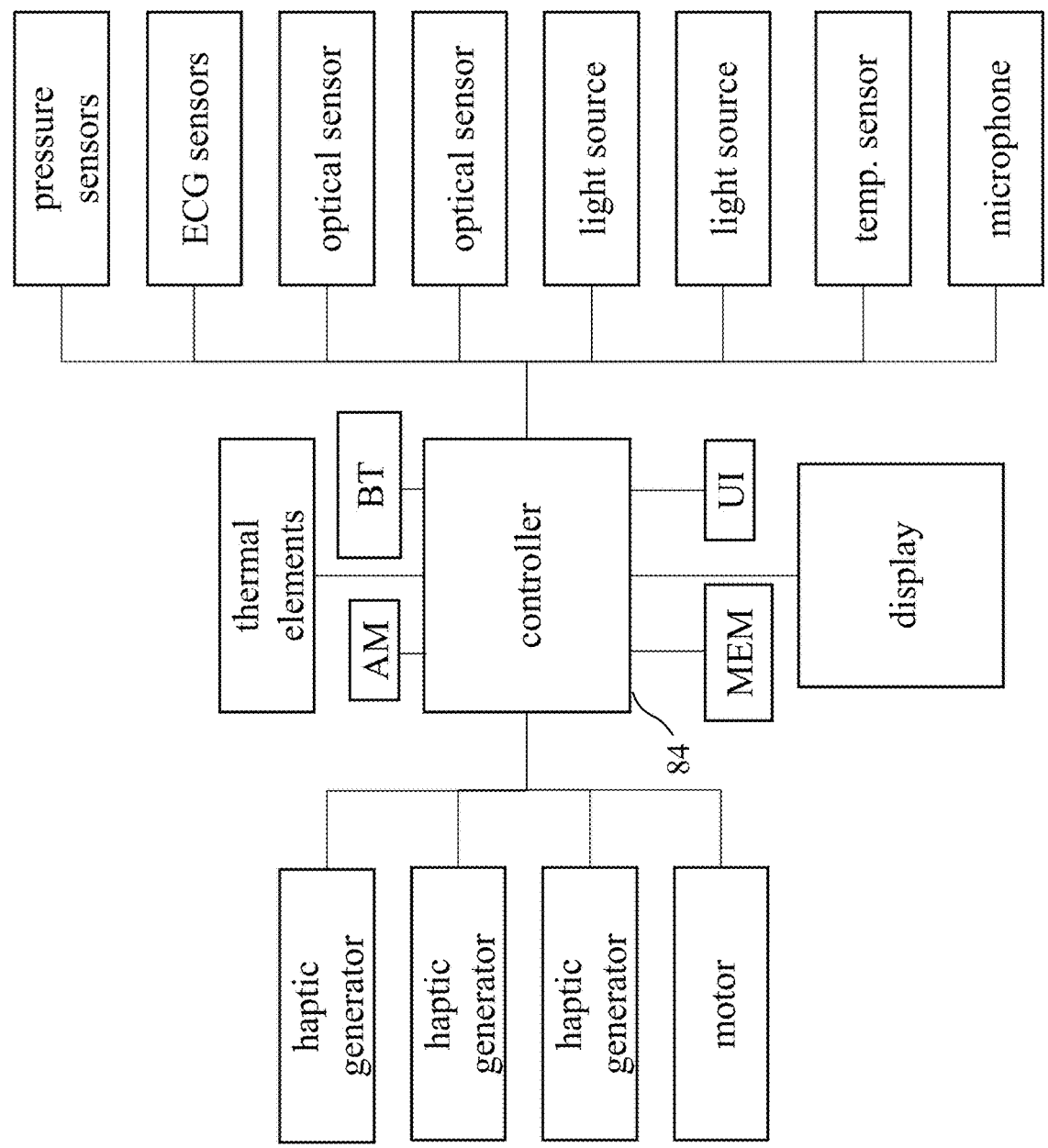
FIG. 23 is a block diagram of another control system for the wearable device.

A temperature therapy system is coupled to the wearable support 32. The temperature therapy system comprises one or more thermal elements (see FIG. 23) carried by the wearable support 32. The thermal elements may include heating elements and/or cooling elements. The thermal elements may be small coils, ribbons, or strips of wire that generate heat in response to supplied electrical current, and/or may be a fluid cooling circuit, thermoelectric elements (e.g., coolers that operate on the Peltier effect), or the like that cool a surface. Other forms of thermal elements may also be used. In one version, there are four thermal elements embedded into the wearable support, beneath an interface surface of the wearable support 32. In other versions, the thermal elements may be disposed on the interface surface for direct contact with the user. A single thermal element or multiple thermal elements could be employed. The thermal elements are intended to provide thermal therapy to the user by warming or cooling the user's skin surface via the wearable support 32. The thermal elements are operatively coupled to the controller 84.

The projection 38 may be spherically-shaped, hemispherically shaped, or have any suitable shape for engaging the user's skin. The projection 38 may have a smooth portion (arcuate, flat, or the like) that is located to engage the user's skin. In some versions, multiple projections may be provided to engage the user's skin. The projections 38 may be connected to the wrist band and/or the housing 36 in any suitable manner, including welding, adhesive, fasteners, sewing, heat staking, or the like.

Figures 24A, 24B:
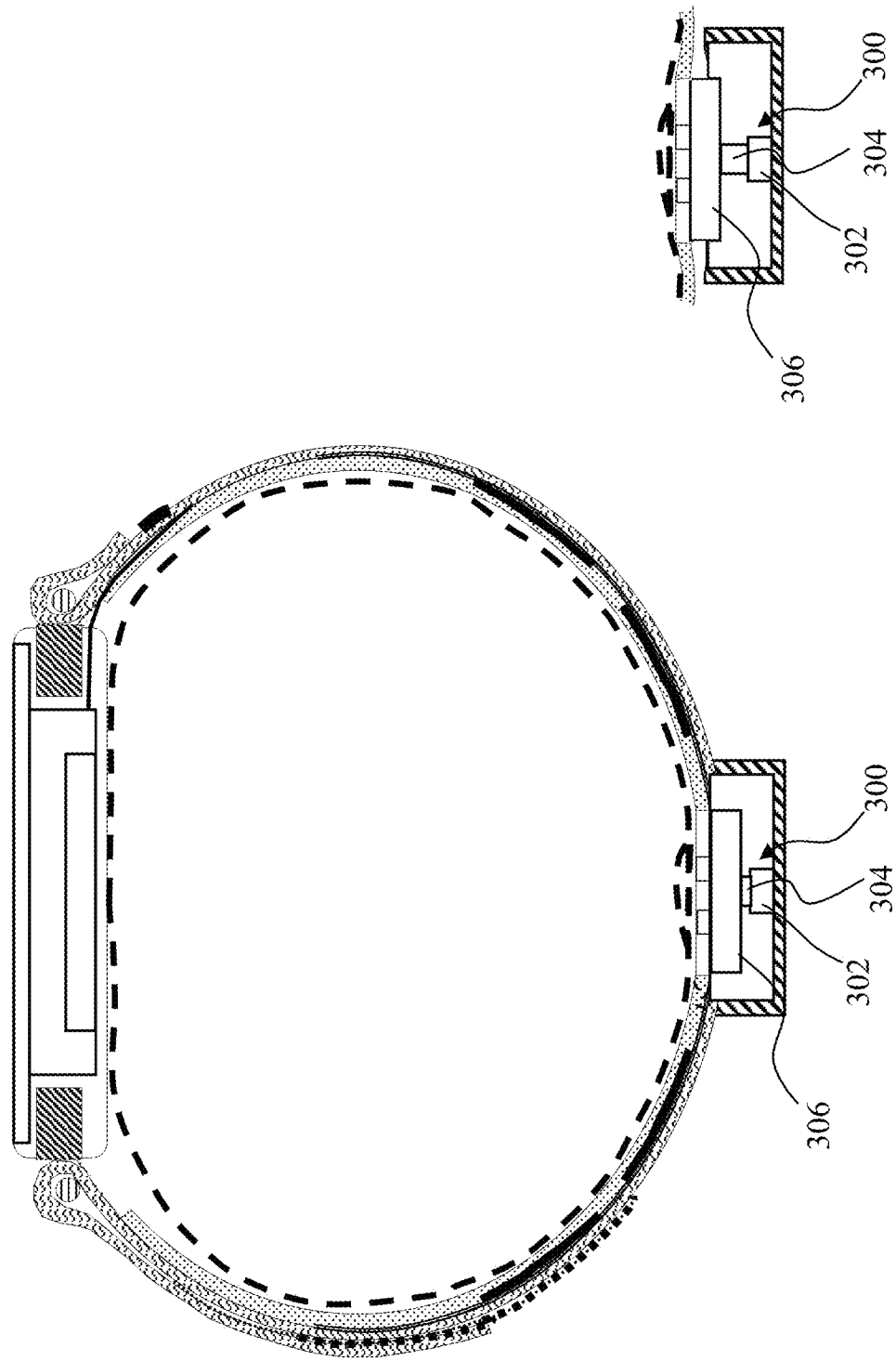
FIGS. 24A and 24B illustrate a wearable device including a linear actuator having a rod movable between first and second states.

FIGS. 24A and 24B illustrate a wearable device in which a linear actuator 300 is connected to the controller 84 to be activated by the controller 84. The linear actuator 300 has a base 302 mounted to the housing. A linearly-movable rod 304 is extendable/retractable from the base 302. A pressure-applying body 306 is fixed to one end of the rod 304 to move with the rod 304. During actuation of the linear actuator 300, the pressure-applying body 306 is moved toward the acupressure point P6 to provide therapy to the user. The pressure-applying body 306 is shown beneath the sensor housing to move the sensor housing to apply such pressure, but the pressure-applying body 306 may be in direct contact with the user's wrist in some versions, or located underneath flexible material of the wearable support 32 to protrude into the flexible material (e.g., beneath a flexible layer). In some versions, the pressure-applying body 306 may have a shape similar to the projection 38, or may have a semi-spherical shape, or other shape. In some versions, the rod 304 may act as the pressure-applying body and may be located beneath the sensor housing to move the sensor housing to apply such pressure, but the rod 304 may be in direct contact with the user's wrist in some versions, or located underneath flexible material of the wearable support 32 to protrude into the flexible material (e.g., beneath a flexible layer) to provide therapy.

Figure 25:
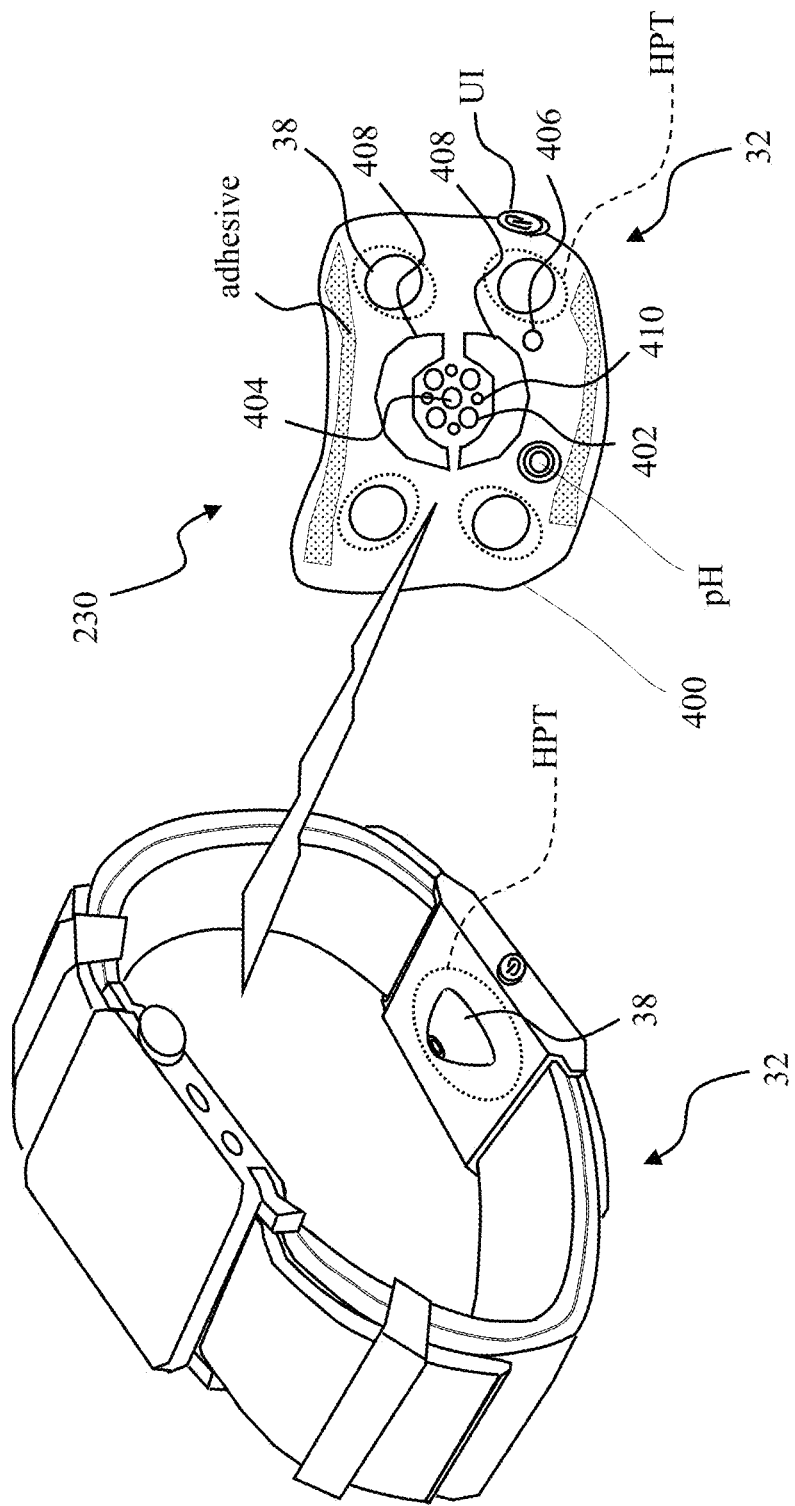
FIG. 25 illustrates a pair of wearable devices.

Referring to FIG. 25, two wearable devices are shown that could each operate in the same manner as the wearable devices previously described, including providing all of the various therapies previously described and communicating with a separate smart device as previously described. Each of these wearable devices includes a separate wearable support 32, and one has a display unit. The wearable supports 32 may be any suitable wearable support. Here, one of the wearable supports 32 includes a wrist band as previously described above and the other wearable support 32 includes an adhesive patch. The adhesive patch includes a body 400 shaped to be applied to a user's chest, back, abdomen, back of arm, or any other suitable location. One or more sensors 402, 404, 406, 408, pH, and light sources 410, such as those previously described are carried by the body 400 to measure physiological parameters of the user and pressure of the patch against the user. One or more haptic generators HPT are carried by the body 400 to provide haptic therapy as previously described. The body 400 provides a housing or enclosure for the sensors, light sources, haptic generators HPT, controller 84, and other electronic components. The body 400 may be attached to the user via adhesive, bands, garments, etc. The wearable devices each have a haptic therapy unit with one or more haptic generators HPT to provide haptic therapy to two separate locations on the body of the user. The controller of the display unit on the wrist-worn wearable device may communicate with the separate controller 84 in the body 400 via any suitable wireless communication method (e.g., WiFi, Bluetooth, Zigbee, etc.) to activate the haptic generators HPT of one or both of the haptic therapy units to provide haptic therapy as previously described. One or more projections (four shown), like those previously described, may also be located on the patch to apply pressure to desired areas of the user that require haptic therapy.

Figure 26:
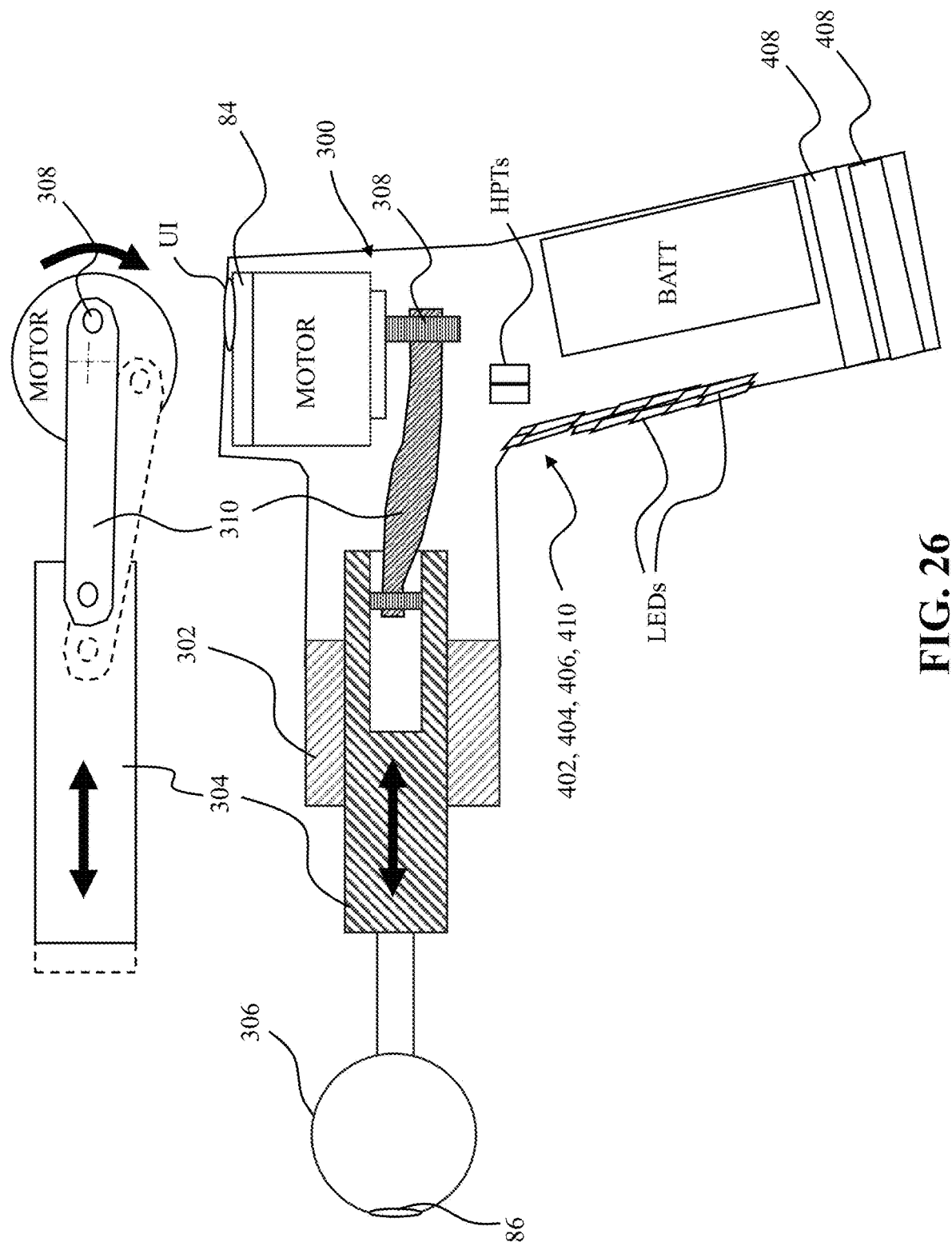
FIG. 26 illustrates a therapy device.

FIG. 26 illustrates another therapy device using a linear actuator 300 connected to the controller 84 to be activated by the controller 84. This therapy device may be used in the same manner as previously described for the other devices, including for use in haptic therapy, breathing therapy, heating therapy, or cooling therapy. The linear actuator 300 has a base 302 mounted and fixed to the housing. A linearly-movable rod 304 is extendable/retractable from the base 302 and is driven by a rotary motor having an eccentric pin driver 308. A link 310 has a first end pivotally connected to the eccentric pin driver 308 and a second end pivotally connected to the linearly-movable rod 304. By virtue of the eccentric pin driver 308 and pivotal connections of the link 310, as the motor rotates in the housing, the eccentric pin driver 308 rotates, spaced from a center of the motor, thereby driving the linear motion of the rod 304 (see motion illustration). The pressure-applying body 306, in this case a massage head, is connected to one end of the rod 304 to move with the rod 304. During actuation of the linear actuator 300, the pressure-applying body 306 is moved toward and away from the user in a percussive manner to provide percussion therapy to the user. An example of such a linear actuator and its use is shown in U.S. Pat. No. 10,993,874 to Marton et al., hereby incorporated herein by reference. Pressure sensor 86 may be located on the pressure-applying body 306 to sense pressure between the pressure-applying body 306 and the user.

Figure 27:
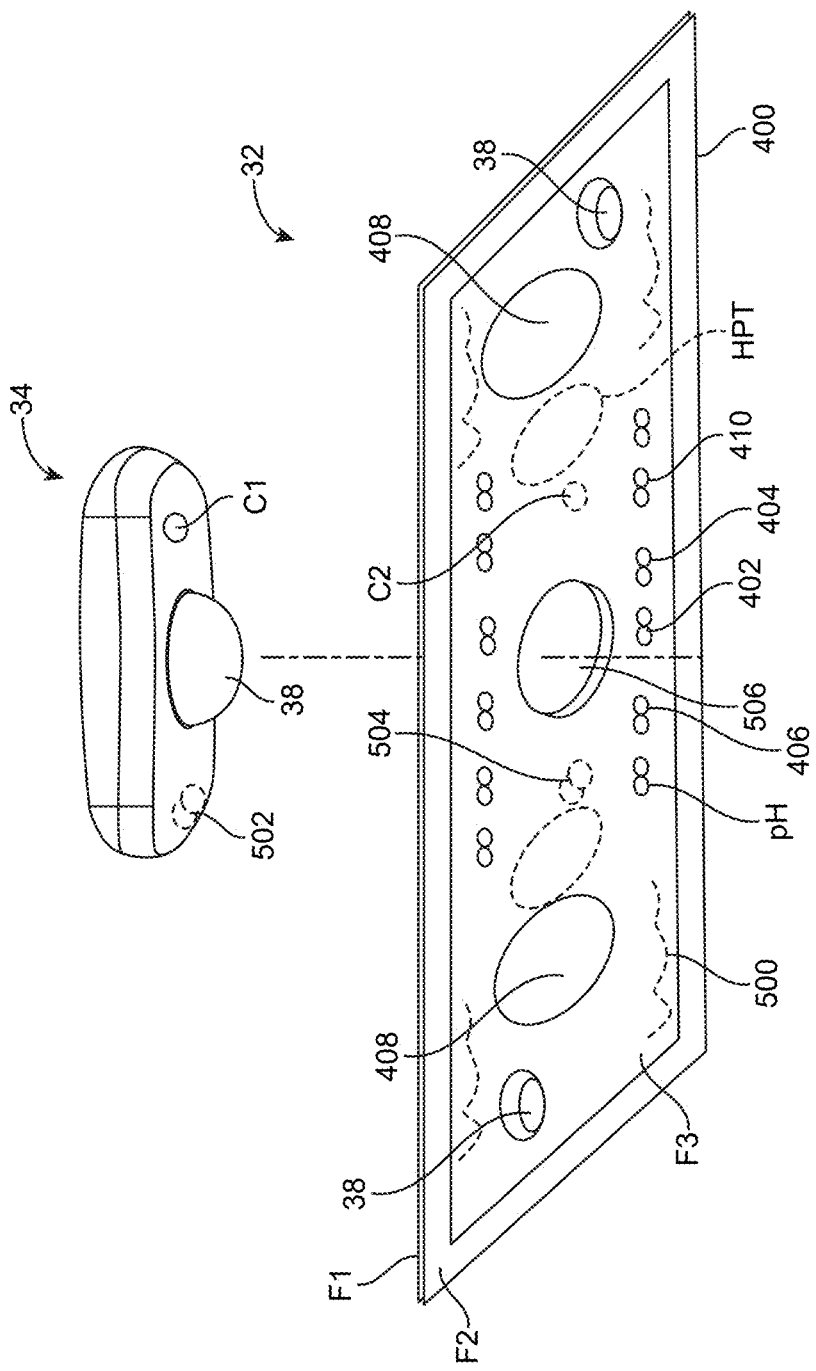
FIG. 27 is a perspective view of an adhesive patch and housing unit releasably connecting to the adhesive patch.

Referring to FIG. 27, another example of a wearable adhesive patch is shown. The adhesive patch includes a pair of flexible layers F1, F2 attached to one another and an adhesive layer F3 attached to the flexible layers F1, F2 to adhere the adhesive patch to the user. The adhesive patch layers form a body 400 shaped to be applied to a user's chest, back, abdomen, back of arm, or any other suitable location. One or more sensors 402 (light sources), 404 (light sensors), 406 (temperature sensor), 408 (ECG electrodes), pH sensors, and light therapy sources 410 (e.g., red light therapy LEDs, blue light therapy LEDs, etc.), such as those previously described are carried by the body 400 to measure physiological parameters of the user and pressure of the patch against the user, or to provide therapy to the user. Thermal elements 500 for heating or cooling the user are also carried by the body 400 and may have exposed surfaces to contact skin of the user. One or more haptic generators HPT may also be carried by the body 400 to provide therapy as previously described. The sensors, light sources, haptic generators HPT, thermal elements, etc. may be attached or embedded in the body 400 in any suitable manner, including disposed between the flexible layers F1, F2, attached by adhesive, welding, fasteners, etc. The body 400 may provide a housing or enclosure for the sensors, light sources, haptic generators HPT, and other electronic components. The body 400 may be attached to the user via the adhesive layer F3, bands, garments, etc.

In this version, the housing unit 34 is coupled to and supported by the wearable support 32. The housing unit 34 may be releasably coupled to the body 400 via snap-fit attachment, magnets/magnetically attractive elements 502, 504, bayonet connections, or the like. The projection 38 is sized and shaped congruently with an opening 506 in the body 400 to pass through the opening 506 to engage the skin or garment of the user when worn to provide massage therapy. Projections 38 may also be mounted to the underside of the adhesive patch to engage the user (underside shown in FIG. 27). Once the housing unit 34 is connected to the body 400, the battery BT and controller 84 of the housing unit 34 is connected to the electrical components on the body 400 to power and control those components via flex circuits in the body 400 and electrical contacts C1, C2 between the housing unit 34 and the body 400.

Once connected, the user may perform one or more of the therapies previously described, including massage therapy, vibration therapy, light therapy, heating therapy, cooling therapy, breathing therapy, meditation, and the like, while also simultaneously measuring/calculating one or more physiological parameters such as heart rate, HRV, glucose, ECG, temperature, etc. of the user to see the effects of these therapies on the user. These measurements/calculations could also be input into a feedback loop saved in the controller 84 to control the wearable device, such as by reducing vibration intensity as heart rate is reduced, or vice versa. Temperature could also be controlled in a closed feedback loop. The vibrations could likewise be controlled by the controller 84 to match the current heart rate of the user or be set just below the user's current heart rate (e.g., 1 bpm lower) to help lower the user's current heart rate until a target heart rate is reached. The vibrations could also automatically start via the controller 84 in response to the current heart rate exceeding a predefined threshold.

Figure 28A:
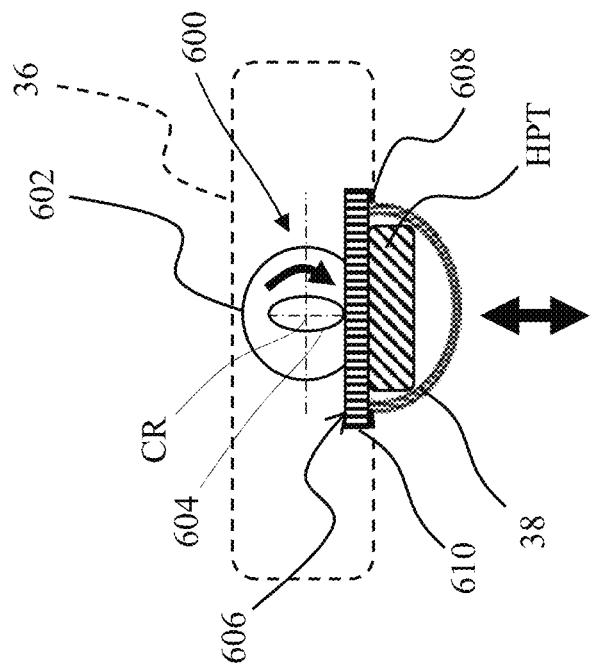
FIGS. 28A and 28B illustrates a percussion drive in two different states.
Figure 28B:
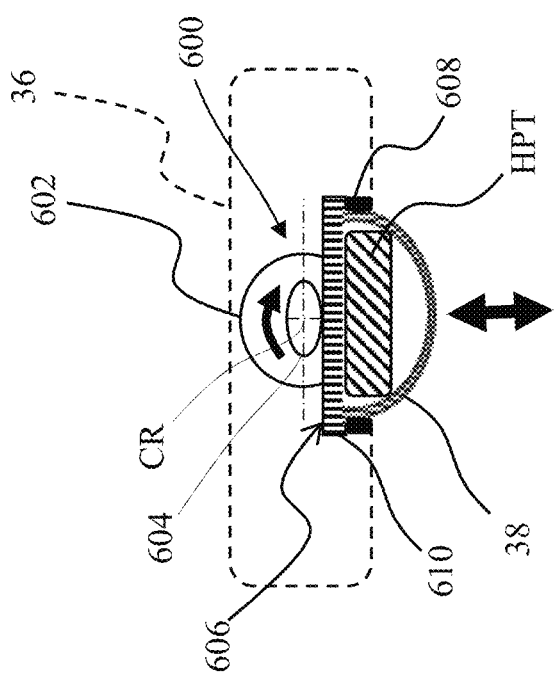

FIGS. 28A and 28B illustrate two states of a percussion drive 600 that can be used with any of the devices disclosed herein to provide percussive movement to the projection 38 or to other forms of massage heads. In this case, the thermal elements may also be incorporated into the projection 38 to heat or cool the projection 38 so that the user can also receive thermal therapy, in addition to massage therapy. The percussion drive 600 has a limited number of moving parts so that it can be packaged into a space of less than 400 cc, less than 200 cc, or less than 100 cc. In the version shown, there are only two, relatively rigid, moving parts.

The percussion drive 600 includes a motor 602 fixed to the housing 36, such as a brushless DC motor or any other suitable motor connected to the controller 84 to be driven by the controller 84. The motor 602 has a rotary drive shaft and a cam 604 fixed to the drive shaft to rotate with the drive shaft (one of the rigid moving parts). In the version shown, the cam 604 has an oblong, elliptical shape with opposing cam lobes. The cam 604 is in constant contact with a driving surface 606 of the projection 38 (the other relatively rigid moving part) to move the driving surface 606 in a percussive manner.

The cam 604 is oblong so that as the cam 604 rotates under the power of the motor 602 (controlled by the controller 84) about a center of rotation CR, the distance between the center of rotation CR of the motor 602 and the driving surface 606 changes. When the long dimension of the cam 604 is perpendicular to the driving surface 606 (FIG. 28B), then the distance is at its maximum and when the short dimension of the cam 604 is perpendicular to the driving surface 606 (FIG. 28A), then the distance is at its minimum. Other cam shapes are possible with different lobe shapes, numbers, styles, etc. In the version shown, since the cam lobes are diametrically opposed, for each complete rotation of the motor 602, the maximum and minimum distances are each reached twice.

One or more resilient bodies 608 are disposed between rim 610 of the projection 38 and the housing 36 to provide a biasing force to keep the driving surface 606 in contact with the cam 604 by applying a biasing force that biases the projection 38 toward the cam 604. Each resilient body 608 (moving part, but less rigid than the other moving parts) may be formed of rubber or other suitable resilient and/or compressible material (e.g., an o-ring), one or more compression springs, or the like. As the projection 38 is applied to the user, additional forces from the user will assist with keeping the driving surface 606 of the projection 38 in contact with the cam 604 as well.

The percussion drive 600 could be employed in any of the devices described herein, including in combination with any of the features described herein to yield a device capable of any of the prior therapies disclosed herein, including, but not limited to, massage therapy (includes percussion therapy), vibration therapy, light therapy, heating therapy, cooling therapy, breathing therapy, meditation, and the like, while also simultaneously measuring/calculating one or more physiological parameters such as heart rate, HRV, glucose, ECG, temperature, etc. of the user to see the effects of these therapies on the user. In some versions, the motor 602 may have a driver controlled to additionally provide vibration therapy and/or breathing therapy to the user by simply controlling operation of the motor 602 to oscillate at a particular frequency to create vibrations and/or sounds without fully turning its drive shaft.

The terms "comprise", "comprises," and "comprising", "has", "have", and "having", "include", "includes", and "including" are open-ended linking verbs. For instance, a system, device, or apparatus, or element thereof, that "comprises," "has," or "includes" one or more elements possesses those one or more elements, but is not limited to possessing only those one or more elements.

Numerous wearable devices are disclosed herein with various combinations of therapy devices for providing therapy to the user and/or measuring devices for measuring physiological parameters of the user. It should be appreciated that other wearable devices are also contemplated that include one or more of these therapy devices, one or more of these measuring devices, or combinations thereof, even though not described in detail. It should also be appreciated that any one or more of the various therapy devices described can be used in combination with any one or more of the various measuring devices to form additional wearable devices.

What is claimed is:

1. A massager for providing massage therapy and breathing therapy to a user, the massager comprising:
   one or more haptic generators;
   a housing carrying the one or more haptic generators;
   a massage head coupled to the housing to engage the user to provide the massage therapy to the user, wherein the massage head has an arcuate contact surface for engaging the user to provide the massage therapy to the user;
   a controller disposed in the housing to control the one or more haptic generators;
   a user interface coupled to the controller and a display coupled to the controller; and
   one or more sensors coupled to the controller, wherein the controller is configured to monitor one or more physiological parameters of the user with the one or more sensors and to display a value of the one or more physiological parameters on the display,
   wherein the controller is configured to generate vibrations with the one or more haptic generators to be felt by the user such that the vibrations guide the user through inhale and exhale phases of the breathing therapy, and
   wherein the controller is configured to communicate with a separate smart device to coordinate operation of the one or more haptic generators of the massager with display of visual guidance on the separate smart device to guide the user through the inhale and the exhale phases of the breathing therapy, such that the user is visually guided on when to inhale and exhale by the separate smart device while simultaneously being vibrationally guided on when to inhale and exhale by the one or more haptic generators of the massager by varying the vibrations between the inhale and the exhale phases of the breathing therapy,
   wherein the massage head is slidable relative to the housing.

2. The massager of claim 1, wherein the controller is configured to determine the value of the one or more physiological parameters during the breathing therapy.

3. The massager of claim 1, further comprising one or more thermal elements configured to be operatively coupled to the controller to provide thermal therapy to the user.

4. The massager of claim 3, wherein the one or more thermal elements include heating elements.

5. The massager of claim 4, wherein the one or more thermal elements include cooling elements.

6. The massager of claim 3, wherein the one or more thermal elements include thermoelectric elements that operate on the Peltier effect to cool an interface surface arranged to be in direct contact with the user.

7. The massager of claim 1, further comprising near-infrared light emitting sources coupled to the controller and arranged to emit light on the user.

8. The massager of claim 1, wherein the one or more sensors coupled to the controller includes one or more optical sensors coupled to the controller for measuring a heart rate of the user.

9. The massager of claim 1, wherein the controller is configured to communicate with the separate smart device through radio frequency communication and using a software application running on the separate smart device, wherein the software application is configured to present selectable breathing therapies to the user on the separate smart device and to display on the separate smart device the value of the one or more physiological parameters monitored by the one or more sensors of the massager.

10. The massager of claim 1, wherein the one or more haptic generators include one or more vibration motors.

11. The massager of claim 1, wherein the controller is configured to measure a current heart rate of the user with the one or more sensors.

12. The massager of claim 11, wherein the controller is configured to operate the one or more haptic generators to generate vibrations that mimic the current heart rate of the user.

13. The massager of claim 12, wherein the controller is configured to operate the one or more haptic generators to generate vibrations that mimic a lower heart rate, below the current heart rate of the user.

14. A massager for providing massage therapy and breathing therapy to a user, the massager comprising:
   one or more haptic generators;
   a housing carrying the one or more haptic generators;
   a massage head coupled to the housing to engage the user to provide the massage therapy to the user, wherein the massage head has an arcuate contact surface for engaging the user to provide the massage therapy to the user;
   a controller disposed in the housing to control the one or more haptic generators;
   a user interface coupled to the controller and a display coupled to the controller; and
   one or more sensors coupled to the controller, wherein the controller is configured to monitor one or more physiological parameters of the user with the one or more sensors and to display a value of the one or more physiological parameters on the display,
   wherein the controller is configured to generate vibrations with the one or more haptic generators to be felt by the user such that the vibrations guide the user through inhale and exhale phases of the breathing therapy, and
   wherein the controller is configured to communicate with a separate smart device to coordinate operation of the one or more haptic generators of the massager with display of visual guidance on the separate smart device to guide the user through the inhale and the exhale phases of the breathing therapy, such that the user is visually guided on when to inhale and exhale by the separate smart device while simultaneously being vibrationally guided on when to inhale and exhale by the one or more haptic generators of the massager by varying the vibrations between the inhale and the exhale phases of the breathing therapy, and a linearly-movable rod to move the massage head relative to the housing.

15. The massager of claim 14, wherein the linearly-movable rod forms part of a linear actuator having a base mounted to the housing, wherein the linearly-movable rod extends and retracts from the base to move the massage head relative to the housing.

16. The massager of claim 14, wherein the controller is configured to determine the value of the one or more physiological parameters during the breathing therapy.

17. The massager of claim 14, wherein the one or more sensors coupled to the controller includes one or more optical sensors coupled to the controller for measuring a heart rate of the user.

18. The massager of claim 14, wherein the controller is configured to communicate with the separate smart device through radio frequency communication and using a software application running on the separate smart device, wherein the software application is configured to present selectable breathing therapies to the user on the separate smart device and to display on the separate smart device the value of the one or more physiological parameters monitored by the one or more sensors of the massager.

19. The massager of claim 14, wherein the one or more haptic generators include one or more vibration motors.

20. The massager of claim 14, wherein the controller is configured to measure a current heart rate of the user with the one or more sensors.

21. The massager of claim 20, wherein the controller is configured to operate the one or more haptic generators to generate vibrations that mimic the current heart rate of the user.

22. The massager of claim 21, wherein the controller is configured to operate the one or more haptic generators to generate vibrations that mimic a lower heart rate, below the current heart rate of the user.

* * * * *